United States Patent
Pichler

(10) Patent No.: US 12,123,546 B2
(45) Date of Patent: Oct. 22, 2024

(54) LOAD BALANCING ARM FOR MEDICAL DEVICE SUPPORT SYSTEM

(71) Applicant: American Sterilizer Company, Mentor, OH (US)

(72) Inventor: Jerime Josef Pichler, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 138 days.

(21) Appl. No.: 17/962,762

(22) Filed: Oct. 10, 2022

(65) Prior Publication Data

US 2023/0120143 A1 Apr. 20, 2023

Related U.S. Application Data

(60) Provisional application No. 63/256,713, filed on Oct. 18, 2021.

(51) Int. Cl.
*F16M 13/02* (2006.01)

(52) U.S. Cl.
CPC ........ *F16M 13/027* (2013.01); *F16M 2200/04* (2013.01)

(58) Field of Classification Search
CPC ...... F16M 13/02; F16M 13/027; F16M 11/22; F16M 11/24; F16M 11/2092; F16M 2200/04
See application file for complete search history.

(56) References Cited

U.S. PATENT DOCUMENTS

| | | | |
|---|---|---|---|
| 2,150,975 | A | 3/1939 | Hunsicker |
| 2,941,776 | A | 6/1960 | Lauterbach |
| 3,240,925 | A | 3/1966 | Paschke et al. |
| 3,547,390 | A | 12/1970 | Mehr |
| 4,080,530 | A | 3/1978 | Krogsrud |
| 4,160,536 | A | 7/1979 | Krogsrud |

(Continued)

FOREIGN PATENT DOCUMENTS

| | | |
|---|---|---|
| JP | 2016030315 A | 3/2016 |
| WO | 0145627 A1 | 6/2001 |
| WO | 03025453 A1 | 3/2003 |

OTHER PUBLICATIONS

Jon Lawson, "A balancing act: the benefits of using counterbalance technology", Engineer Live, May 13, 2020, pp. 1-7.

(Continued)

*Primary Examiner* — Eret C McNichols
(74) *Attorney, Agent, or Firm* — Renner, Otto, Boisselle & Sklar, LLP

(57) ABSTRACT

A load balancing arm for a medical device support system includes a proximal hub, a support arm, first and second springs, and a link. The link has a proximal end pivotably mounted to a link bearing element for pivotable movement about a link pivot axis, and a distal end pivotably mounted to a distal end of the first spring and a proximal end of the second spring. The link and first and second springs are configured such that the biasing forces exerted by the first and second springs are transmitted through the link to the link bearing element thereby to generate a moment about a main pivot axis of a proximal hub that counters a moment generated by a medical device load at a distal end of the support arm.

23 Claims, 55 Drawing Sheets

(56) References Cited

U.S. PATENT DOCUMENTS

| | | | |
|---|---|---|---|
| 4,390,932 A | 6/1983 | Matsui et al. | |
| 4,447,031 A | 5/1984 | Souder, Jr. et al. | |
| 4,695,024 A | 9/1987 | Haven | |
| 4,744,019 A | 5/1988 | Krogsrud | |
| 4,770,384 A | 9/1988 | Kuwazima et al. | |
| 4,836,478 A | 6/1989 | Sweere | |
| 4,954,043 A | 9/1990 | Yoshida et al. | |
| 5,038,261 A | 8/1991 | Kloos | |
| 5,123,621 A | 6/1992 | Gates | |
| 5,186,337 A | 2/1993 | Foster et al. | |
| 5,348,260 A | 9/1994 | Acevedo | |
| 5,618,090 A | 4/1997 | Montague et al. | |
| 5,738,316 A | 4/1998 | Sweere et al. | |
| 5,743,503 A | 4/1998 | Voeller et al. | |
| 5,799,917 A | 9/1998 | Li | |
| 5,826,846 A | 10/1998 | Buccieri et al. | |
| 6,012,693 A | 1/2000 | Voeller et al. | |
| 6,012,821 A | 1/2000 | Yeaney et al. | |
| 6,076,785 A | 6/2000 | Oddsen, Jr. | |
| 6,328,458 B1 | 12/2001 | Bell et al. | |
| 6,592,090 B1 | 7/2003 | Li | |
| 6,639,623 B2 | 10/2003 | Howell et al. | |
| 6,736,364 B2 | 5/2004 | Oddsen, Jr. | |
| 6,793,380 B2 * | 9/2004 | Kupfer | A61B 90/35 248/583 |
| 6,819,550 B2 | 11/2004 | Jobs et al. | |
| 6,899,307 B2 | 5/2005 | Strauss et al. | |
| 7,014,157 B2 | 3/2006 | Oddsen | |
| 7,097,145 B2 | 8/2006 | Turner | |
| 7,100,880 B2 | 9/2006 | Oddsen, Jr. | |
| 7,252,277 B2 | 8/2007 | Sweere et al. | |
| 7,364,127 B2 | 4/2008 | Huang | |
| 7,395,995 B2 | 7/2008 | Chen | |
| 7,464,909 B2 | 12/2008 | Li | |
| 7,562,851 B2 | 7/2009 | Hein et al. | |
| 7,661,643 B2 | 2/2010 | Oh | |
| 7,677,516 B2 | 3/2010 | Oddsen, Jr. | |
| 7,726,616 B2 * | 6/2010 | Zhang | F16M 11/2021 248/920 |
| 7,770,860 B1 | 8/2010 | Culpepper et al. | |
| 7,837,674 B2 | 11/2010 | Cooper | |
| 7,997,211 B2 | 8/2011 | Peterson et al. | |
| 8,070,120 B2 | 12/2011 | Lange et al. | |
| 8,177,181 B2 | 5/2012 | Papendieck et al. | |
| 8,328,151 B2 | 12/2012 | Gwag | |
| 8,342,467 B2 | 1/2013 | Stachowski et al. | |
| 8,430,564 B2 | 4/2013 | Simmons et al. | |
| 8,439,319 B2 | 5/2013 | Page | |
| 8,465,203 B2 | 6/2013 | Barker et al. | |
| 8,899,125 B2 | 12/2014 | Bax et al. | |
| 9,027,894 B2 | 5/2015 | Sapper et al. | |
| 9,188,275 B2 | 11/2015 | Ergun et al. | |
| 9,228,696 B2 | 1/2016 | Borloz et al. | |
| 9,277,812 B2 | 3/2016 | Bennett et al. | |
| 9,316,346 B2 | 4/2016 | Lau et al. | |
| 9,657,889 B1 | 5/2017 | Chumakov | |
| 9,706,843 B2 | 7/2017 | Hung | |
| 9,752,723 B2 | 9/2017 | Hung | |
| 10,285,772 B2 * | 5/2019 | Oginski | A61G 12/002 |
| 10,400,944 B2 | 9/2019 | Bax et al. | |
| 10,976,001 B2 | 4/2021 | Hung | |
| 11,118,729 B2 | 9/2021 | Zebarjad et al. | |
| 11,131,421 B2 | 9/2021 | Hung | |
| 11,320,090 B2 * | 5/2022 | Borg | F16M 11/2064 |
| 11,666,412 B2 * | 6/2023 | Pichler | A61B 90/50 211/85.13 |
| 11,725,772 B1 * | 8/2023 | Chumakov | F16M 11/2092 248/284.1 |
| 2004/0188578 A1 | 9/2004 | Turner | |
| 2004/0245419 A1 * | 12/2004 | Sweere | F16M 11/105 248/278.1 |
| 2006/0273231 A1 | 12/2006 | Huang | |
| 2007/0001076 A1 | 1/2007 | Asamarai et al. | |
| 2011/0147546 A1 | 6/2011 | Monsalve et al. | |
| 2011/0260017 A1 | 10/2011 | Monsalve et al. | |
| 2013/0112828 A1 | 5/2013 | Sapper et al. | |
| 2013/0146728 A1 | 6/2013 | Ergun et al. | |
| 2016/0346940 A1 | 12/2016 | Bax et al. | |
| 2017/0340408 A1 | 11/2017 | Oginski et al. | |
| 2018/0051850 A1 | 2/2018 | Bax et al. | |
| 2018/0256281 A1 | 9/2018 | Bellows et al. | |
| 2019/0076115 A1 | 3/2019 | Bax et al. | |
| 2019/0145473 A1 | 5/2019 | Puterbaugh et al. | |
| 2020/0025326 A1 | 1/2020 | Ren et al. | |
| 2020/0246110 A1 | 8/2020 | Pichler et al. | |
| 2022/0133431 A1 * | 5/2022 | Bellows | A61B 90/50 606/1 |

OTHER PUBLICATIONS

International Search Report and Written Opinion for corresponding International Application PCT/US2019/064397 mailed Mar. 17, 2020.

International Preliminary Report on Patentability for corresponding International Application PCT/US2019/064397 mailed May 7, 2021.

International Search Report and Written Opinion for corresponding PCT International Application No. PCT/US2022/046160 mailed Jan. 27, 2023.

* cited by examiner

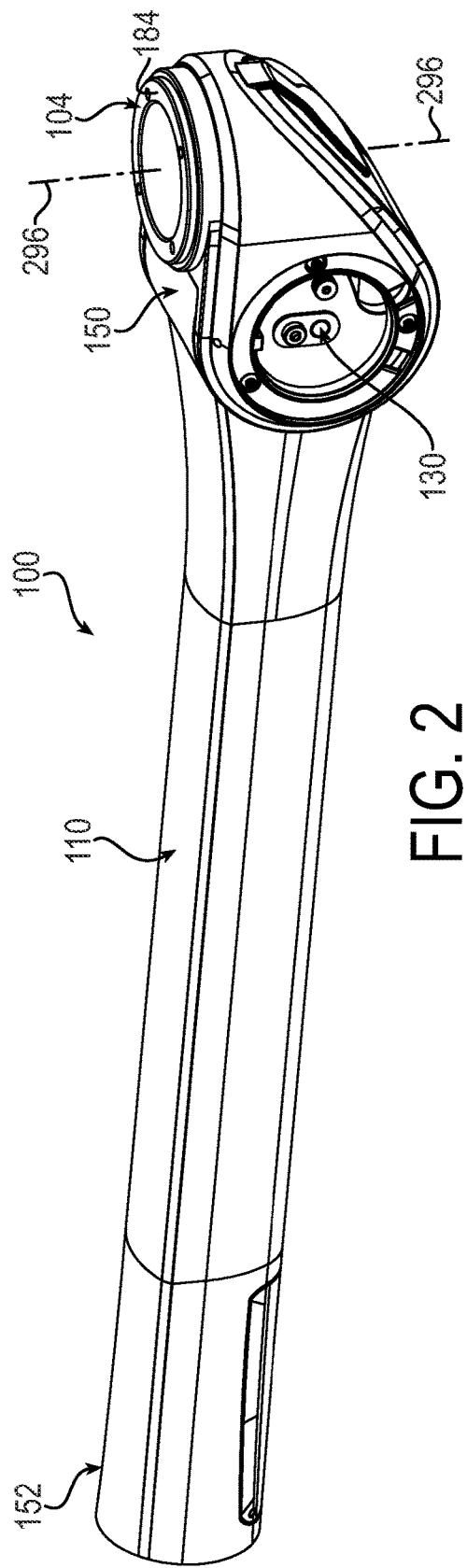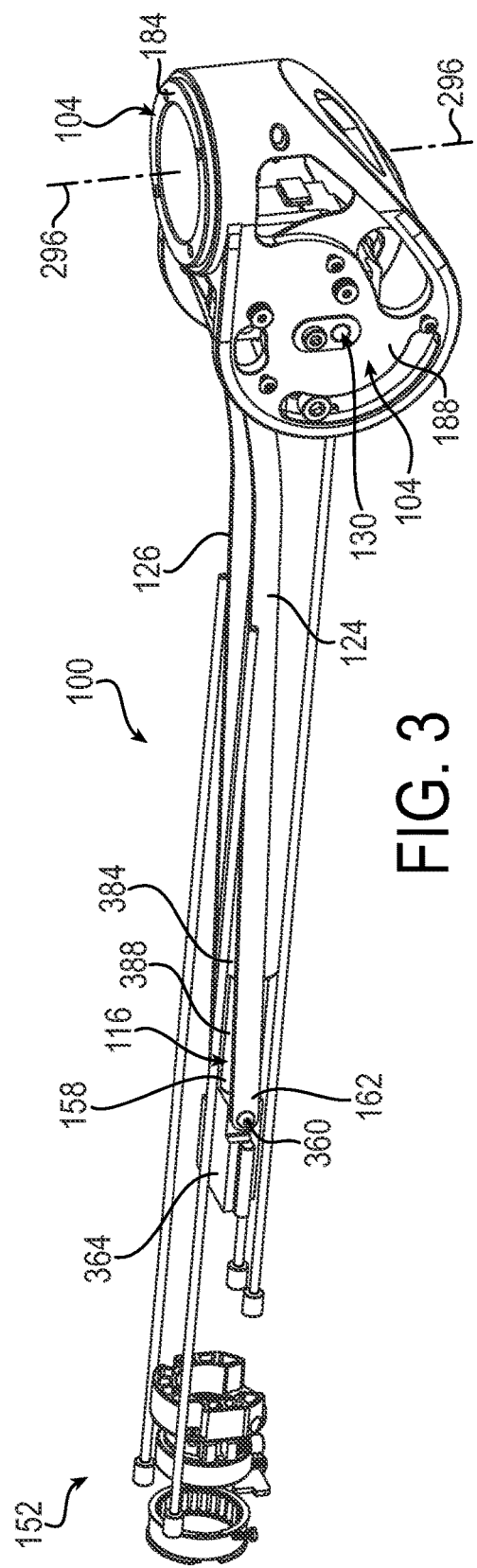

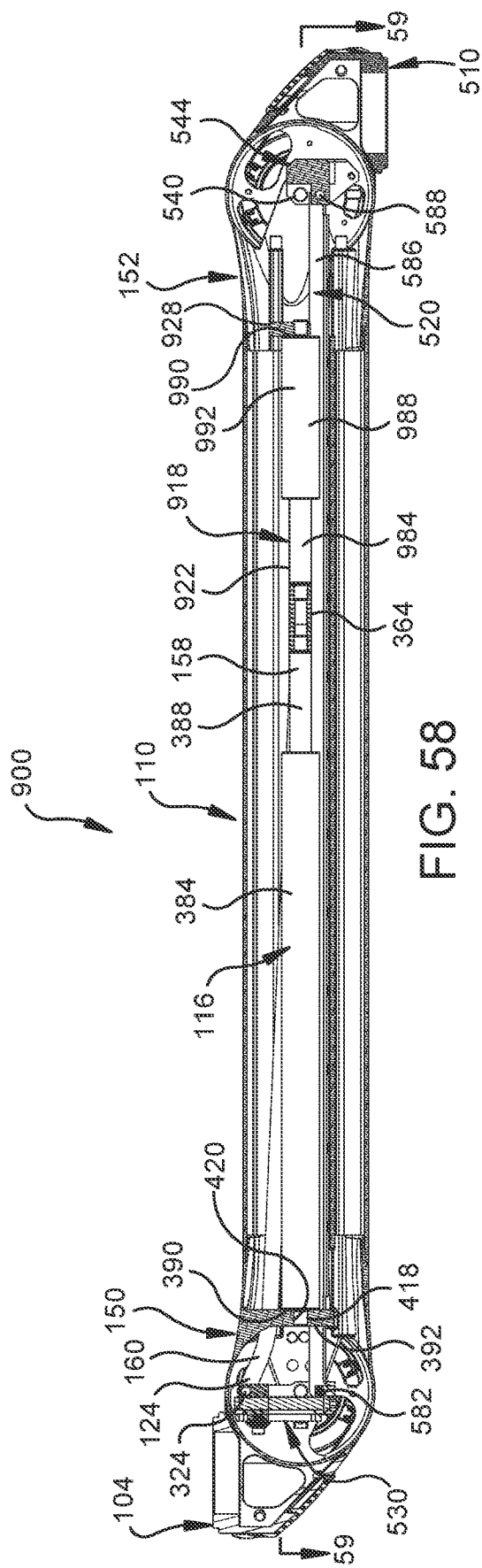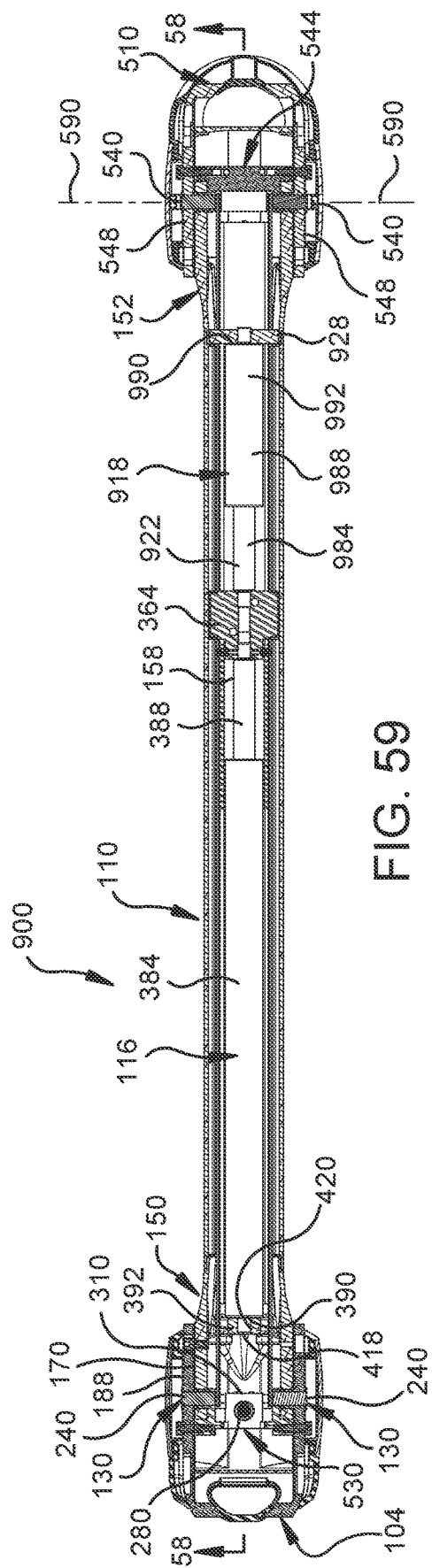

LOAD BALANCING ARM FOR MEDICAL DEVICE SUPPORT SYSTEM

This application claims priority to U.S. Patent Application No. 63/256,713 filed Oct. 18, 2021, which is incorporated herein by reference.

FIELD OF INVENTION

This application relates generally to a load balancing arm for a medical device support system or carry system for use in, for example, a hospital examination room, a clinic, a surgery room or an emergency room, and more particularly to a load balancing arm that improves force transmission and increases load balancing capacity.

BACKGROUND

Medical device support systems, also referred to as suspension systems and carry systems, are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The support systems typically include a central shaft or support column that is suspended from the ceiling or mounted to a wall, one or more generally horizontal extension arms mounted for rotational movement about the shaft, and one or more load balancing arms, also known as counterbalancing arms, that enable positioning of a medical device to a proper orientation relative to for example a patient operating table and healthcare professionals in the operating room. The extension arms and load balancing arms each include a support arm structure or housing, or more generally a support arm.

For load balancing arms in some medical device support systems or carry systems, there is a need to improve the force transmission and increase the load bearing capacity and range of control of the load balancing arm with minimal or no corresponding increase in the size of the load balancing arm. In some applications a load balancing arm may have insufficient capacity to adequately balance a load, whether due to the arm's spring lacking a sufficient counterbalancing effect or due to the arm's inability to otherwise provide a stable and natural handling for the operator. Simply increasing the spring force of the arm's spring may not be practicable as it may require increasing the spring constant and thus increasing the cross sectional area of the spring and consequently the cross sectional area of the load balancing arm. In many health treatment settings, increasing the cross sectional area of the load balancing arm translates into less available space for healthcare personnel, particularly because the load balancing arm may require space for a variety of rotations and pivots for a single medical procedure and/or space to accommodate numerous different medical procedures.

Accordingly, there remains a need for further contributions in this area of technology.

SUMMARY OF INVENTION

The application relates to a load balancing arm for a medical device support system, in which a link connects at its proximal end to a link bearing element and at its distal end to a distal end of a first spring and a proximal end of a second spring, where both of the springs are within a cavity of the load balancing arm and contribute to the counterbalancing biasing forces of the load balancing arm. The inventor has found that a load balancing arm configured in this way improves the force transmission and increases the load bearing capacity of the load balancing arm with minimal or no corresponding increase in the size of the load balancing arm.

According to one aspect of the invention, a load balancing arm for a medical device support system includes a proximal hub including a main bearing element defining a main pivot axis; a link bearing element defining a link pivot axis; a support arm having a proximal end and a distal end, wherein the distal end is configured to support a medical device load and the proximal end is pivotably mounted to the main bearing element for pivotable movement about the main pivot axis; a first spring extending within a cavity of the support arm and mounted to exert a biasing force between the main pivot axis and a distal end of the first spring; a second spring extending within the cavity of the support arm and mounted to exert a biasing force between a proximal end of the second spring and a wall at the distal end of the support arm; and, at least one link having a proximal end pivotably mounted to the link bearing element for pivotable movement about the link pivot axis, and a distal end pivotably mounted to the distal end of the first spring and the proximal end of the second spring such that the biasing forces exerted by the first and second springs are transmitted through the link to the link bearing element thereby to generate a moment about the main pivot axis of the proximal hub that counters a moment generated by the medical device load at the distal end of the support arm.

Embodiments of the invention may include one or more of the following additional features separately or in combination.

The first spring and the second spring may be connected functionally in series.

The first and second springs may be oriented along an axis that extends radially from and perpendicular to the main pivot axis.

The first spring may be configured to expand and contract along a first axis and the second spring may be configured to expand and contract along a second axis, and the first and second axes may coincide with one another.

The biasing force of the first spring may be configured to bias the distal end of the at least one link toward the main pivot axis at the proximal end of the support arm and the biasing force of the second spring may be configured to bias the distal end of the at least one link toward the wall at the distal end of the support arm.

The link pivot axis may be axially spaced from the main pivot axis.

The link bearing element may be an adjustable bearing element, and the link pivot axis may be adjustable axially relative to the main pivot axis.

The first spring may be a compression spring and the second spring may be a tension spring.

The load balancing arm may further include a carriage slide that is slidable relative to the support arm, and the distal end of the link may be pivotably mounted to the distal end of the first spring and the proximal end of the second spring via the carriage slide.

The proximal end of the second spring and the distal end of the first spring may be connected to axially opposite ends of the carriage slide.

The proximal end of the second spring, the carriage slide, and the distal end of the first spring may be configured to move together in unison as the carriage slide moves relative to the support arm.

The carriage slide may be slidable within at least one groove in the support arm.

The groove may be oriented along an axis that extends radially from and perpendicular to the main pivot axis.

The wall may be an internal wall that is supported by and projects inward from a perimeter wall of the support arm that surrounds the first and second springs.

The first and second springs may be gas springs having a cylinder and a rod, and the rod of the first spring and the cylinder of the second spring may be pivotably mounted to the distal end of the at least one link.

The at least one link may comprise a pair of links that straddle the first spring on laterally opposite sides of the first spring.

The support arm may include an intermediate portion between the proximal end and distal end of the support arm, and the intermediate portion may have a relatively narrower height span than the proximal end of the support arm, and the at least one link may have at least one bend that corresponds to the difference in height span between the intermediate portion and the proximal end of the support arm.

The support arm may have an angle of rotation about the main pivot axis of about 30 degrees upward from horizontal to about 85 degrees downward from horizontal.

The load balancing arm may further include a parallel link that is pivotably connected at its proximal end to a pin supported by the proximal hub and at its distal end to a pin supported by a distal hub pivotably connected to the distal end of the support arm.

The parallel link may include a pair of laterally spaced side walls that straddle a vertically lower portion of the first and second springs on laterally opposite sides of the first and second springs.

The parallel link may include a pair of laterally spaced side walls that straddle the at least one link on laterally opposite sides of the at least one link over at least a portion of a pivotable range of the load adjustment arm.

According to another aspect of the invention, a load balancing arm for a medical device support system includes a central shaft; an extension arm mounted to the central shaft for rotational movement about the shaft; and a load balancing arm including: a proximal hub including a main bearing element defining a main pivot axis; a counterbalancing bearing element defining a counterbalancing pivot axis; a support arm having a proximal end and a distal end, wherein the distal end is configured to support a medical device load and the proximal end is pivotably mounted to the main bearing element for pivotable movement about the main pivot axis; a first spring extending within a cavity of the support arm and mounted to exert a biasing force between the main pivot axis and a distal end of the first spring; a second spring extending within the cavity of the support arm and mounted to exert a biasing force between a proximal end of the second spring and a wall at the distal end of the support arm; and, at least one link having a proximal end pivotably mounted to the counterbalancing bearing element for pivotable movement about the counterbalancing pivot axis, and a distal end pivotably mounted to the distal end of the first spring and the proximal end of the second spring such that the biasing forces exerted by the first and second springs are transmitted through the link to the counterbalancing bearing element thereby to generate a moment about the main pivot axis of the proximal hub that counters a moment generated by the medical device load at the distal end of the support arm.

Embodiments of the invention may include one or more of the following additional features separately or in combination.

The counterbalancing bearing element may be an adjustable bearing element, and the counterbalancing pivot axis may be adjustable relative to the main pivot axis.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 2 is a side perspective view of a load balancing arm in accordance with an embodiment of the invention.

FIG. 3 is a view similar to FIG. 2 with a support arm structure removed to show internal components of the load balancing arm.

FIG. 58 is a side cross section view of the FIG. 55 load balancing arm as viewed from the plane 58-58 in FIG. 59, as though the load balancing arm in FIG. 59 were whole.

FIG. 59 is a top cross section side view of the FIG. 55 load balancing arm as viewed from the plane 59-59 in FIG. 58, as though the load balancing arm in FIG. 58 were whole.

DETAILED DESCRIPTION

Figure 1:
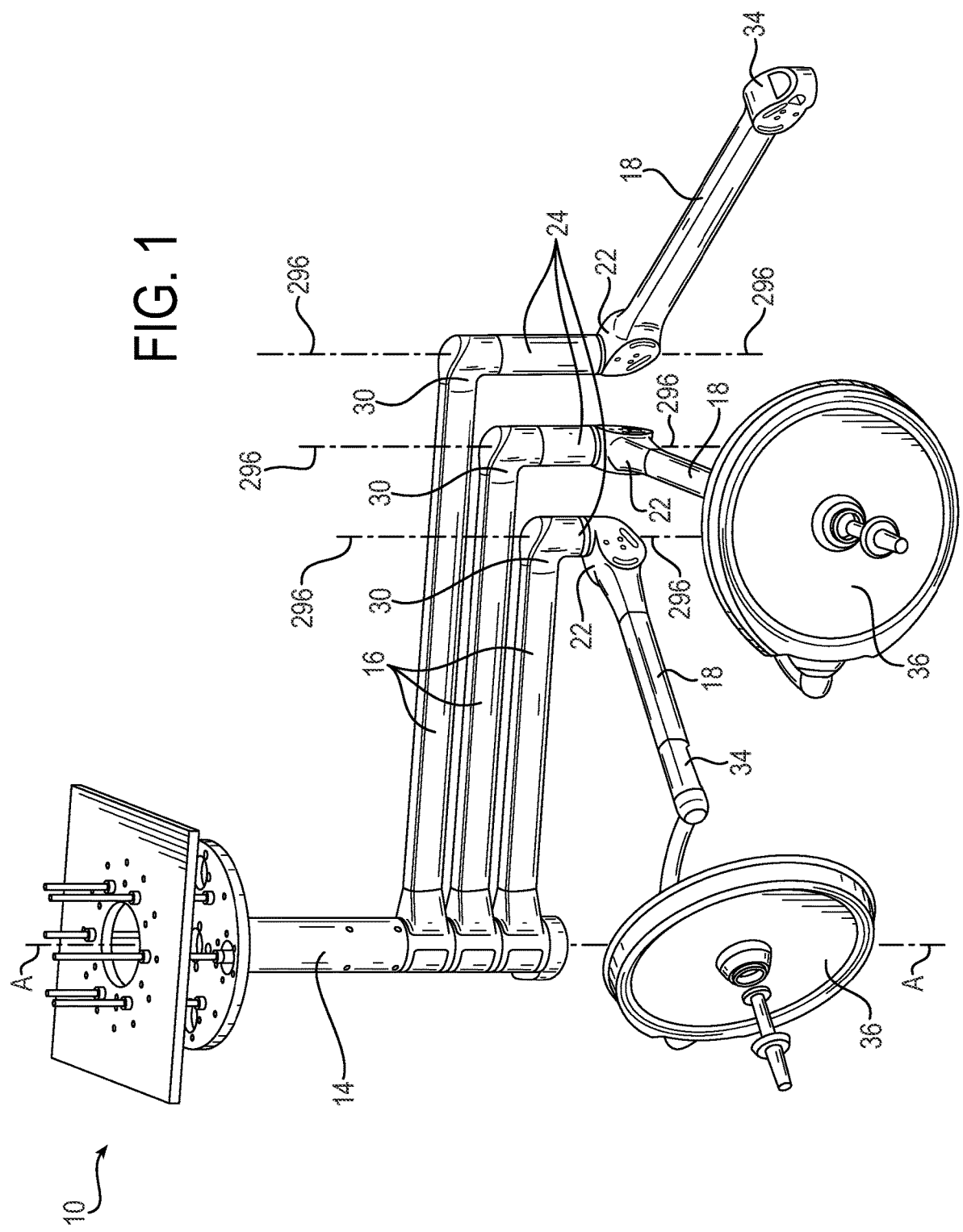
FIG. 1 is a perspective view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIG. 1 shows a medical device support system 10 in accordance with an embodiment of the invention. The medical device support system 10 includes a central shaft or support column 14 that is suspended from the ceiling, and three generally horizontal extension arms 16 mounted to the shaft 14 for rotational movement about the shaft 14. The central shaft 14 could be mounted to a wall or stand rather than the ceiling. Three load balancing arms 18, which are also referred to as counterbalancing arms, are mounted to the respective extension arms 16. The extension arms 16 and load balancing arms 18 each include a support arm structure or housing, or more generally a support arm. In the FIG. 1 embodiment, a proximal hub 22 of the load balancing arm 18 includes a support structure 24, for example the illustrative drop tube 24, that is rotatably connectable to a receptacle at the distal end 30 of the extension arm 16. The distal end of each load balancing arm 18 is configured with a suitable support hub 34 to support a medical device load 36. The medical device load 36 may include a surgical light as shown, or a supply console, a patient monitor, a camera detector head, a medical instrument, a ventilator system, a suction device, among others. A control console, if provided, may provide controls for navigation of a medical instrument that is either coupled to or remote from the load balancing arm 18. The load balancing arm 18 enables positioning of the medical device 36 to a proper orientation relative to for example a patient operating table and healthcare professionals in the operating room.

Figure 11:
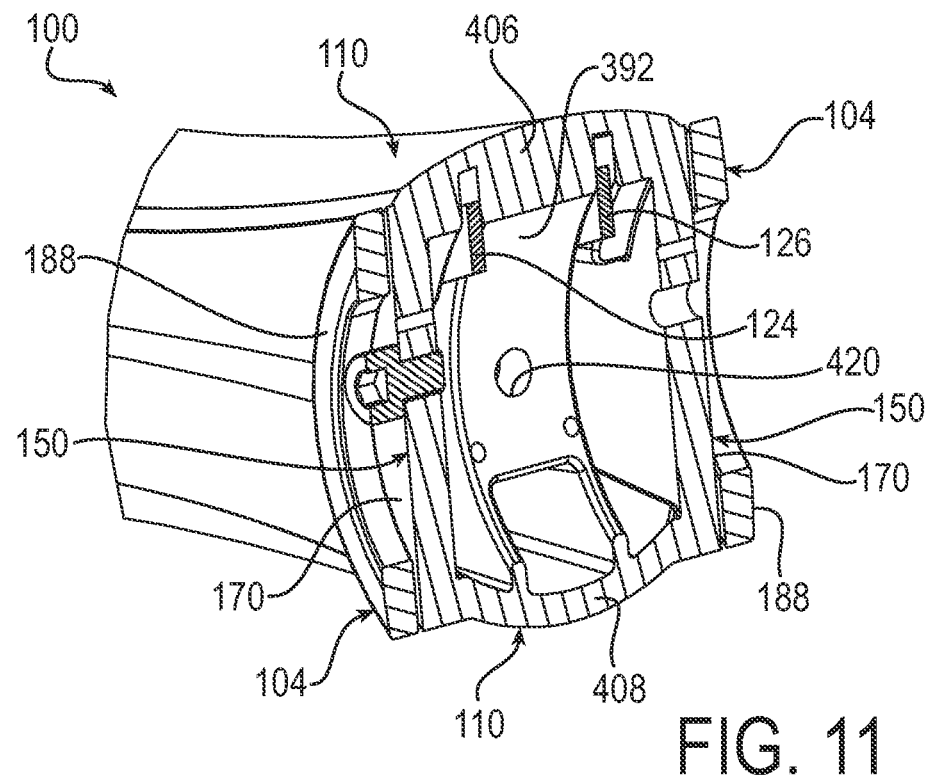
FIG. 11 is a cross section view of the FIG. 2 load balancing arm as viewed from the plane 11-11 in FIG. 4.
Figure 12:
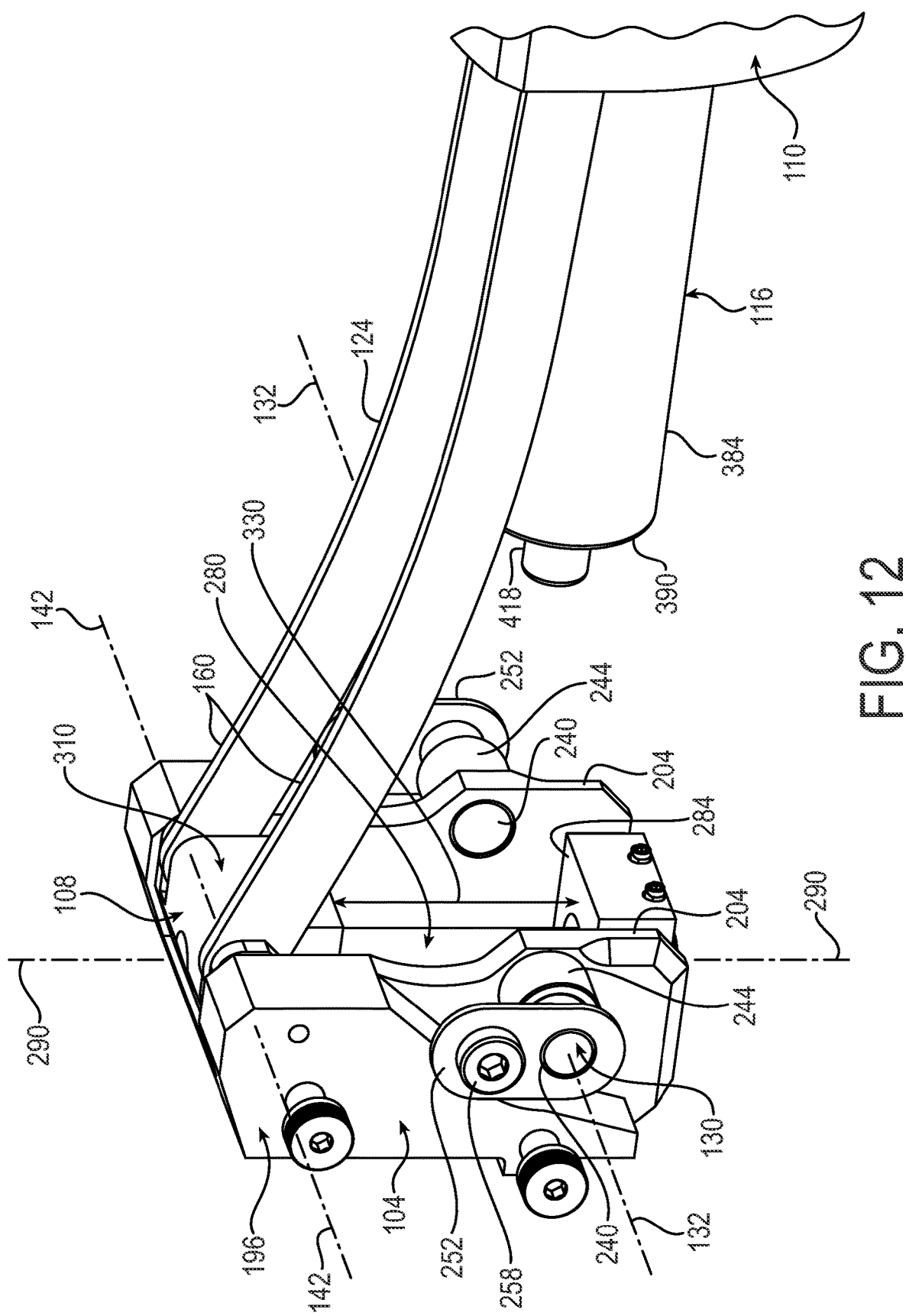
FIG. 12 is a perspective view of a proximal end of the load balancing arm, showing internal components of the load balancing arm.

Turning now to FIGS. 2-20, there is shown a load balancing arm 100 of the medical device support system 10 in accordance with an embodiment of the invention. The load balancing arm 100 includes a proximal hub 104, an adjustable bearing element 108, a support arm 110, a spring 116, and one or more links, two such links 124, 126 in the illustrative embodiment, as shown in FIGS. 3 and 12. The proximal hub 104 may include a support structure 24 such as the drop tube 24 (see FIG. 1). The proximal hub 104 includes a main bearing element 130 that defines a main pivot axis 132. The adjustable bearing element 108 defines an adjustable pivot axis 142 that is adjustable relative to the main pivot axis 132. The support arm 110 has a proximal end 150 and a distal end 152. The distal end 152 is configured to support a medical device load 36 (see FIG. 1) and the proximal end 150 is pivotably mounted to the main bearing element 130 for pivotable movement about the main pivot axis 132. Pivotable movement about the main pivot axis 132 raises and lowers the height of the medical device load 36 at the distal end 152.

The spring 116 extends within a cavity 154 of the support arm 110 and is mounted to exert a biasing force between the main pivot axis 132 and a distal end 158 of the spring 116. The links 124, 126 each have a proximal end 160 and a distal end 162. The proximal end 160 is pivotably mounted to the adjustable bearing element 108 for pivotable movement about the adjustable pivot axis 142. The distal ends 162 of the links 124, 126 are pivotably mounted to the distal end 158 of the spring 116 such that the biasing force exerted by the spring 116 is transmitted through the links 124, 126 to the adjustable bearing element 108 thereby to generate a moment about the main pivot axis 132 of the proximal hub 104 that counters a moment generated by the medical device load 36 at the distal end 152 of the support arm 110, thereby balancing the medical device load 36.

Thus, in the load balancing arm 100 according to the present embodiment, the links 124, 126 connect at their proximal ends 160 to an adjustment bearing element 108 and at their distal ends 162 to the distal end 158 of the spring 116. As will be described in greater detail below, the attachment at the distal end 158 of the spring 116 allows for a relatively longer link than if connected to the proximal end of the spring 116. This allows for a better force transmission and less spring travel resulting in a more balanced load balancing arm 100 throughout the pivotable range of travel of the arm 100.

Figure 4:
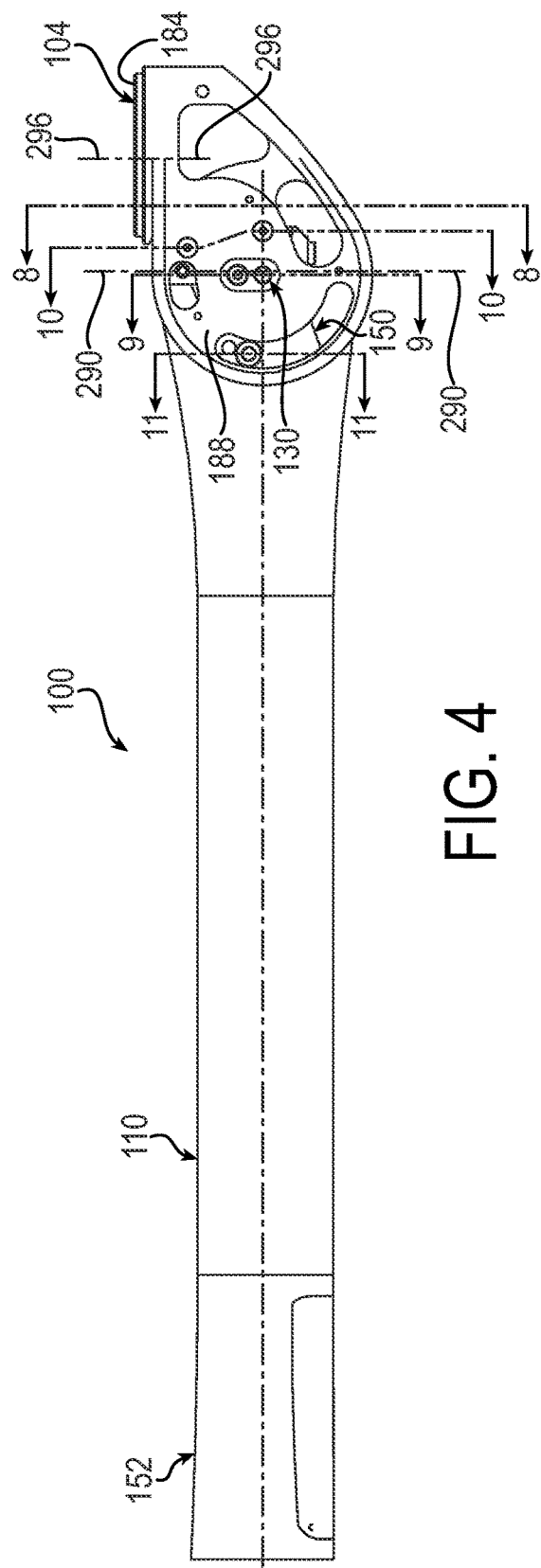
FIG. 4 is a side view of the FIG. 2 load balancing arm.
Figure 5:
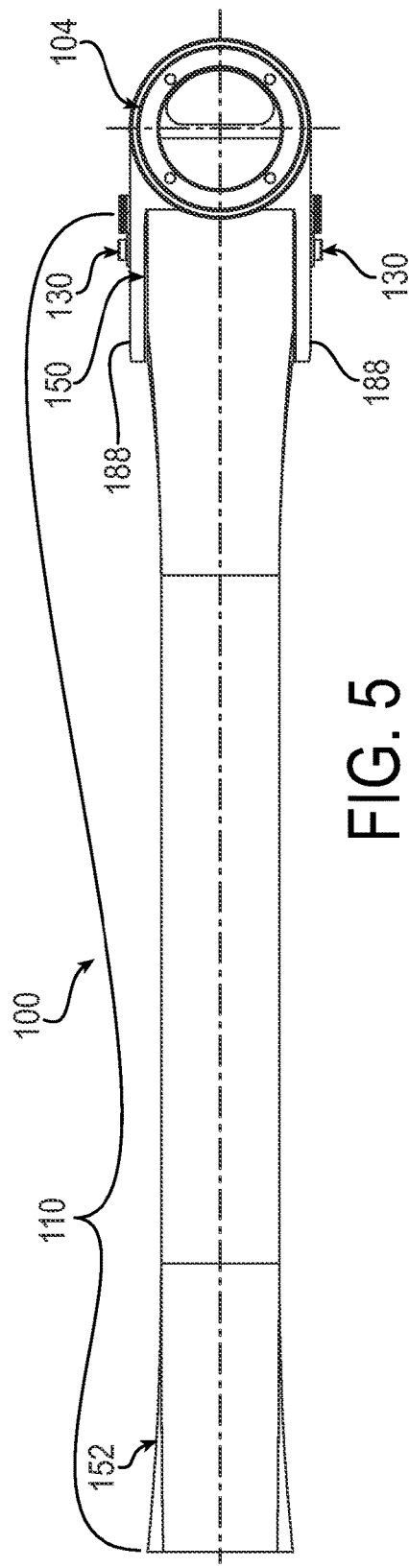
FIG. 5 is a top view of the FIG. 2 load balancing arm.
Figure 6:
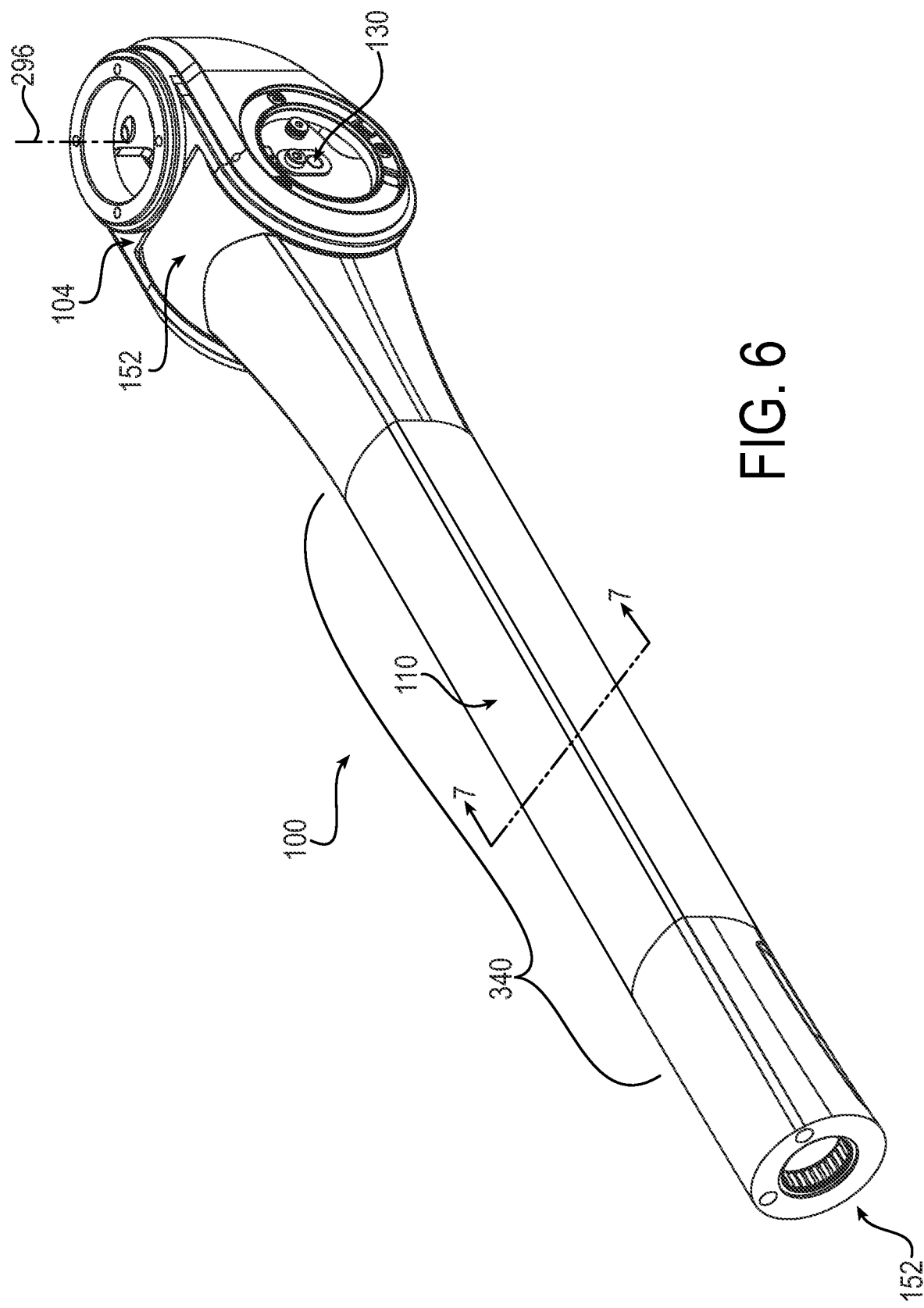
FIG. 6 is an end perspective view of the FIG. 2 load balancing arm, showing at a distal end thereof a connection receptacle for receipt of a medical device.

Reference is now made to FIGS. 2-6 and 15-20 which show greater detail of the support arm 110, the proximal hub 104, and the interface between the support arm 110 and proximal hub 104. As shown in FIGS. 2, 5 and 6, the proximal end 150 of the support arm 110 has a relatively smaller width than the proximal hub 104 and fits within the proximal hub 104. In the illustrated embodiment, the proximal end 150 of the support arm 110 includes a pair of vertically oriented laterally spaced protrusions or tongue portions 170 and a circular portion 178 substantially surrounding the tongue portions 170. As shown in FIGS. 3 and 4, the proximal hub 104 includes a mounting surface 184 for mounting the proximal hub 104 and thus the load balancing arm 100 to, for example, the distal end of an extension arm 16. The proximal hub 104 includes a pair of vertically oriented side walls 188 alongside which the tongue portions 170 of the support arm 110 slide during adjusting of the support arm 110. In side profile, the side walls 188 have a circular shape that corresponds in diameter to the circular portion 178 of the proximal end 150 of the support arm 110.

Figure 9:
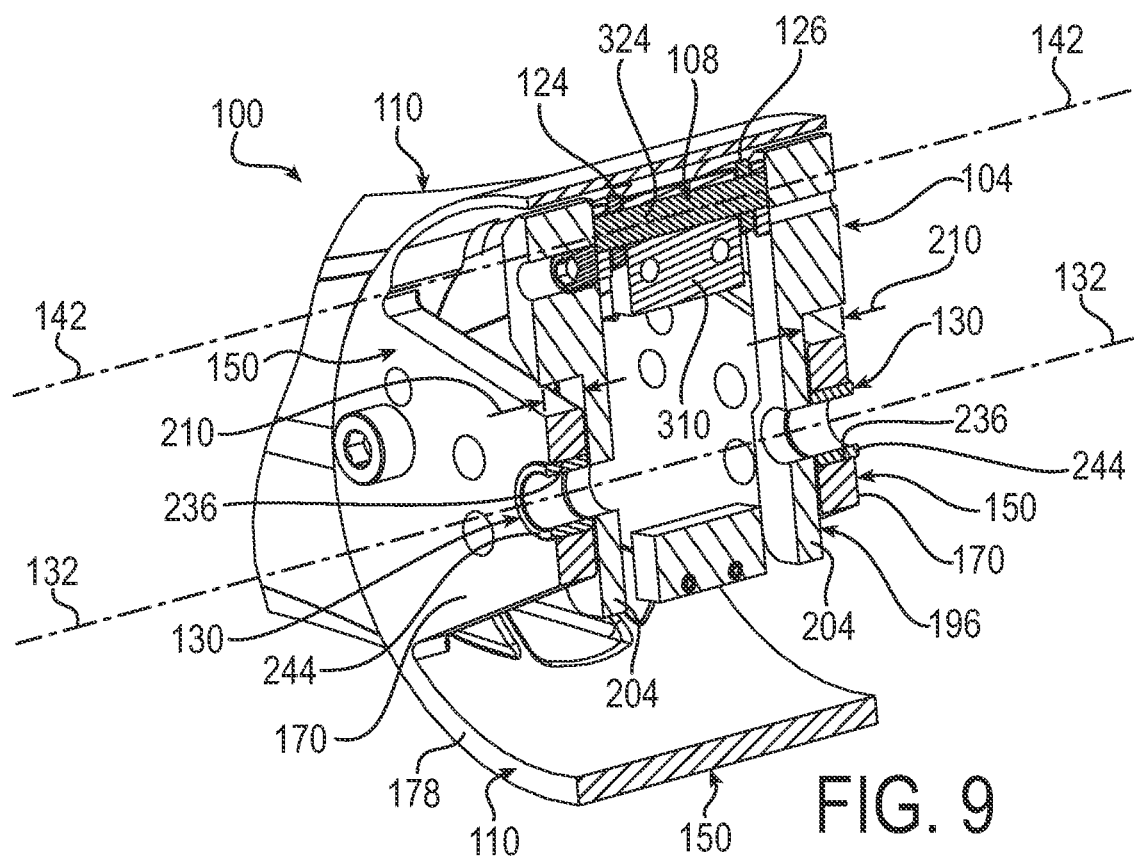
FIG. 9 is a cross section view of the FIG. 2 load balancing arm as viewed from the plane 9-9 in FIG. 4, without the proximal hub to show internal components of the load balancing arm.
Figure 10:
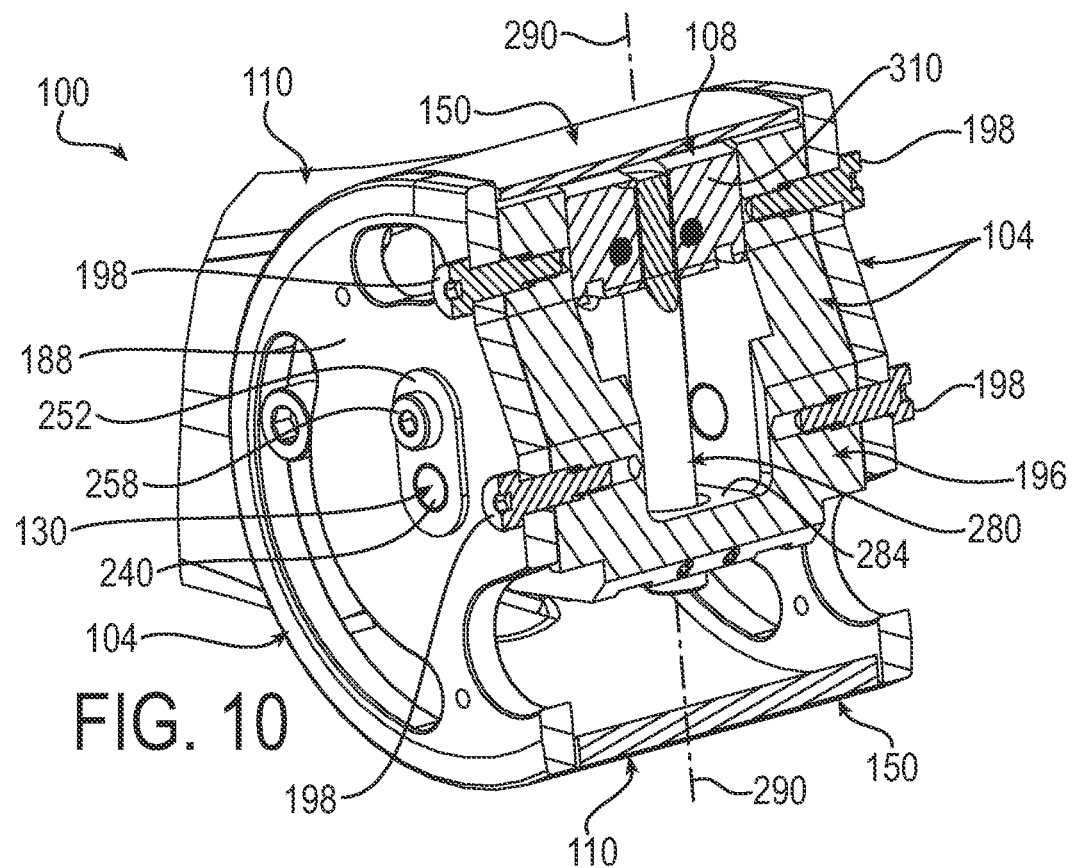
FIG. 10 is a cross section view of the FIG. 2 load balancing arm as viewed from the plane 10-10 in FIG. 4.
Figure 13:
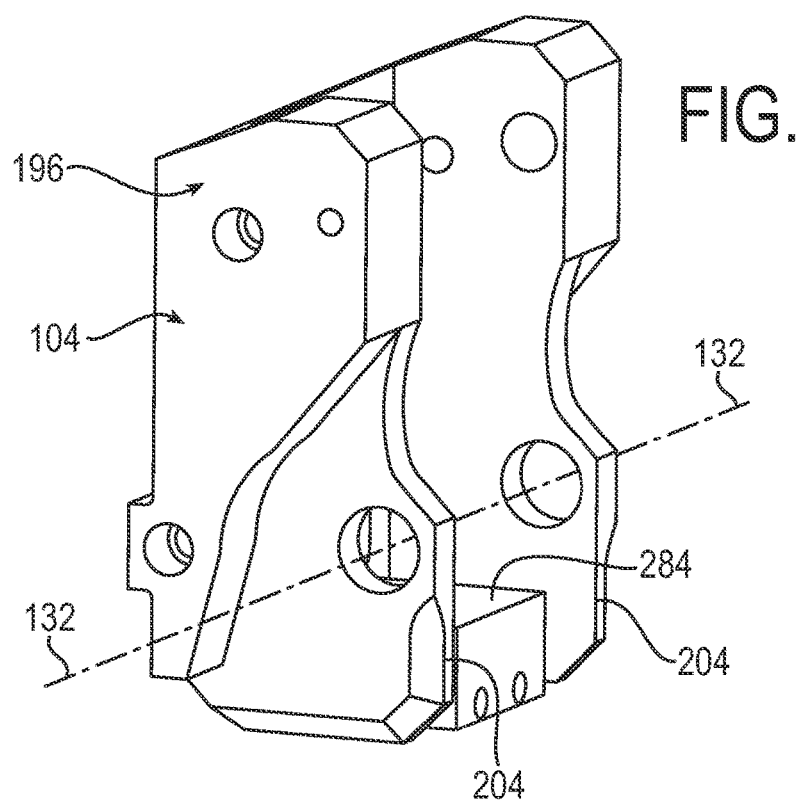
FIG. 13 is a side perspective view of a load adjustment base of a proximal hub of the FIG. 2 load balancing arm.
Figure 14:
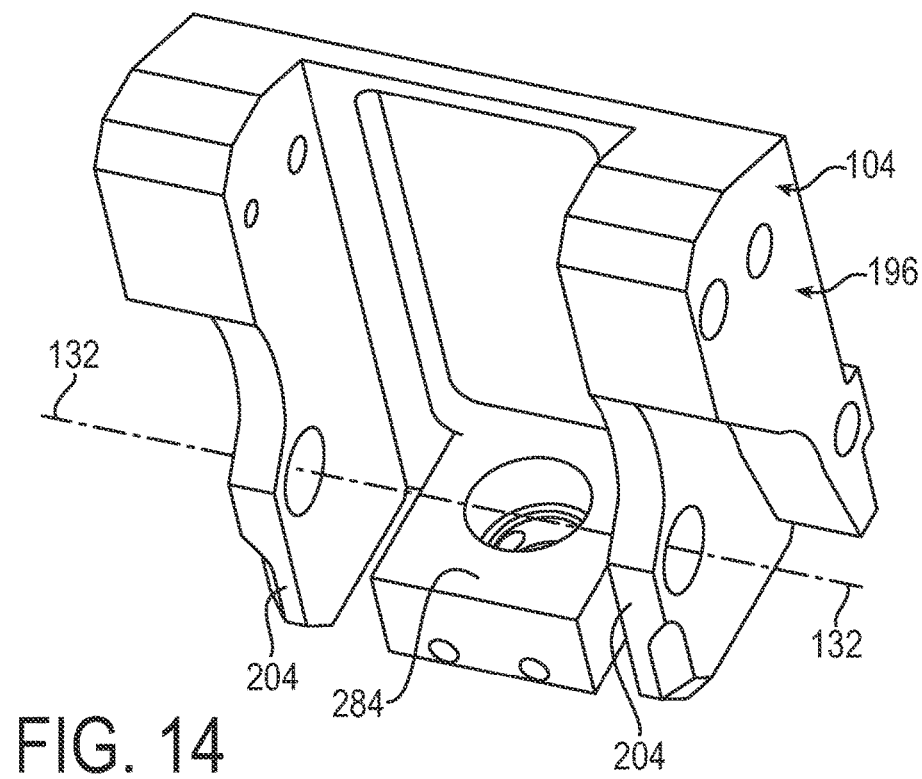
FIG. 14 is a top perspective view of the load adjustment base of the proximal hub of the FIG. 2 load balancing arm.

The proximal hub 104 also includes a load adjustment base 196 that extends width-wise between the pair of vertically oriented side walls 188 and that, as shown in FIGS. 15-20, extends vertically downward from a location just below the vertically uppermost portion of the circular portion 178 of the proximal end 150 of the support arm 110 downward approximately three fourths the distance across the circular portion 178. Details of one example of the load adjustment base 196 are shown in FIGS. 9, 10, 12-14 and 18-20. As shown in FIG. 10, the load adjustment base 196 may be fastened to the side walls 188 by fasteners 198. As shown in FIGS. 12-14, the load adjustment base 196 has a pair of laterally spaced flanges 204 that are recessed inward from the outer width of the load adjustment base 196. Referring to FIG. 9, the recessed flanges 204 form respective gaps 210 with the side walls 188 within which the tongue portions 170 of the support arm 110 are received. As shown in FIGS. 9, 12 and 18-20, the tongue portions 170 of the proximal end 150 of the support arm 110 have through holes 236 and the main bearing element 130 of the proximal hub 104 includes a pair of laterally spaced pins 240. The central axis of these pins 240 defines or coincides with the main pivot axis 132. The through holes 236 receive the pins 240 thereby to pivotably mount the proximal end 150 of the support arm 110 to the main bearing element 130 of the proximal hub 104 for pivotable movement of the support arm 110 about the main pivot axis 132.

Figure 8:
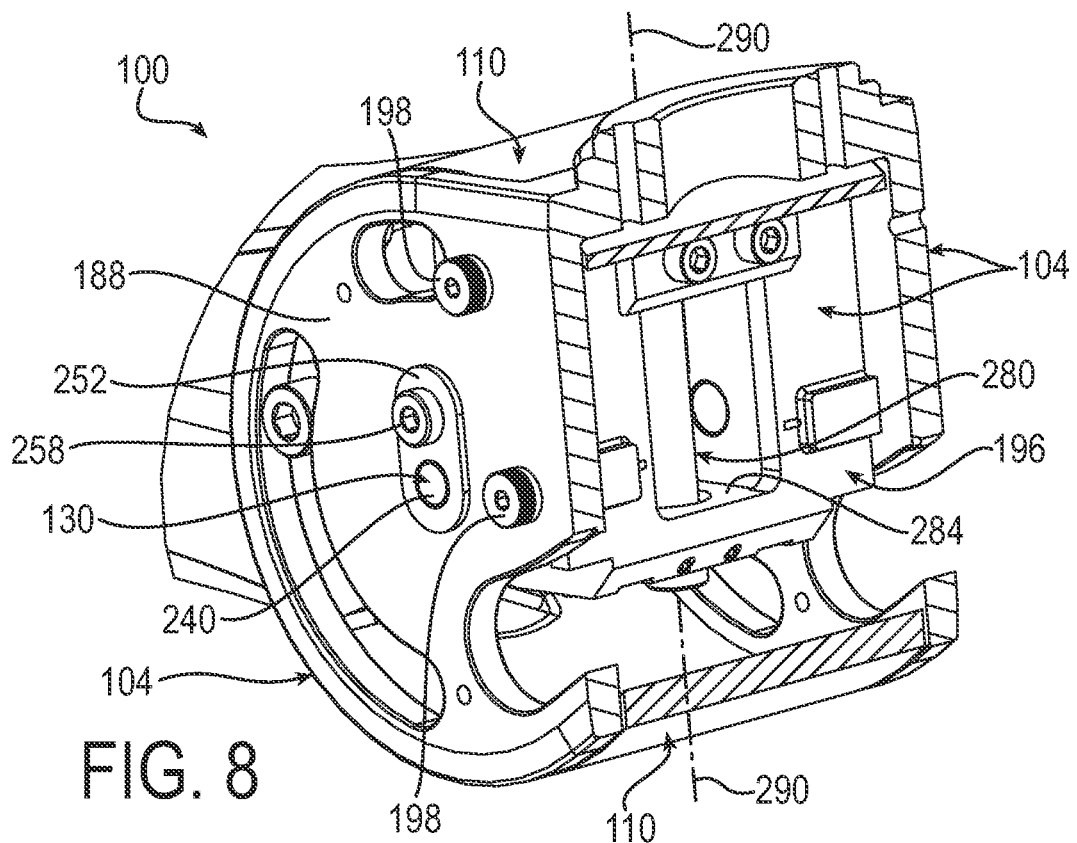
FIG. 8 is a cross section view of the FIG. 2 load balancing arm as viewed from the plane 8-8 in FIG. 4.

In the illustrative embodiment, bushings 244 are provided on the pins 240 to promote smooth pivotable operation and serviceability. As shown in FIGS. 8, 10 and 12, the pins 240 are fixedly connected, for example by welding, to a retainer plate 252, which, in turn, is fastened to the side walls 188 of the proximal hub 104 by fasteners 258.

As shown in FIGS. 8 and 10, a load adjustment screw 280 is rotatably mounted in a bottom wall 284 of the load adjustment base 196. The load adjustment screw 280 is fixed in a vertical orientation in the proximal hub 104 and rotates about its own central axis 290. Referring to FIGS. 1-4 and 6, in the present embodiment, the axis 290 of the load adjustment screw 280 is parallel to an axis 296 of rotation of the load balancing arm 100 extending centrally through the support structure 24 and perpendicular to horizontal. As shown in FIGS. 9 and 12, the adjustable bearing element 108 includes a load adjustment nut 310 that threadably engages the load adjustment screw 280 to adjust the adjustable pivot axis 142 relative to the main pivot axis 132. The load adjustment nut 310 moves in the vertical direction as the load adjustment screw 280 is rotated, which vertical movement adjusts the adjustable pivot axis 142 relative to the main pivot axis 132. As shown in FIG. 9, the adjustable bearing element 108 includes a pin 324 that is carried by the load adjustment nut 310. The central axis of the pin 324 defines or coincides with the adjustable pivot axis 142. As shown in FIGS. 9 and 12, the proximal ends 160 of the links 124, 126 are pivotably mounted to the pin 324 at respective opposite ends of the pin 324. The adjustable pivot axis 142 is adjustable relative to the main pivot axis 132 over a range of adjustment 330, defined in the illustrative embodiment by the uppermost and lowermost vertical position of the load adjustment nut 310.

The vertical movement of the load adjustment nut 310 adjusts the load capacity of the load balancing arm 100. As will be appreciated, the distance between the adjustable pivot axis 142 of the pin 324 and the main pivot axis 132 of the proximal hub 104 provides the mechanical advantage, or moment, that allows the load balancing arm 100 to balance a medical device load 36 at the distal end 152 of the arm 100.

Figure 17:
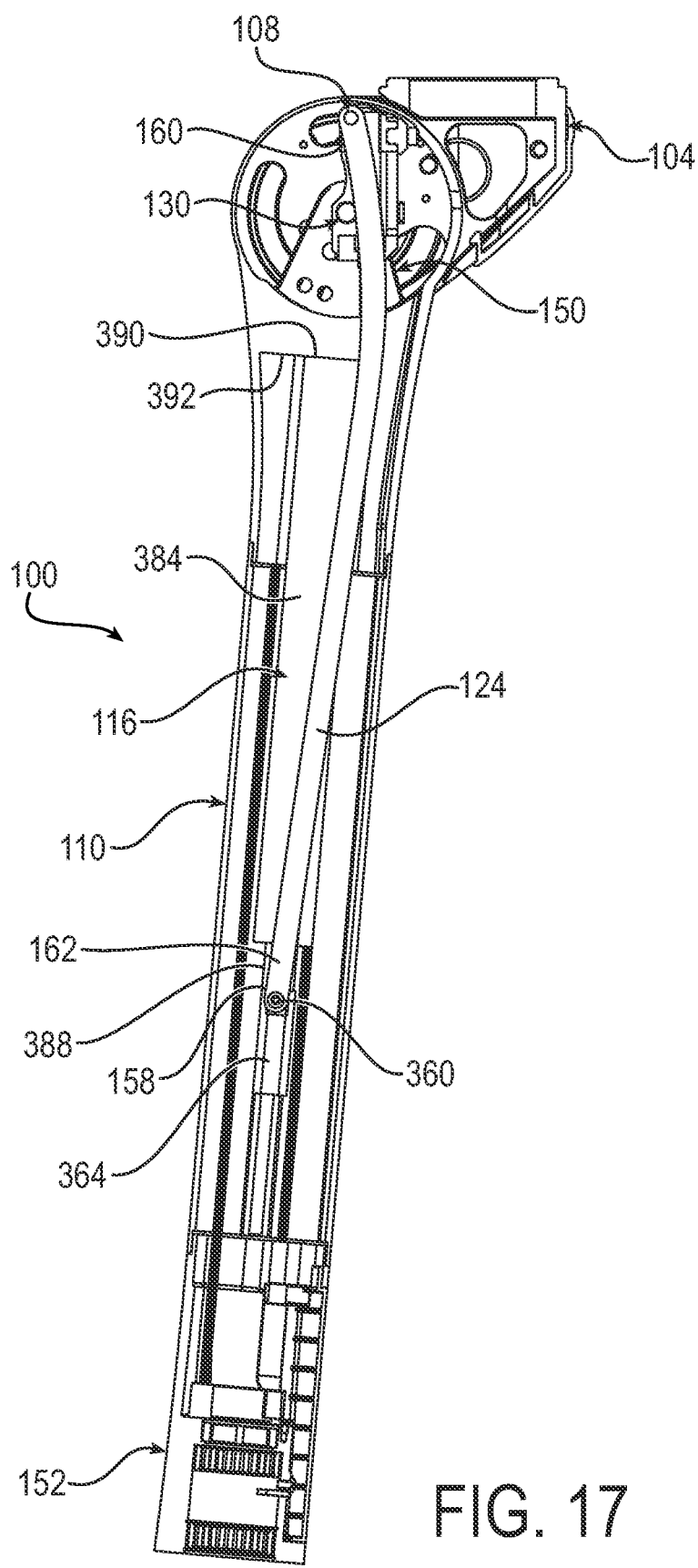
FIG. 17 is a side cross section view of the FIG. 2 load balancing arm in a position downward from horizontal, showing internal components of the load balancing arm.
Figure 20:
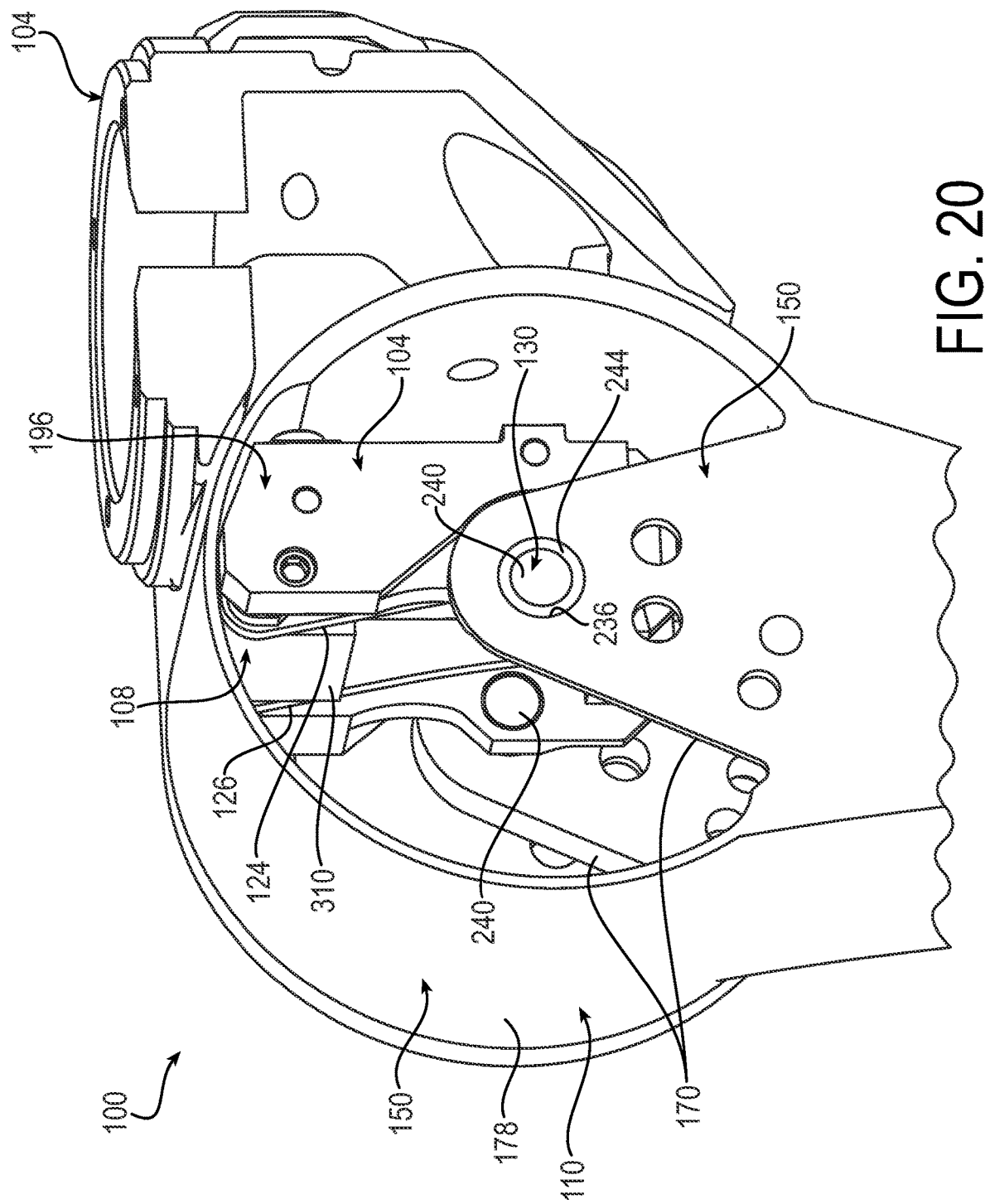
FIG. 20 is a perspective view of the proximal end of the FIG. 2 load balancing arm in a position downward from horizontal, with a cover removed to show internal components of the load balancing arm.

With reference to FIG. 12, the laterally spaced pins 240 split the main pivot axis 132 thereby enabling the adjustable bearing element 108 to be moved vertically across the main pivot axis 132 into a position between the laterally spaced pins 240. Accordingly, the adjustable bearing element 108 and the proximal ends 160 of the respective pair of links 124, 126 are movable between the pair of pins 240 over a portion of the range of adjustment 330. As will be appreciated, this provides greater adjustment range in the proximal ends 160 of the links 124, 126 pivotably mounted to the pin 324 of the adjustable bearing element 108 than if the pins 240 were a single pin member and the main pivot axis 132 was not split. As shown in FIGS. 17 and 20, the split main pivot axis 132, i.e. laterally spaced pins 240, also enables the proximal ends 160 of the links 124, 126 to move between the pins 240 for example when the load balancing arm 100 is pivoted to lower positions.

Referring to FIG. 4, the adjustable pivot axis 142 of the adjustable bearing element 108 is horizontally offset from the main pivot axis 132 of the main bearing element 130 in a direction toward the portion of the proximal hub 104 that includes the support structure 24, in the illustrative embodiment toward the axis 296 of rotation of the load balancing arm 100 extending centrally through the support structure 24 and perpendicular to horizontal. In FIG. 4, the offset is the gap between the plane 9-9 and the axis 290. This offset allows for better balancing of the spring arm when a lighthead or other medical device is attached. It also slightly changes the dynamics of the load balancing arm 100 so that when above horizontal there is slightly more mechanical advantage about the main pivot axis 132 and when below horizontal there is slightly less mechanical advantage about the main pivot axis 132. As such, this allows the load balancing arm 100 to compensate for the spring force increasing as the arm 100 is moved to lower vertical positions, for example.

Turning now to FIGS. 6, 9 and 15-17, the support arm 110 includes an intermediate portion 340 between the proximal end 150 and distal end 152 of the support arm 110. The intermediate portion 340 has a relatively narrower height span than the circular portion 178 of the proximal end 150 of the support arm 110. The links 124, 126 (only link 124 is in view in FIGS. 15-17) have at least one bend that corresponds to the difference in height span between the intermediate portion 340 and the circular portion 178 of the proximal end 150 of the support arm 110. In the illustrative embodiment, the links 124, 126 have one bend and consequently have a J-shape in side view. Other shapes such as S-shape (two bends) are also contemplated. The bend in the links 124, 126 aids in the load balancing arm 100 having a smaller size and lower overall cross section profile than if the links 124, 126 were straight. The smaller size and lower overall cross section profile make the load balancing arm 100 less obstructive in the operating room and improve the laminar airflow around the surface of the load balancing arm 100.

Figure 7:
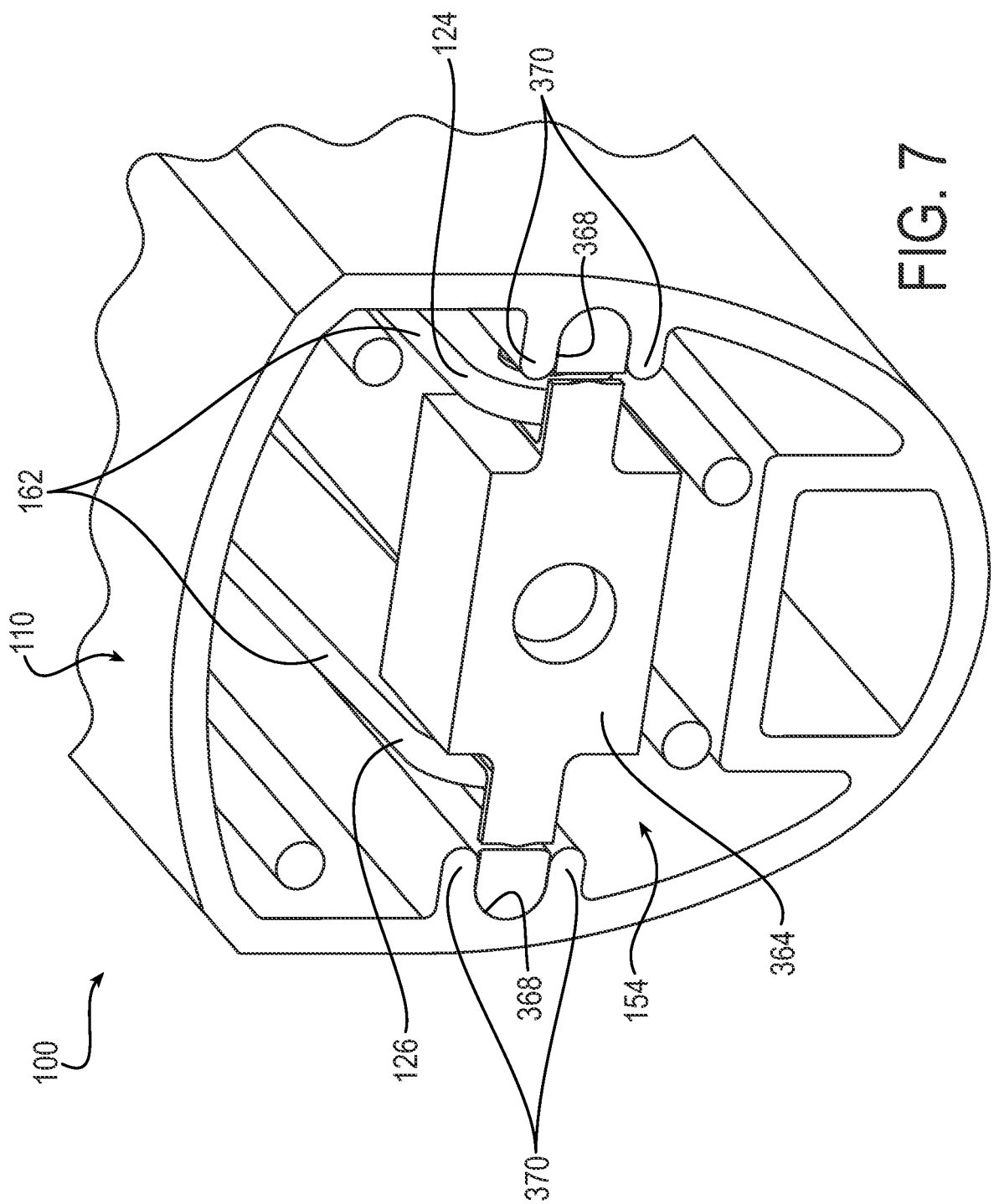
FIG. 7 is cross section view of the FIG. 2 load balancing arm as viewed from the plane 7-7 in FIG. 6.

The distal ends 162 of the links 124, 126 are pivotably mounted to the distal end 158 of the spring 116 via a carriage slide 364 that is slidable relative to the support arm 110. The pivotable connection may be facilitated by, for example, a pin 360 mounted within the carriage slide 364. As shown in FIG. 7, the carriage slide 364 is slidable within at least one groove 368 in the support arm 110, wherein in the illustrative embodiment there are two such grooves 368 at laterally opposite sides of the support arm 110. The grooves 368 are oriented along an axis that extends radially from and perpendicular to the main pivot axis 132. The grooves 368 are formed by parallel ribs 370 in the inward facing walls of the support arm 110. The ribs 370, along with a box shape member in the lower portion of the support arm 110, also serve as stiffening members.

The spring 116 of the load balancing arm 100 may be any type of counterbalancing member, and in the illustrative embodiment is a compression gas spring 116. Like the grooves 368, the spring 116 is oriented along an axis that extends radially from and perpendicular to the main pivot axis 132. The spring 116 has a cylinder 384 and a rod 388. Referring to FIGS. 11, 12 and 15-17, the cylinder 384 has a proximal end wall 390 that is coupled to a vertical beam 392 of the support arm 110. As shown in FIG. 11, the vertical beam 392 extends from a top wall 406 to a bottom wall 408 of the support arm 110 and is sufficiently narrow that the links 124, 126 straddle the vertical beam 392 on opposite lateral sides thereof throughout the pivotable range of the load balancing arm 100. The proximal end wall 390 of the cylinder 384 may be coupled to the vertical beam 392 in any suitable manner, for example as by a protrusion 418, shown in FIG. 12, that fits within an opening 420 in the vertical beam 392, shown in FIG. 11. The rod 388 is pivotably mounted to the distal ends 162 of the links 124, 126 via the pin 360 of the afore described carriage slide 364. In operation, the links 124, 126 straddle the spring 116 on laterally opposite sides of the spring 116 throughout the pivotable range of the load balancing arm 100.

Figure 15:
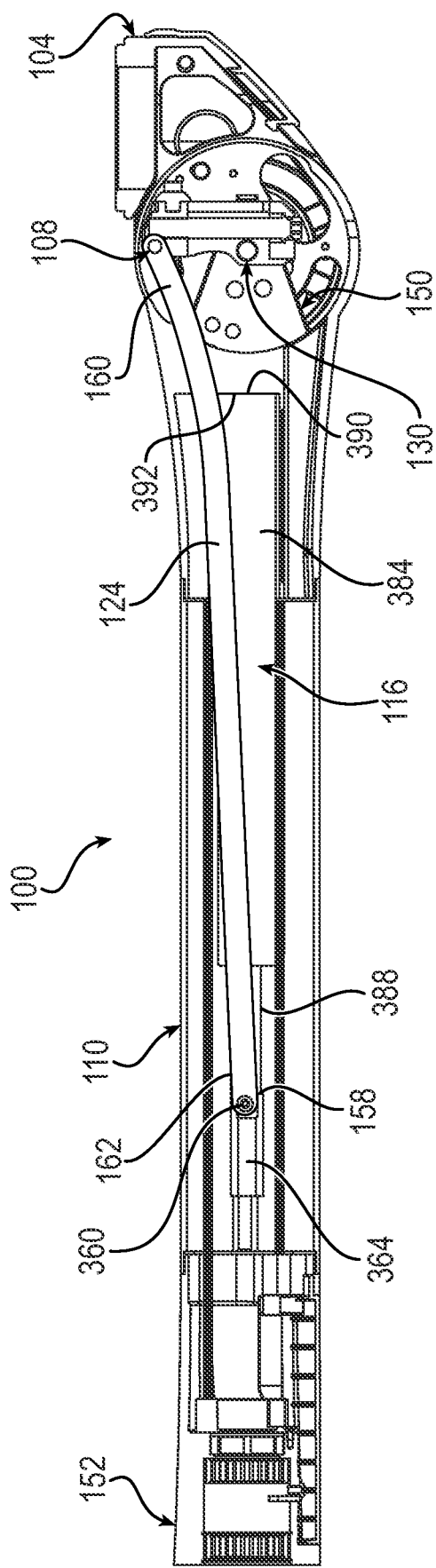
FIG. 15 is a side cross section view of the FIG. 2 load balancing arm in a substantially horizontal position, showing internal components of the load balancing arm.
Figure 16:
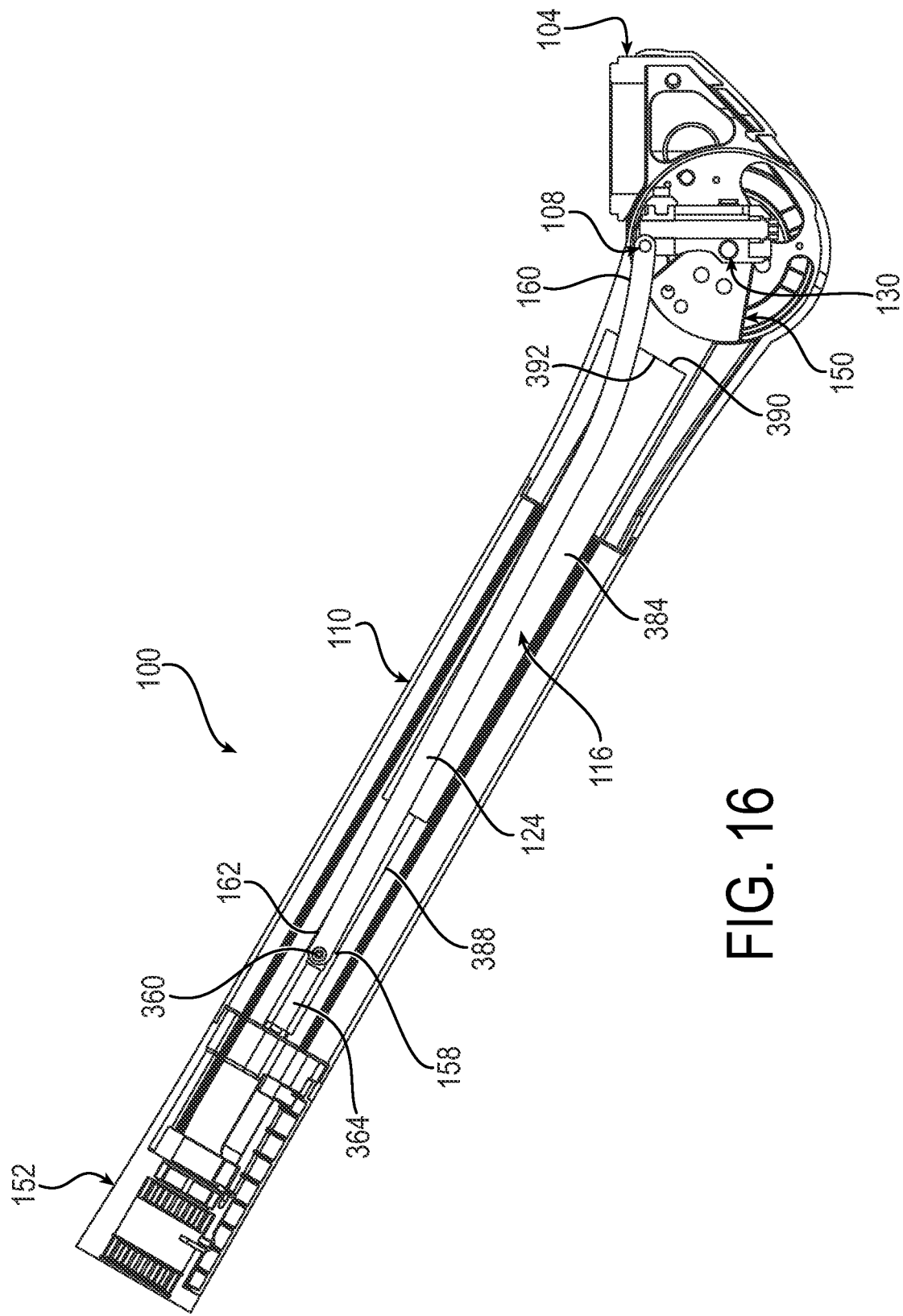
FIG. 16 is a side cross section view of the FIG. 2 load balancing arm in a position upward from horizontal, showing internal components of the load balancing arm.
Figure 18:
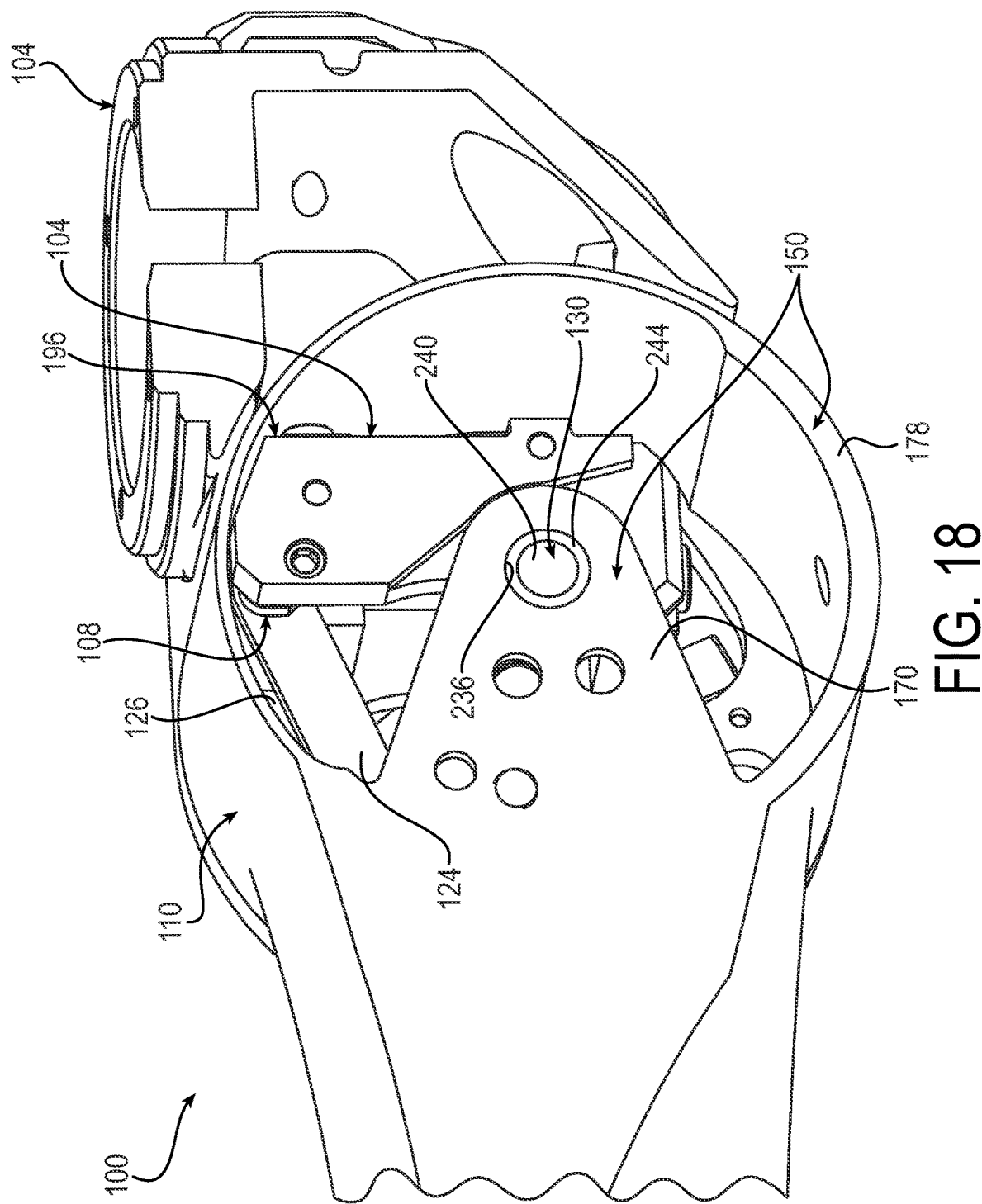
FIG. 18 is a perspective view of the proximal end of the FIG. 2 load balancing arm in a substantially horizontal position, with a cover removed to show internal components of the load balancing arm.
Figure 19:
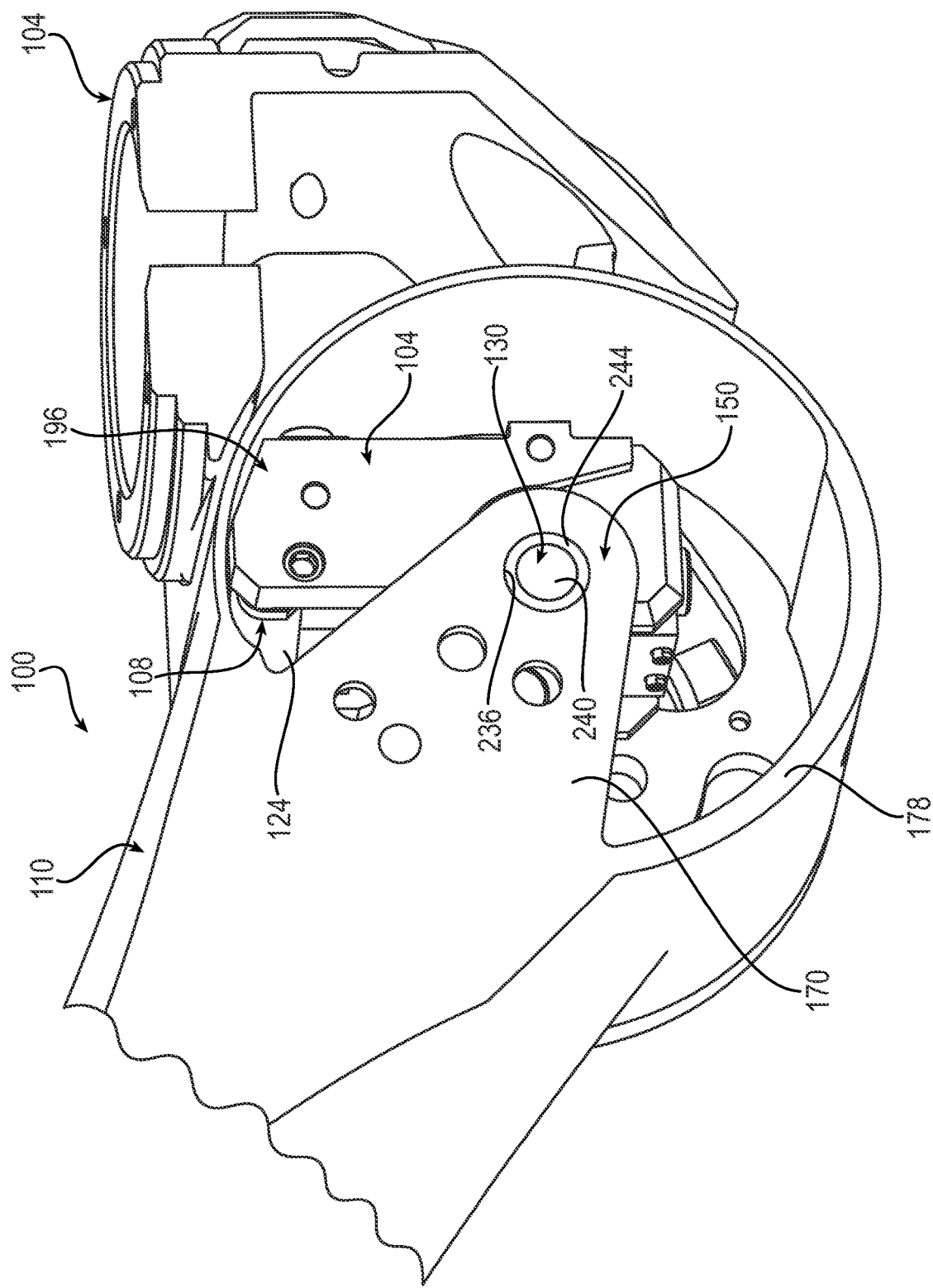
FIG. 19 is a perspective view of the proximal end of the FIG. 2 load balancing arm in a position upward from horizontal, with a cover removed to show internal components of the load balancing arm.

Reference is now made to FIGS. 15-17, which show the load balancing arm 100 in three different vertical positions, and FIGS. 18-20, which show the links 124, 126 and the proximal end 150 of the support arm 110 relative to the proximal hub 104 in the three respective vertical positions. The links 124, 126 are shown adjusted to their maximum height in FIGS. 15-20, thereby maximizing the moment, or mechanical advantage, of the load balancing arm 100. In FIGS. 15 and 18, the support arm 110 is in a substantially horizontal position. In FIGS. 16 and 19, the support arm 110 is shown pivoted about the main pivot axis 132 about 30 degrees upward relative to horizontal. In FIGS. 17 and 20, the support arm 110 is shown pivoted about the main pivot axis 132 about 85 degrees downward from horizontal. As will be appreciated, then, the support arm 110 has an angle of rotation about the main pivot axis 132 of about 30 degrees upward from horizontal to about 85 degrees downward from horizontal.

FIGS. 21-38 show a load balancing arm 500 according to another embodiment of the invention. The load balancing arm 500 is in many respects similar to the above-referenced load balancing arm 100, and consequently the same reference numerals are used to denote structures corresponding to similar structures in the load balancing arm 100. In addition, the foregoing description of the load balancing arm 100 is equally applicable to the load balancing arm 500 except as noted below. Moreover, it will be appreciated upon reading and understanding the specification that aspects of the load balancing arms 100, 500 may be substituted for one another or used in conjunction with one another where applicable.

Turning then to FIGS. 21-38, there is shown a load balancing arm 500 of the medical device support system 10 in accordance with an embodiment of the invention. The load balancing arm 500 includes a proximal hub 104, an adjustable bearing element 108, a support arm 110, a spring 116, and one or more links, two such links 124, 126 in the illustrative embodiment, as shown in FIGS. 21-22 and 31-32. The load balancing arm 500 also includes a distal hub 510 shown in FIGS. 21, 23-25, 28 and 37-38, a parallel link 520 shown in FIGS. 22, 25, 27-32 and 34-38, and a load adjustment base 530 shown in FIGS. 22 and 31-33. The proximal hub 104 may include a support structure 24 such as the drop tube 24 (see FIG. 1). The proximal hub 104 includes a main bearing element 130 that defines a main pivot axis 132. The adjustable bearing element 108 defines an adjustable pivot axis 142 that is adjustable relative to the main pivot axis 132. The support arm 110 has a proximal end 150 and a distal end 152. The distal end 152 is pivotably mounted to the distal hub 510, which, in turn, is configured to support a medical device load 36 (see FIG. 1). The proximal end 150 is pivotably mounted to the main bearing element 130 for pivotable movement about the main pivot axis 132. The pivotable movement raises and lowers the height of the medical device load 36 at the distal end 152.

The spring 116 extends within a cavity 154 of the support arm 110 and is mounted to exert a biasing force between the main pivot axis 132 and a distal end 158 of the spring 116. The links 124, 126 each have a proximal end 160 and a distal end 162. The proximal end 160 is pivotably mounted to the adjustable bearing element 108 for pivotable movement about the adjustable pivot axis 142. The distal ends 162 of the links 124, 126 are pivotably mounted to the distal end 158 of the spring 116 such that the biasing force exerted by the spring 116 is transmitted through the links 124, 126 to the adjustable bearing element 108 thereby to generate a moment about the main pivot axis 132 of the proximal hub 104 that counters a moment generated by the medical device load 36 at the distal end 152 of the support arm 110, thereby balancing the medical device load 36.

Thus, in the load balancing arm 500 according to the present embodiment, the links 124, 126 connect at their proximal ends 160 to an adjustment bearing element 108 and at their distal ends 162 to the distal end 158 of the spring 116. As will be described in greater detail below, the attachment at the distal end 158 of the spring 116 allows for a relatively longer link than if connected to the proximal end of the spring 116. This allows for a better force transmission and less spring travel resulting in a more balanced load balancing arm 500 throughout the pivotable range of travel of the arm 500.

Figure 21:
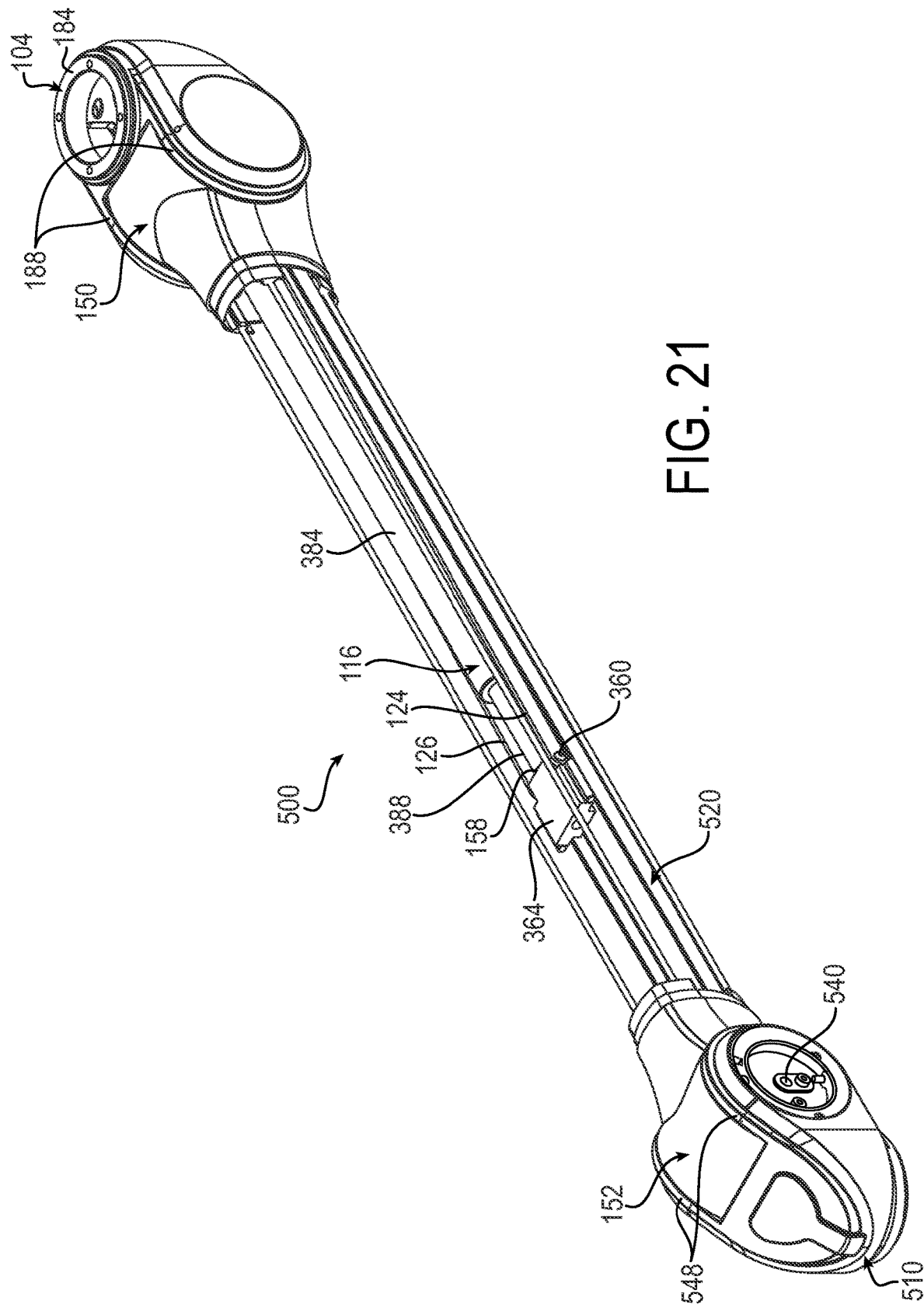
FIG. 21 is a top perspective view of a load balancing arm in accordance with another embodiment of the invention, with a support arm structure removed to show internal components of the load balancing arm.
Figure 22:
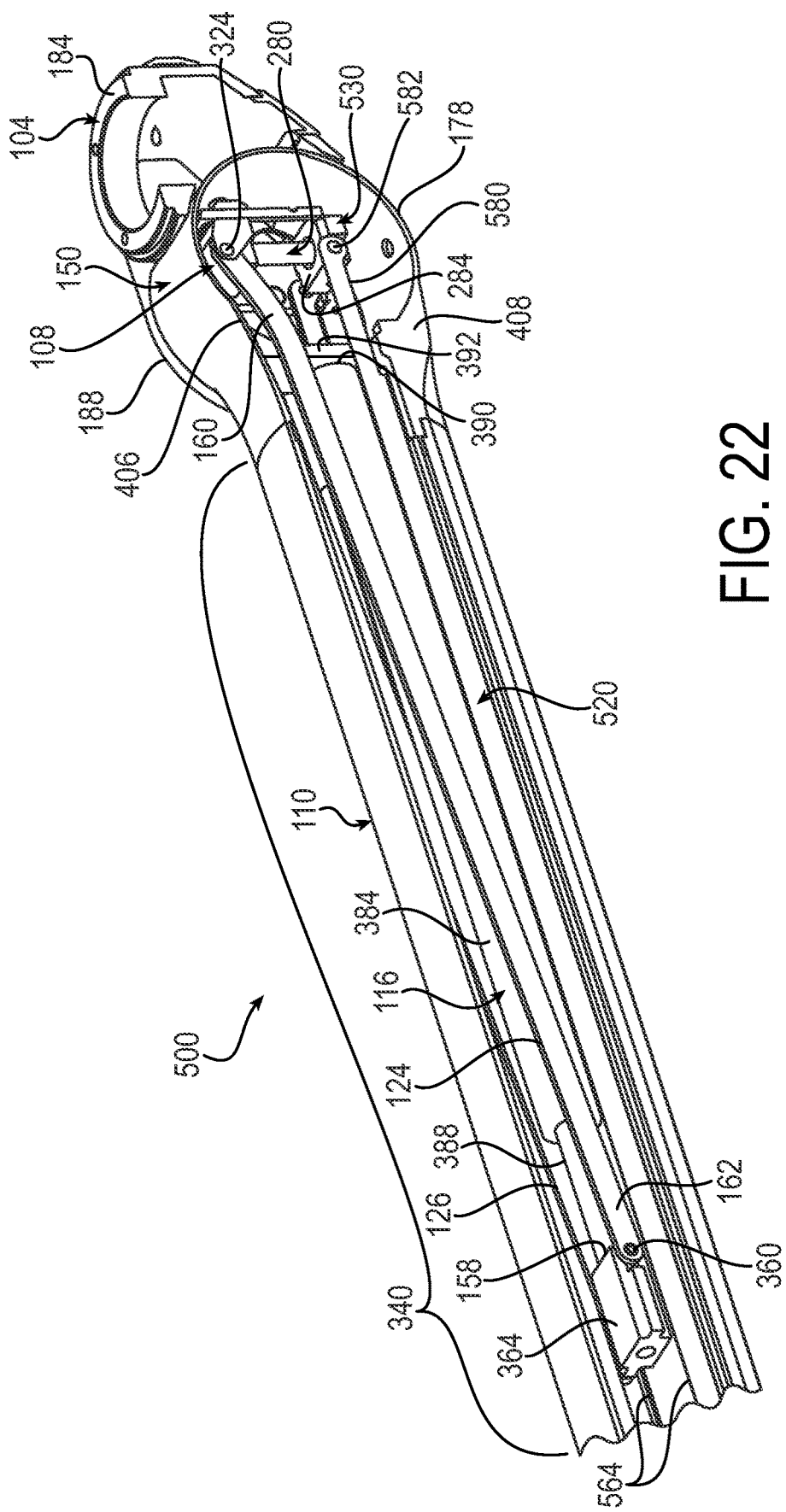
FIG. 22 is a partial top perspective view of the FIG. 21 load balancing arm, shown in partial cross section to show internal components of the load balancing arm.
Figure 24:
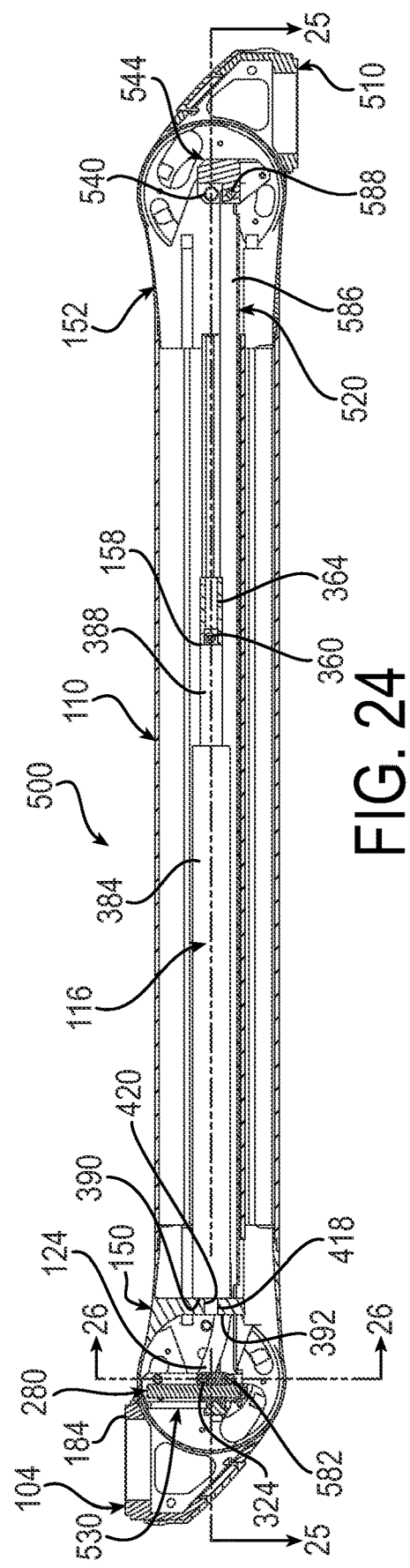
FIG. 24 is a side cross section view of the FIG. 21 load balancing arm as viewed from the plane 24-24 in FIG. 25, as though the load balancing arm in FIG. 25 were whole.
Figure 25:
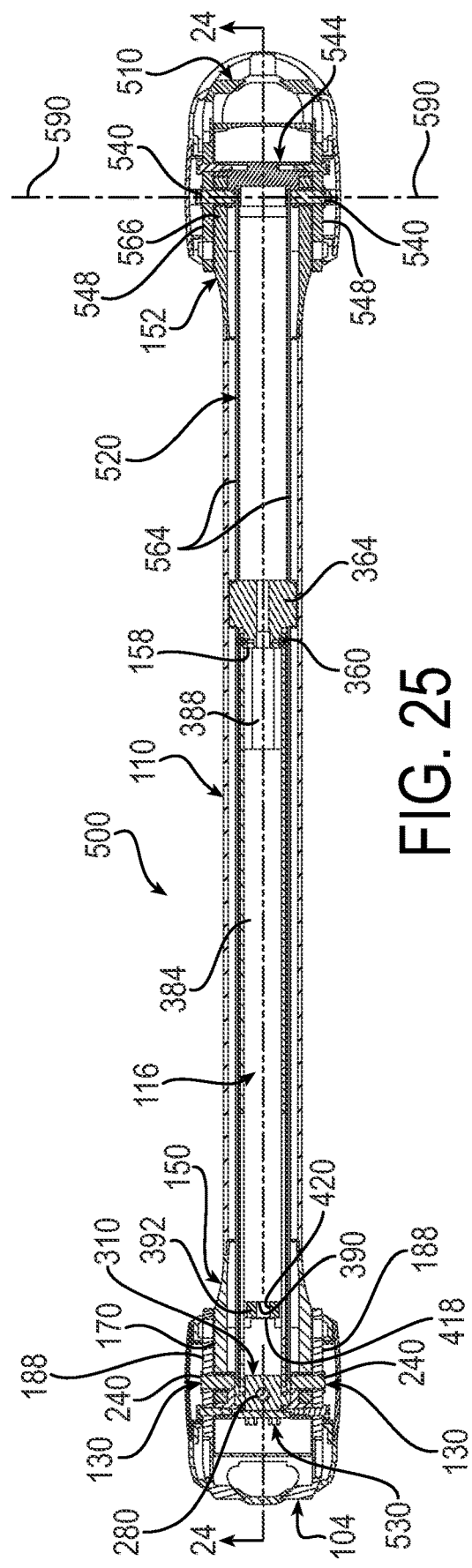
FIG. 25 is a top cross section side view of the FIG. 21 load balancing arm as viewed from the plane 25-25 in FIG. 24, as though the load balancing arm in FIG. 24 were whole.
Figure 26:
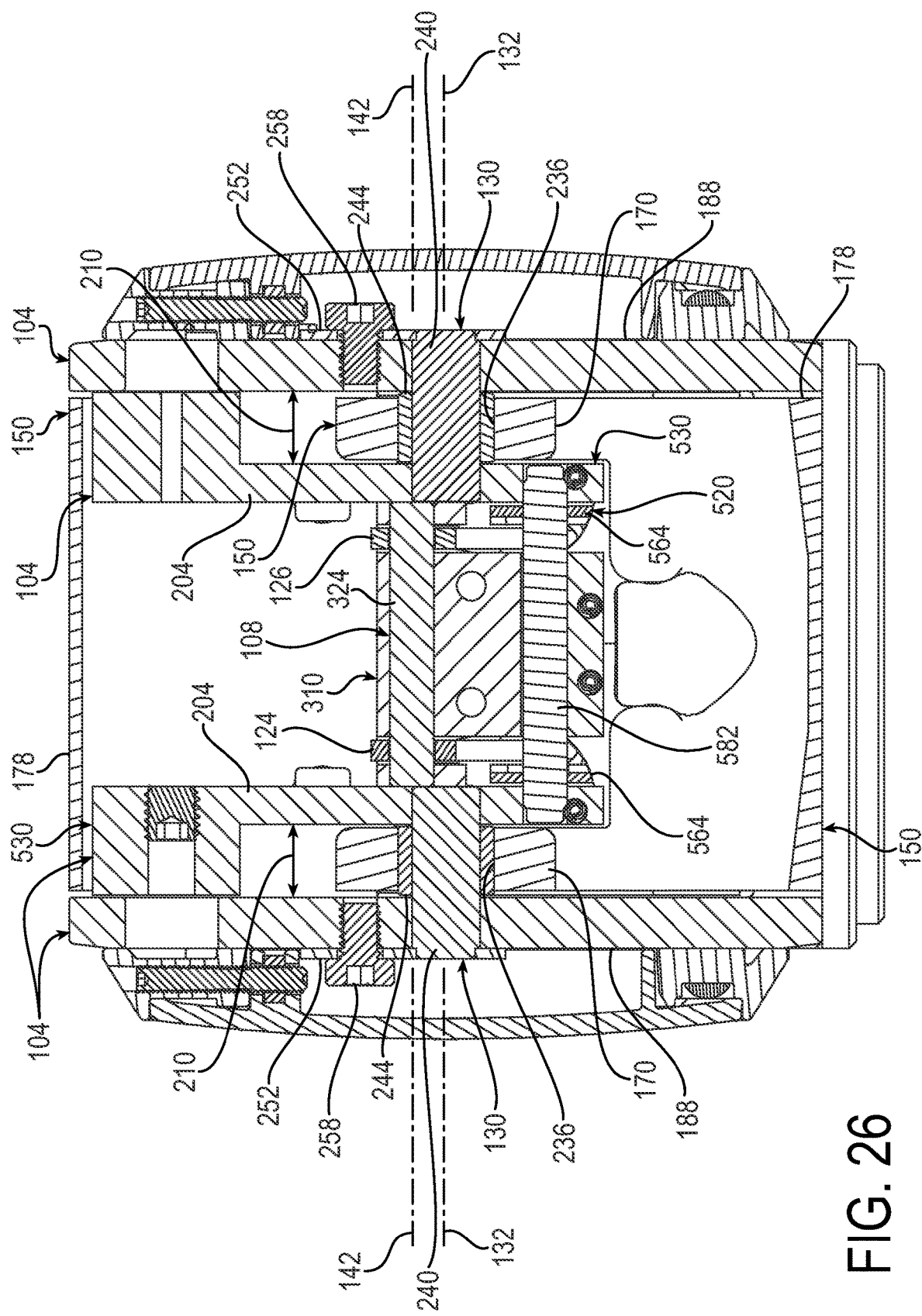
FIG. 26 is an end cross section view of the FIG. 21 load balancing arm as viewed from the plane 26-26 in FIG. 24, as though the load balancing arm in FIG. 24 were whole.
Figure 31:
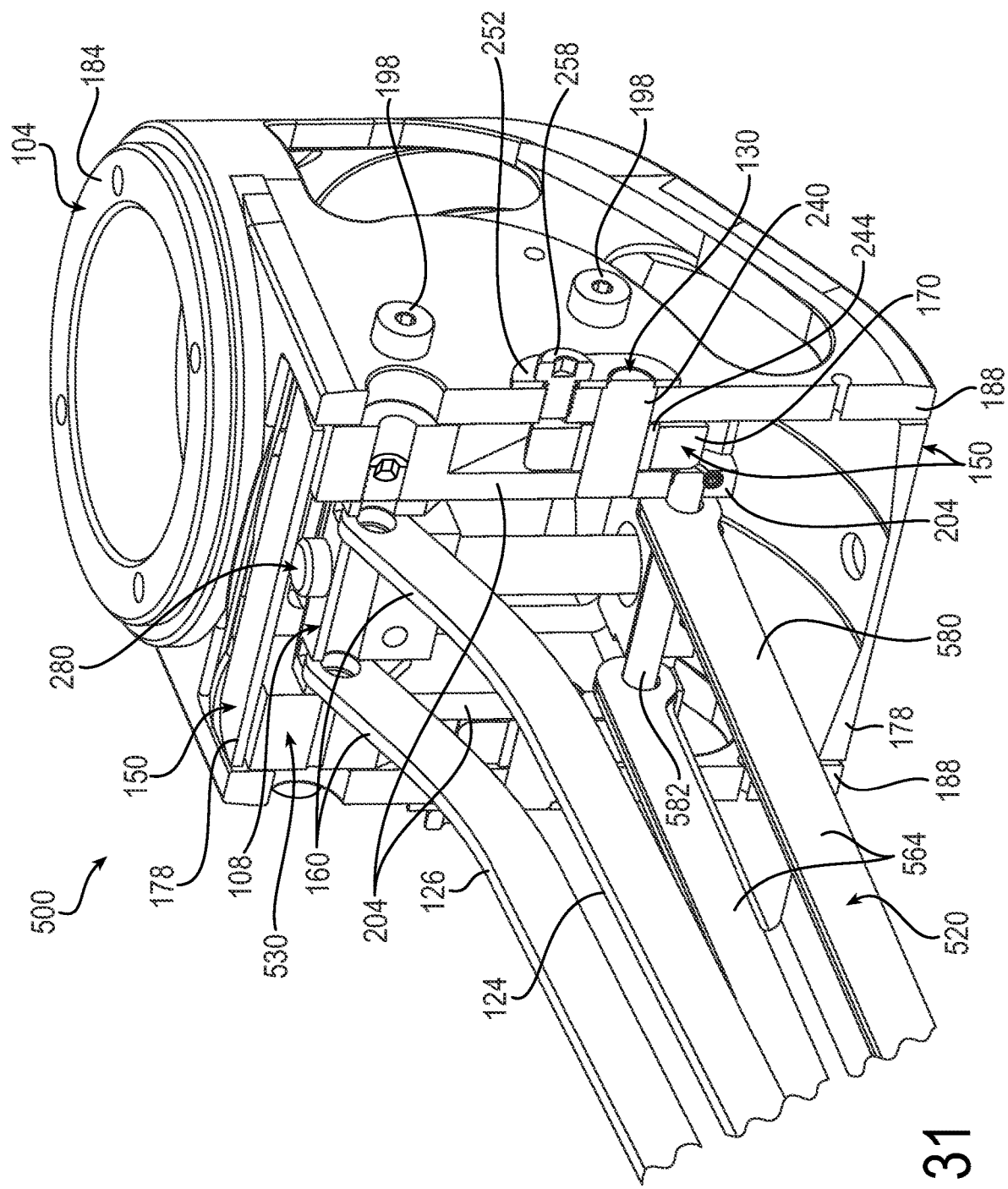
FIG. 31 is a partial cross section perspective view of a proximal end of the FIG. 21 load balancing arm, showing internal components of the load balancing arm.

Reference is now made to FIGS. 21-27, 31 and 34-36, which show greater detail of the support arm 110, the proximal hub 104, and the interface between the support arm 110 and proximal hub 104. As shown in FIGS. 21-22 and 31, the proximal end 150 of the support arm 110 has a relatively smaller width than the proximal hub 104 and fits within the proximal hub 104. In the illustrated embodiment, the proximal end 150 of the support arm 110 includes a pair of vertically oriented laterally spaced protrusions or tongue portions 170 and a circular portion 178 substantially surrounding the tongue portions 170. As shown in FIGS. 22, 26 and 31, the proximal hub 104 includes a mounting surface 184 for mounting the proximal hub 104 and thus the load balancing arm 100 to, for example, the distal end of an extension arm 16. The proximal hub 104 includes a pair of vertically oriented side walls 188 alongside which the tongue portions 170 of the support arm 110 slide during adjusting of the support arm 110. In side profile, the side walls 188 have a circular shape that corresponds in diameter to the circular portion 178 of the proximal end 150 of the support arm 110.

The proximal hub 104 also includes a load adjustment base 530 that extends width-wise between the pair of vertically oriented side walls 188 and that, as shown in FIGS. 22, 27 and 34-36 extends vertically downward from a location just below the vertically uppermost portion of the circular portion 178 of the proximal end 150 of the support arm 110 downward approximately three fourths the distance across the circular portion 178. Details of one example of the load adjustment base 530 are shown in FIGS. 22, 24-27 and 31-36. As shown in FIGS. 26 and 31, the load adjustment base 530 may be fastened to the side walls 188 by fasteners 198. As shown in FIGS. 26 and 31-33, the load adjustment base 530 has a pair of laterally spaced flanges 204 that are recessed inward from the outer width of the load adjustment base 530. Referring to FIG. 26, the recessed flanges 204 form respective gaps 210 with the side walls 188 within which the tongue portions 170 of the support arm 110 are received. As shown in FIG. 26, the tongue portions 170 of the proximal end 150 of the support arm 110 have through holes 236 and the main bearing element 130 of the proximal hub 104 includes a pair of laterally spaced pins 240. The central axis of these pins 240 defines or coincides with the main pivot axis 132. The through holes 236 receive the pins 240 thereby to pivotably mount the proximal end 150 of the support arm 110 to the main bearing element 130 of the proximal hub 104 for pivotable movement of the support arm 110 about the main pivot axis 132.

Figure 23:
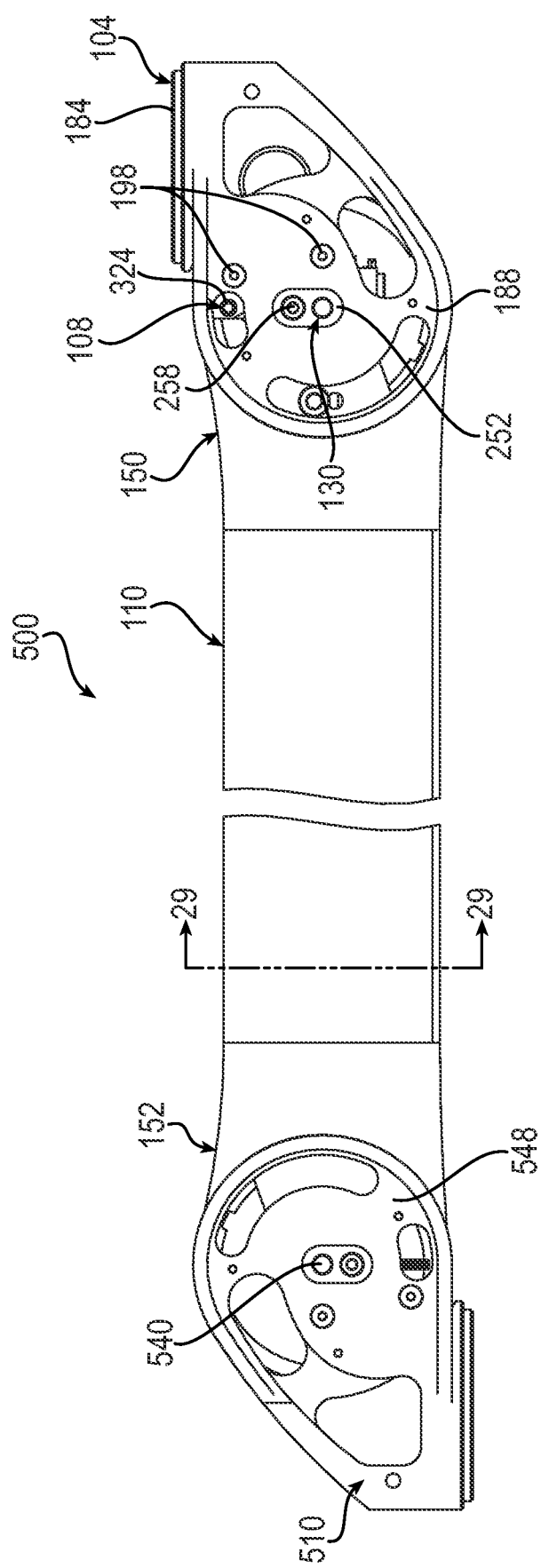
FIG. 23 is a side view of the FIG. 21 load balancing arm, enlarged to show the proximal and distal ends in more detail.

In the illustrative embodiment, bushings 244 are provided on the pins 240 to promote smooth pivotable operation and serviceability. As shown in FIGS. 23, 26 and 31, the pins 240 are fixedly connected, for example by welding, to a retainer plate 252, which, in turn, is fastened to the side walls 188 of the proximal hub 104 by fasteners 258.

Figure 27:
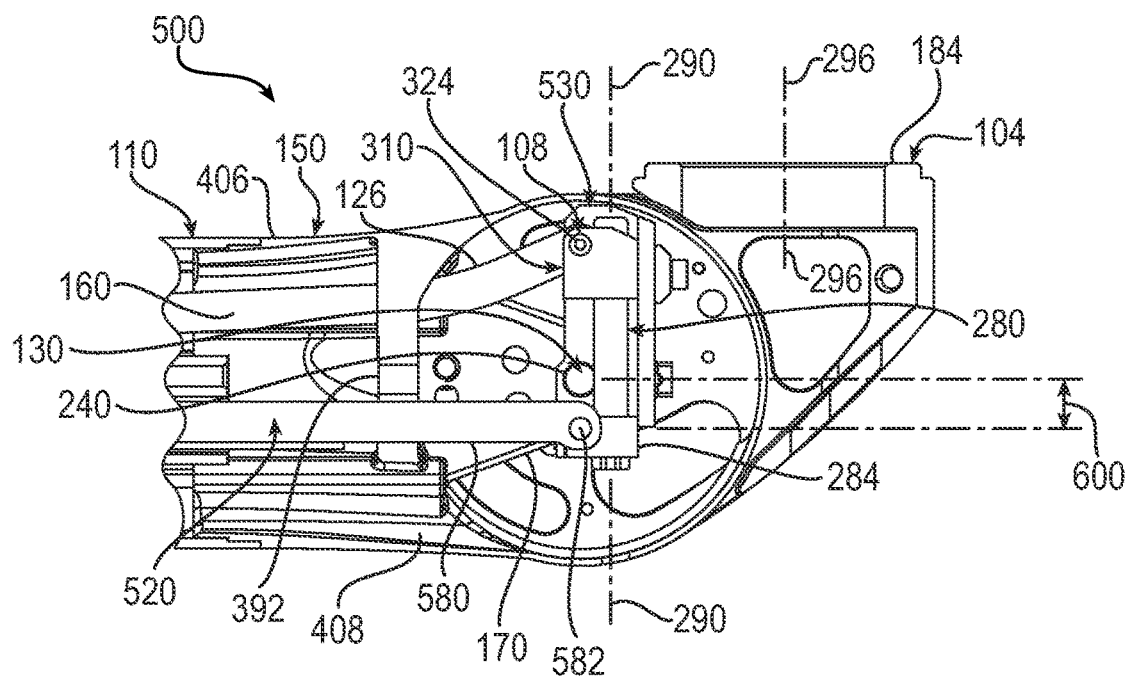
FIG. 27 is a side cross section view of a proximal end of the FIG. 21 load balancing arm, showing internal components of the load balancing arm.
Figure 32:
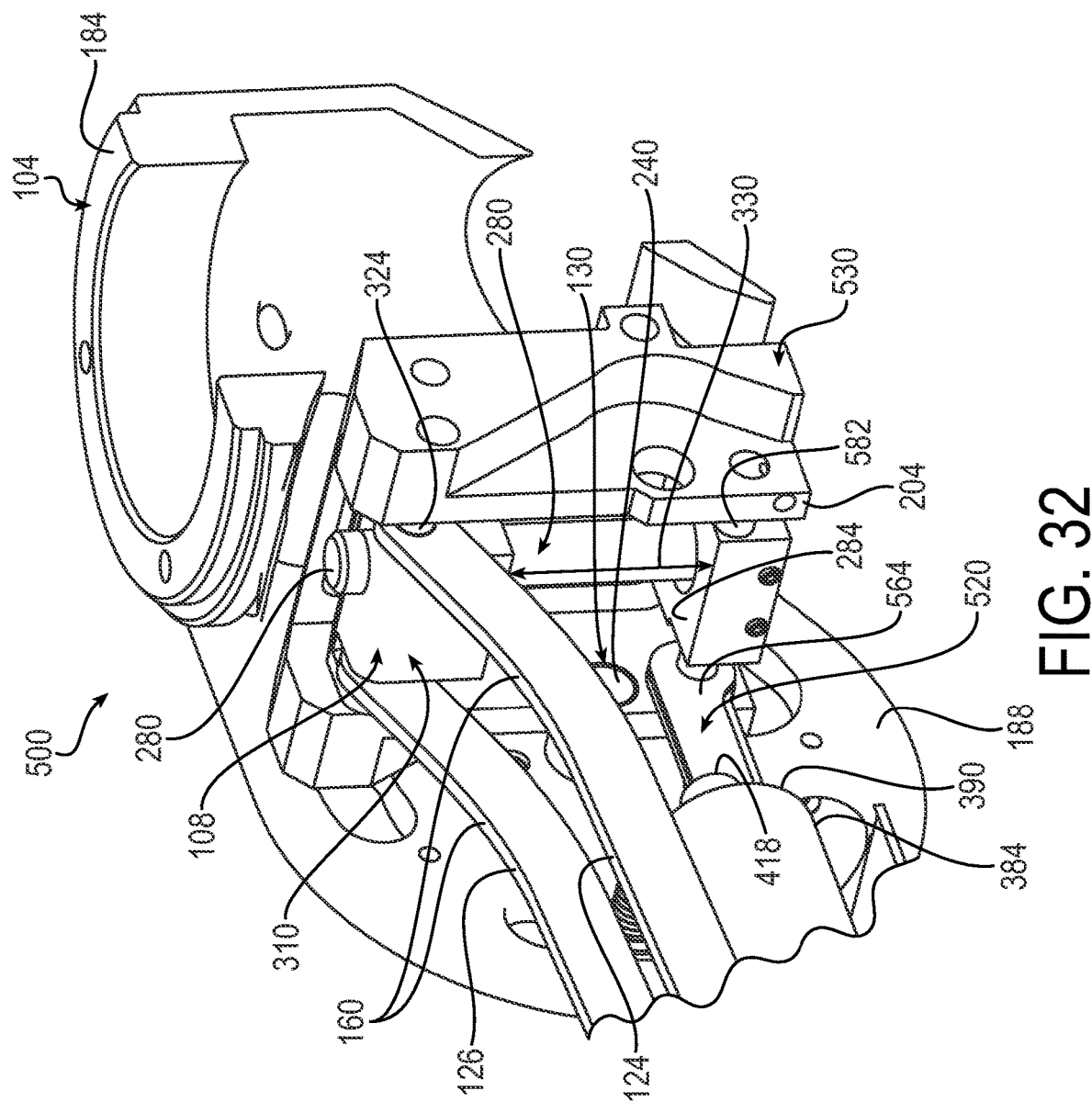
FIG. 32 is a partial cross section perspective view of a proximal end of the FIG. 21 load balancing arm, showing internal components of the load balancing arm.
Figure 33:
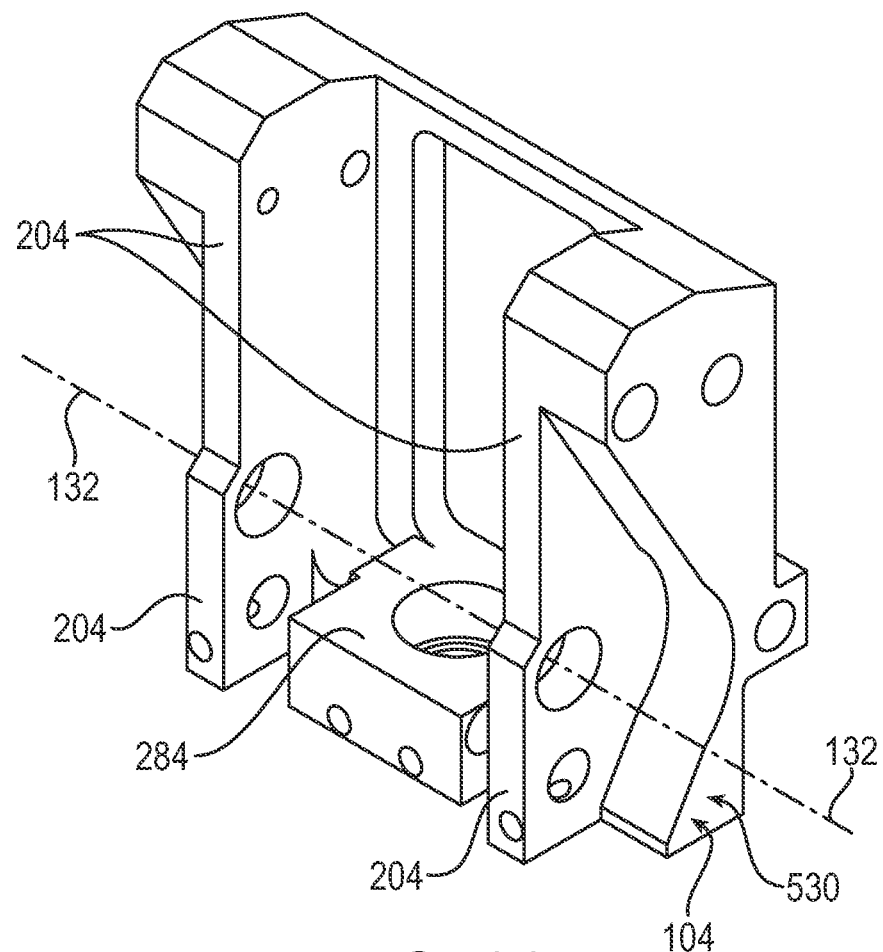
FIG. 33 is a side perspective view of a load adjustment base of a proximal hub of the FIG. 21 load balancing arm.

As shown in FIGS. 22, 27, 32 and 33, a load adjustment screw 280 is rotatably mounted in a bottom wall 284 of the load adjustment base 530. The load adjustment screw 280 is fixed in a vertical orientation in the proximal hub 104 and rotates about its own central axis 290. Referring to FIGS. 1 and 27, in the present embodiment, the axis 290 of the load adjustment screw 280 is parallel to an axis 296 of rotation of the load balancing arm 500 extending centrally through the support structure 24 and perpendicular to horizontal. As shown in FIGS. 25-27 and 32, the adjustable bearing element 108 includes a load adjustment nut 310 that threadably engages the load adjustment screw 280 to adjust the adjustable pivot axis 142 relative to the main pivot axis 132. The load adjustment nut 310 moves in the vertical direction as the load adjustment screw 280 is rotated, which vertical movement adjusts the adjustable pivot axis 142 relative to the main pivot axis 132. As shown in FIGS. 26 and 27, the adjustable bearing element 108 includes a pin 324 that is carried by the load adjustment nut 310. The central axis of the pin 324 defines or coincides with the adjustable pivot axis 142. As shown in FIGS. 26, 27 and 32, the proximal ends 160 of the links 124, 126 are pivotably mounted to the pin 324 at respective opposite ends of the pin 324. The adjustable pivot axis 142 is adjustable relative to the main pivot axis 132 over a range of adjustment 330, defined in the illustrative embodiment by the uppermost and lowermost vertical position of the load adjustment nut 310, as shown in FIG. 32.

The vertical movement of the load adjustment nut 310 adjusts the load capacity of the load balancing arm 500. As will be appreciated, the distance between the adjustable pivot axis 142 of the pin 324 and the main pivot axis 132 of the proximal hub 104 provides the mechanical advantage, or moment, that allows the load balancing arm 500 to balance a medical device load 36 at the distal end 152 of the arm 500.

With reference to FIG. 26, the laterally spaced pins 240 split the main pivot axis 132 thereby enabling the adjustable bearing element 108 to be moved vertically across the main pivot axis 132 into a position between the laterally spaced pins 240. Accordingly, the adjustable bearing element 108 and the proximal ends 160 of the respective pair of links 124, 126 are movable between the pair of pins 240 over a portion of the range of adjustment 330. As will be appreciated, this provides greater adjustment range in the proximal ends 160 of the links 124, 126 pivotably mounted to the pin 324 of the adjustable bearing element 108 than if the pins 240 were a single pin member and the main pivot axis 132 was not split.

Referring to FIGS. 26 and 27, the adjustable pivot axis 142 of the adjustable bearing element 108 and the main pivot axis 132 of the main bearing element 130 are horizontally offset the same distance from the axis 296 of rotation of the load balancing arm 500 extending centrally through the support structure 24.

Turning now to FIGS. 22, 27 and 34-36, the support arm 110 includes an intermediate portion 340 between the proximal end 150 and distal end 152 of the support arm 110. The intermediate portion 340 has a relatively narrower height span than the circular portion 178 of the proximal end 150 of the support arm 110. The links 124, 126 (only link 124 is in view in FIGS. 34-36) have at least one bend that corresponds to the difference in height span between the intermediate portion 340 and the circular portion 178 of the proximal end 150 of the support arm 110. In the illustrative embodiment, the links 124, 126 have one bend and consequently have a J-shape in side view. Other shapes such as S-shape (two bends) are also contemplated. The bend in the links 124, 126 aids in the load balancing arm 500 having a smaller size and lower overall cross section profile than if the links 124, 126 were straight. The smaller size and lower overall cross section profile make the load balancing arm 500 less obstructive in the operating room and improve the laminar airflow around the surface of the load balancing arm 100.

Figure 29:
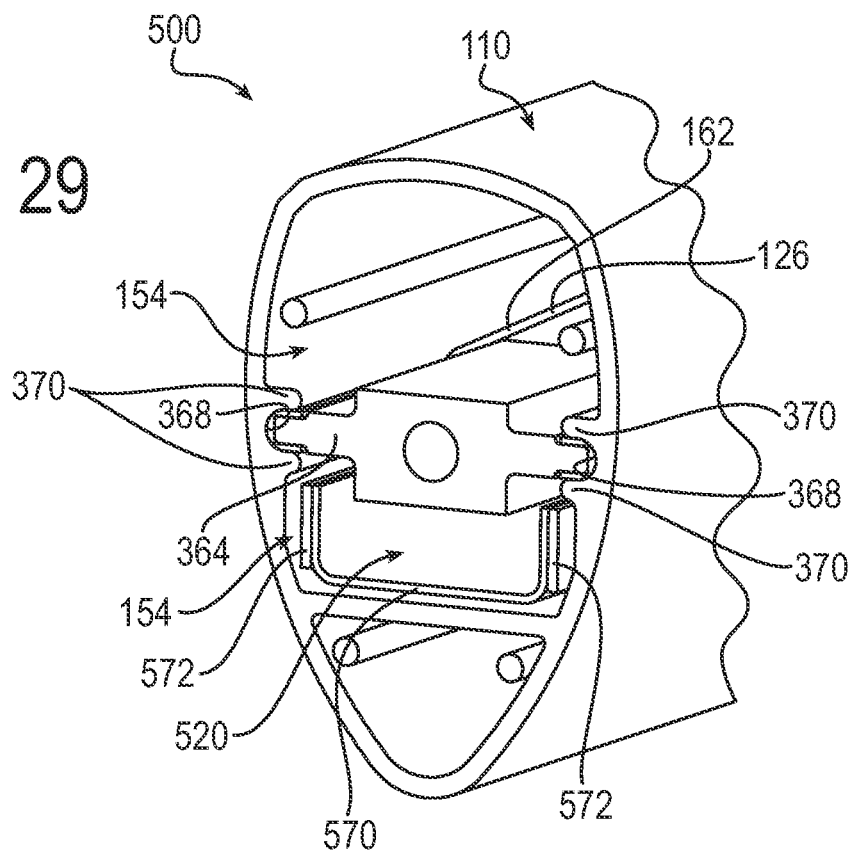
FIG. 29 is cross section view of the FIG. 21 load balancing arm as viewed from the plane 29-29 in FIG. 23.

The distal ends 162 of the links 124, 126 are pivotably mounted to the distal end 158 of the spring 116 via a carriage slide 364 that is slidable relative to the support arm 110. The pivotable connection may be facilitated by, for example, a pin 360 mounted within the carriage slide 364. As shown in FIG. 29, the carriage slide 364 is slidable within at least one groove 368 in the support arm 110, wherein in the illustrative embodiment there are two such grooves 368 at laterally opposite sides of the support arm 110. The grooves 368 are oriented along an axis that extends radially from and perpendicular to the main pivot axis 132. The grooves 368 are formed by parallel ribs 370 in the inward facing walls of the support arm 110. The ribs 370, along with a horizontal cross beam in the bottom portion of the support arm 110, also serve as stiffening members.

The spring 116 of the load balancing arm 500 may be any type of counterbalancing member, and in the illustrative embodiment is a compression gas spring 116. Like the grooves 368, the spring 116 is oriented along an axis that extends radially from and perpendicular to the main pivot axis 132. The spring 116 has a cylinder 384 and a rod 388. Referring to FIGS. 22, 24, 27 and 32, the cylinder 384 has a proximal end wall 390 that is coupled to a vertical beam 392 of the support arm 110. As shown in FIG. 22, the vertical beam 392 extends from a top wall 406 to a bottom wall 408 of the support arm 110 and is sufficiently narrow that the links 124, 126 straddle the vertical beam 392 on opposite lateral sides thereof throughout the pivotable range of the load balancing arm 500. The proximal end wall 390 of the cylinder 384 may be coupled to the vertical beam 392 in any suitable manner, for example as by a protrusion 418, shown in FIG. 32, that fits within an opening 420 in the vertical beam 392, shown in FIGS. 24 and 25. The rod 388 is pivotably mounted to the distal ends 162 of the links 124, 126 via the pin 360 of the afore described carriage slide 364. In operation, the links 124, 126 straddle the spring 116 on laterally opposite sides of the spring 116 throughout the pivotable range of the load balancing arm 500.

FIGS. 21, 23-25, 28 and 37-38 show detail of the distal hub 510 of the load balancing arm 500. The distal hub 510 is pivotably connected to the distal end 152 of the support arm 110 via a pair of laterally spaced pins 540 held in flanges of a vertical block 544 of the distal hub 510. The vertical block 544 can be fixedly connected to a pair of vertically oriented side walls 548 of the distal hub 510 in a similar manner that the load adjustment base 530 is connected to the side walls 188 of the proximal hub 104. Likewise, the distal end 152 of the support arm 110 can include laterally spaced protrusions 566 that pivotably connect to the respective laterally spaced pins 540 in a similar manner that the proximal end protrusions 170 pivotably connect to the laterally spaced pins 240 of the proximal hub 104.

Figure 30:
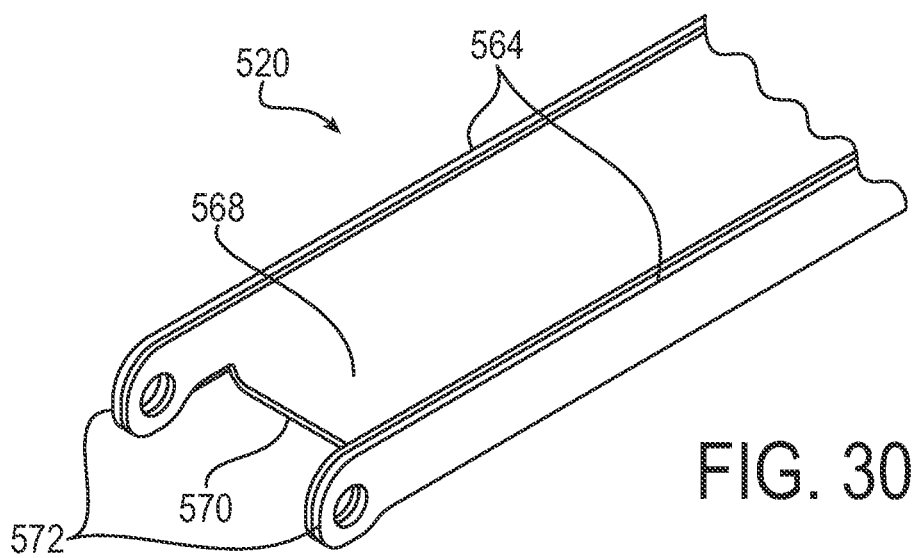
FIG. 30 is a perspective view of an end portion of a parallel link of the FIG. 21 load balancing arm.

FIGS. 22, 25, 27-32 and 34-38 show detail of the parallel link 520 of the load balancing arm 500. The illustrative parallel link 520 is a single U-shape link with two vertically oriented laterally spaced parallel side walls 564 and a lower bridge member 568 connecting the bottom edges of the side walls 564. It will be appreciated that the parallel link 520 may comprise two parallel links in the form of the two parallel side walls 564 with the lower bridge member 568 omitted. Referring to FIGS. 29 and 30, in the present embodiment, the parallel link 520 is made up of two pieces, a U-shape stainless steel member 570 and a pair of relatively harder stainless steel side braces 572 tack welded to the U-shape stainless steel member 570.

Figure 35:
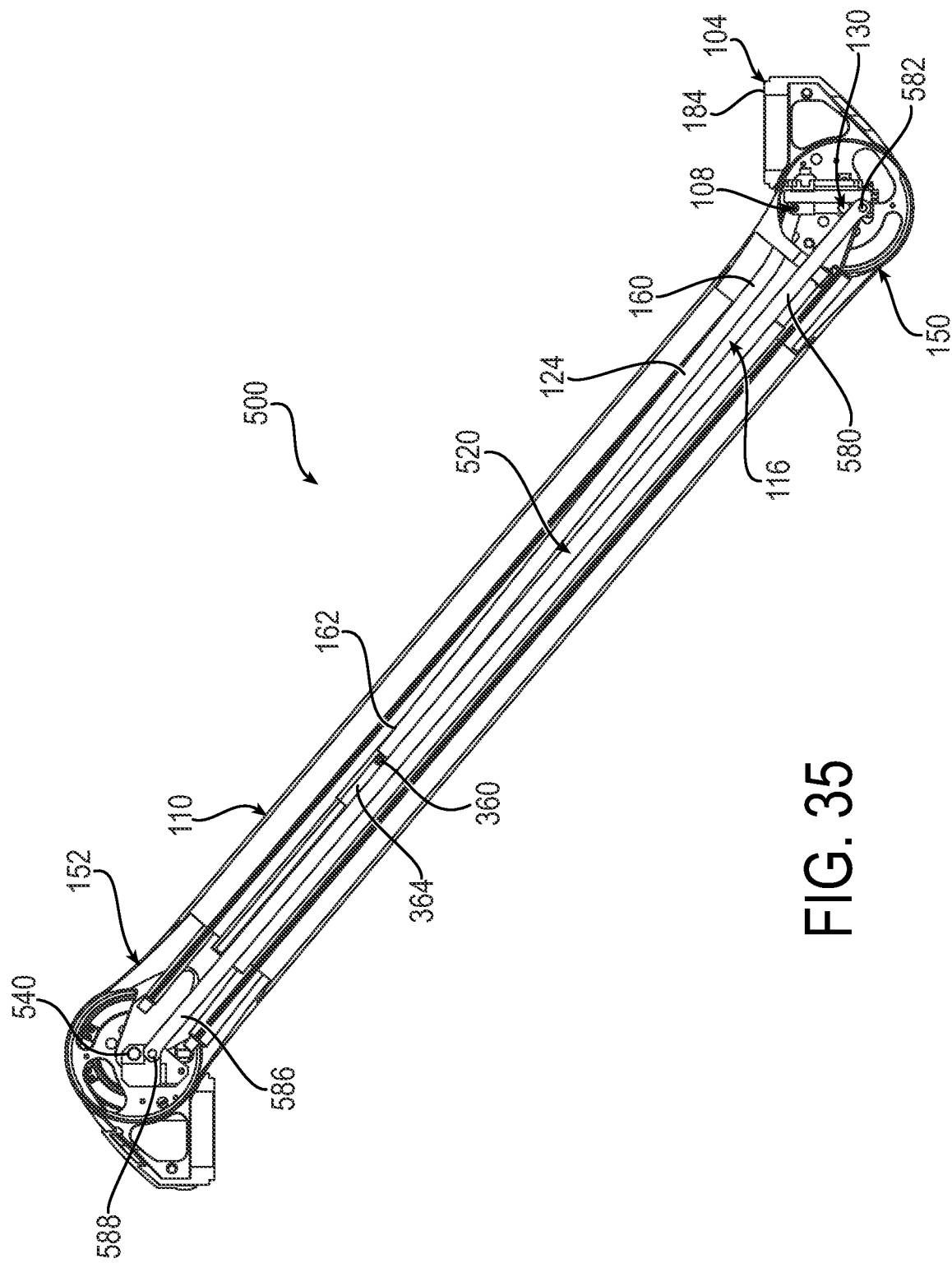
FIG. 35 is a side cross section view of the FIG. 21 load balancing arm in a position upward from horizontal, showing internal components of the load balancing arm.

The parallel link 520 is pivotably connected at its proximal end 580 to a pin 582 supported by the load adjustment base 530 of the proximal hub 104 and at its distal end 586 to a pin 588 supported by the vertical block 544 of the distal hub 510. As shown in FIG. 35, the split main pivot axis 132, i.e. the laterally spaced pins 240, enable the proximal end 580 of the parallel link 520 to move between the pins 240 for example when the load balancing arm 500 is pivoted to upper positions. Likewise, as shown in FIGS. 25 and 36, the split pivot axis 590, i.e. the laterally spaced pins 540, enable the distal end 586 of the parallel link 520 to move between the pins 540 for example when the load balancing arm 500 is pivoted to lower positions.

Figure 28:
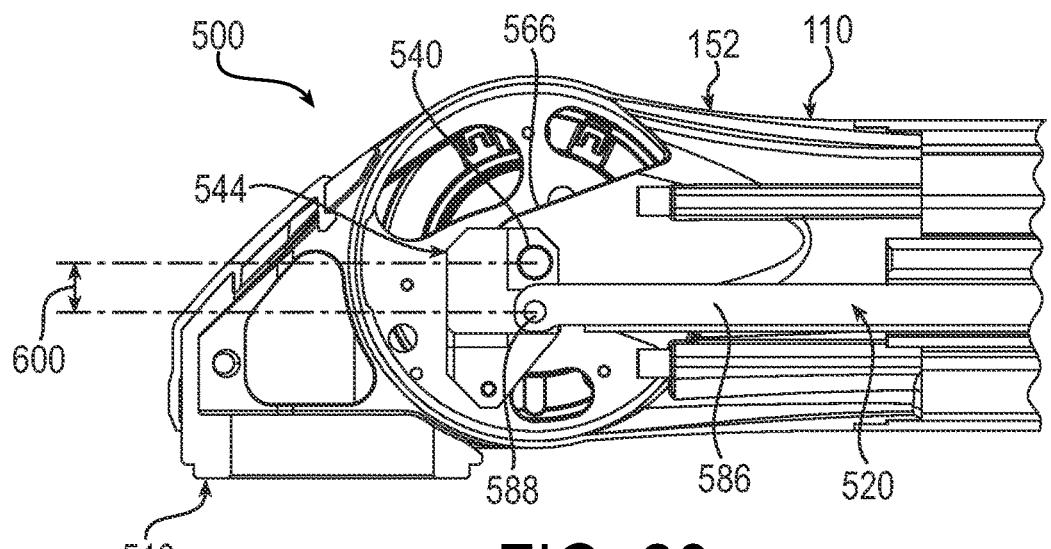
FIG. 28 is a side cross section view of a distal end of the FIG. 21 load balancing arm, showing internal components of the load balancing arm.

As shown in FIGS. 27 and 28, the pin 582 is oriented vertically below the pins 240 a distance 600 and the pin 588 is oriented vertically below the pins 540 by the same distance 600. Also, the horizontal distance between the pins 540 and the pins 240 at opposite ends of the support arm 110 is equal to the horizontal distance between the pin 588 and the pin 582 at opposite ends of the parallel link 520. In this way, a parallelogram is formed by the structure of the support arm 110 between the pins 540 and the pins 240, the portion of the load adjustment base 530 between the pins 240 and the pin 582, the parallel link 520 between the pin 582 and the pin 588, and the portion of the vertical block 544 between the pin 588 and the pins 540. Referring to FIGS. 34-38, owing to this parallelogram linkage, the vertically aligned pins 540, 588 at the distal end 152 remain parallel to the vertically aligned pins 240, 582 at the proximal end 150 throughout the pivotable range of the load balancing arm 500 about the main pivot axis 132. This permits a medical device load 36 such as a monitor to remain properly oriented regardless of its vertical displacement from the ceiling of the operating room.

Referring now to FIGS. 22, 25, 26, 31 and 32, the side walls 564 of the parallel link 520 straddle the vertically lower portion of the gas spring 116 on laterally opposite sides thereof. The side walls 564 also straddle the links 124, 126 on laterally opposite sides of the links 124, 126 over at least a portion of the pivotable range of the load adjustment arm 500, particularly when the adjustable bearing element 108 is in lower positions as shown in FIG. 24.

Figure 34:
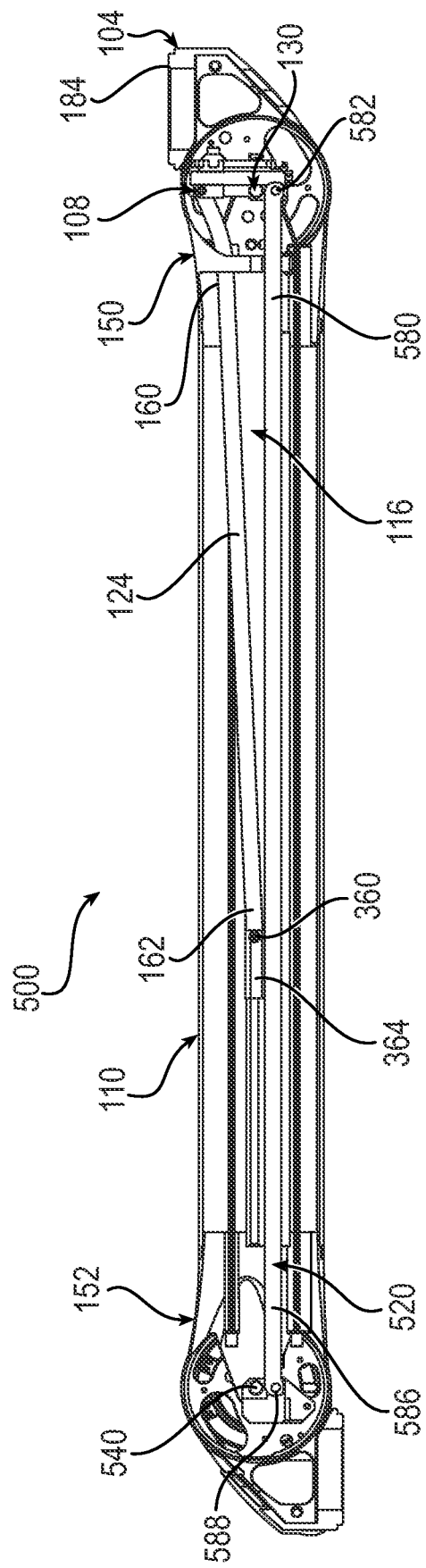
FIG. 34 is a side cross section view of the FIG. 21 load balancing arm in a substantially horizontal position, showing internal components of the load balancing arm.
Figure 36:
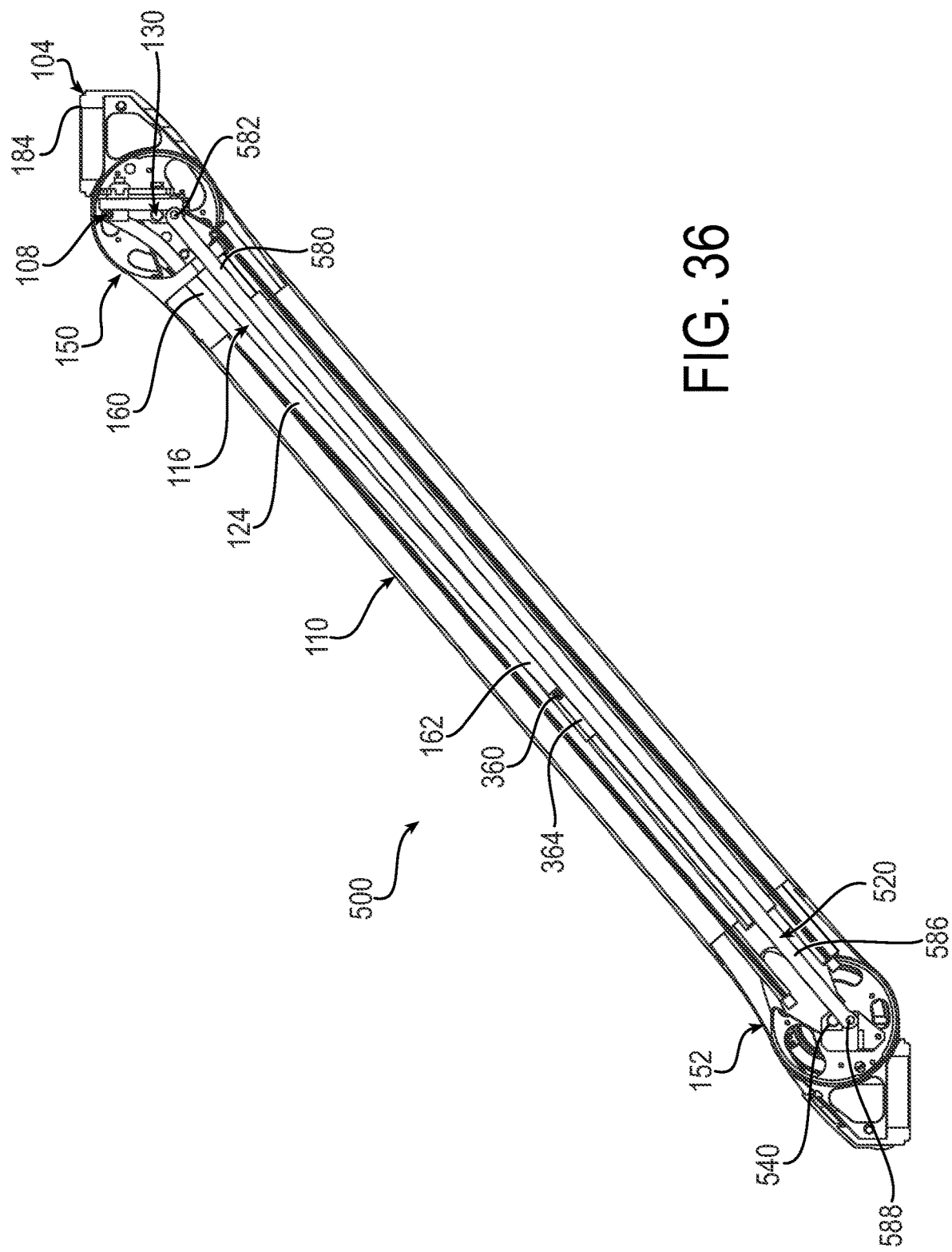
FIG. 36 is a side cross section view of the FIG. 21 load balancing arm in a position downward from horizontal, showing internal components of the load balancing arm.
Figure 37:
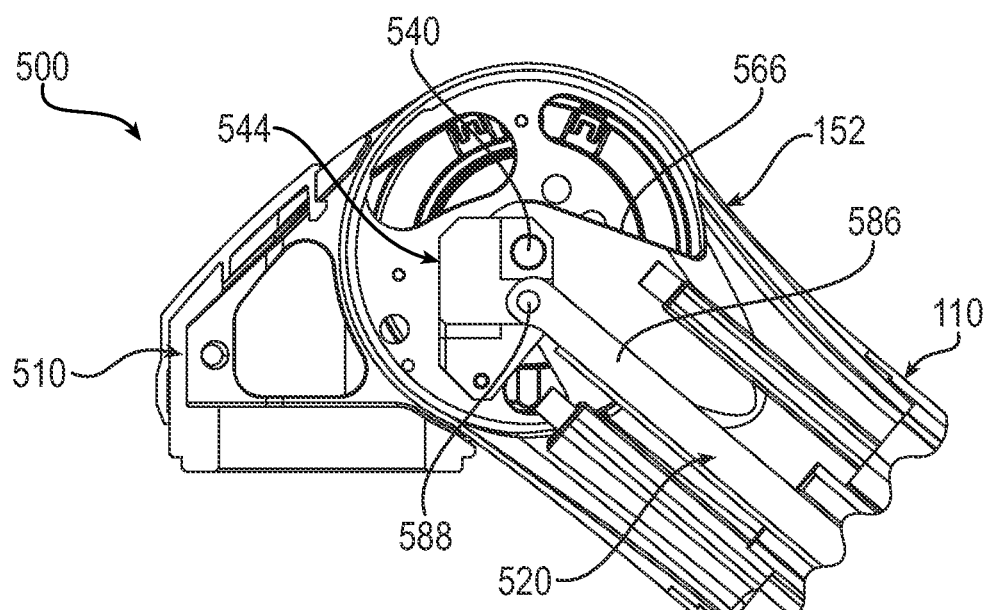
FIG. 37 is a side cross section view of the distal end of the FIG. 21 load balancing arm in a position upward from horizontal, showing internal components of the load balancing arm.
Figure 38:
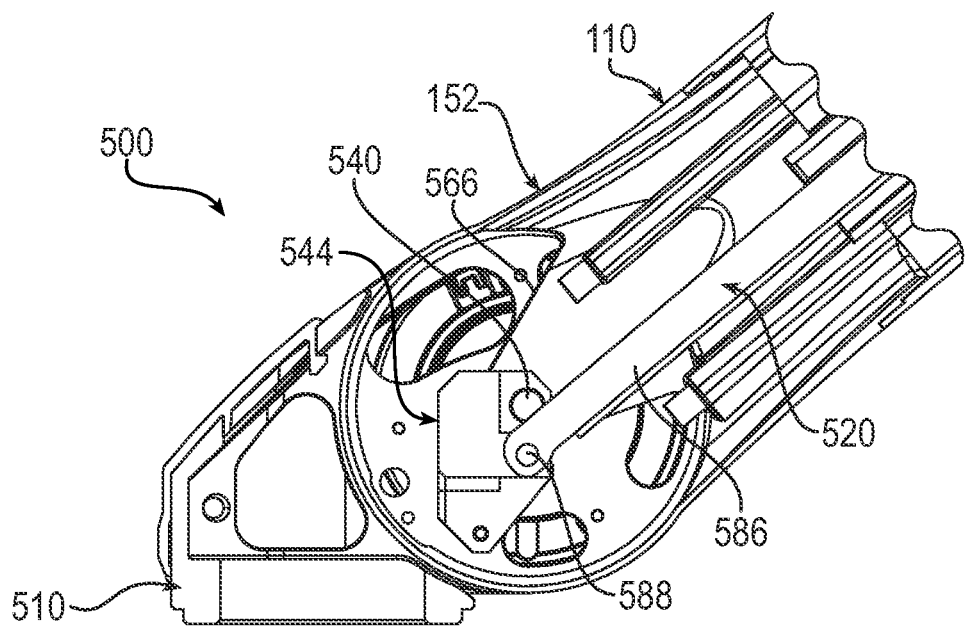
FIG. 38 is a side cross section view of the distal end of the FIG. 21 load balancing arm in a position downward from horizontal, showing internal components of the load balancing arm.
Figure 39:
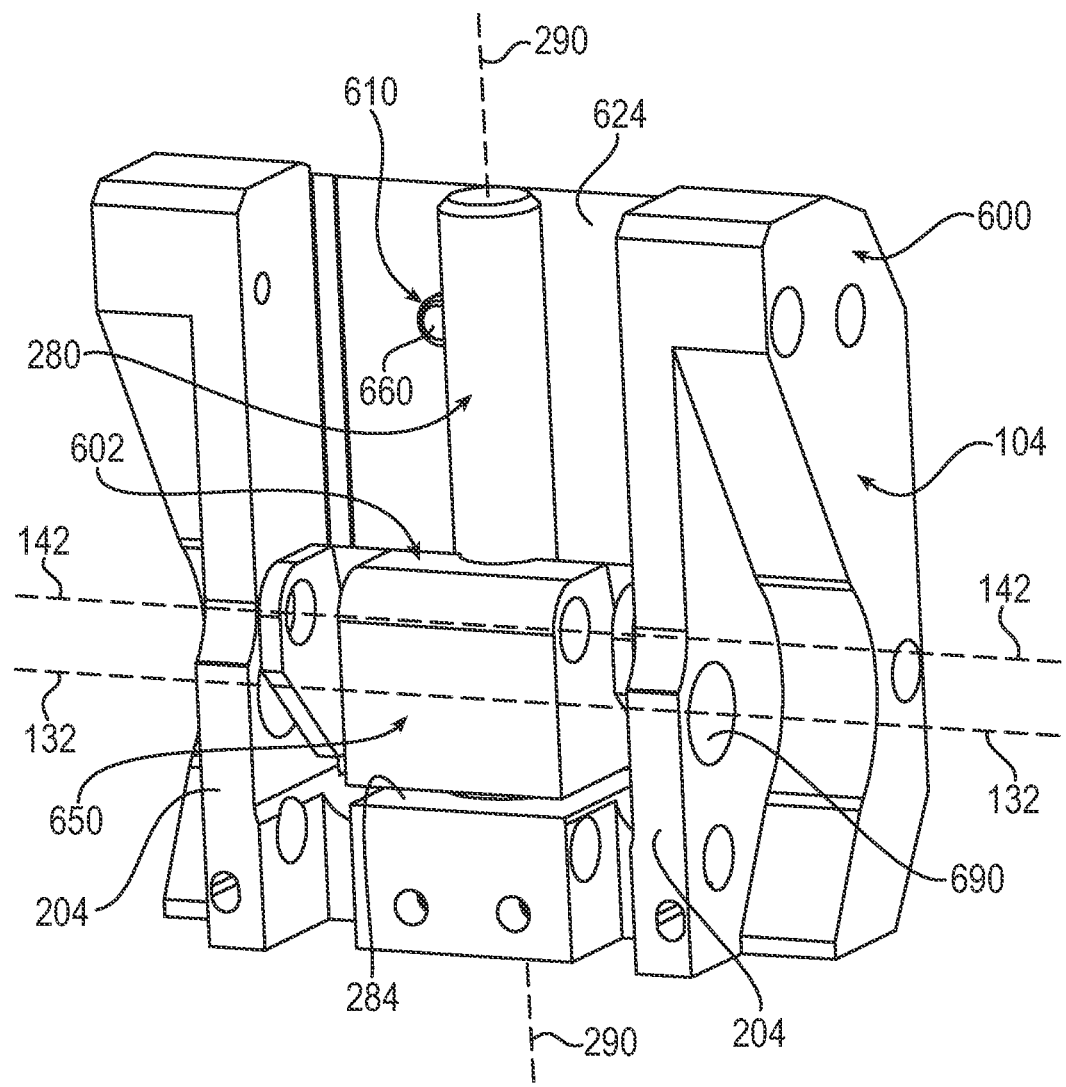
FIG. 39 is a front perspective view of a load adjustment base and an adjustable bearing element in accordance with another embodiment of the invention.

Reference is now made to FIGS. 34-36, which show the load balancing arm 500 in three different vertical positions, and FIGS. 37 and 38, which show the parallel link 520 and the distal end 152 of the support arm 110 relative to the distal hub 510 in the respective uppermost and lowermost vertical positions. The links 124, 126 are shown adjusted to their maximum height in FIGS. 34-36, thereby maximizing the moment, or mechanical advantage, of the load balancing arm 500. In FIG. 34, the support arm 110 is in a substantially horizontal position. In FIGS. 35 and 37, the support arm 110 is shown pivoted about the main pivot axis 132 about 40 degrees upward relative to horizontal. In FIGS. 36 and 38, the support arm 110 is shown pivoted about the main pivot axis 132 about 40 degrees downward from horizontal. As will be appreciated, then, the support arm 110 has an angle of rotation about the main pivot axis 132 of about 40 degrees upward from horizontal to about 40 degrees downward from horizontal.

FIGS. 39-45 show a load adjustment base 600 and an adjustable bearing element 602 according to another embodiment of the invention. The load adjustment base 600 and adjustable bearing element 602 are in many respects similar to the above-referenced load adjustment bases 196, 530 and adjustable bearing elements 108 shown for example in FIGS. 12-14, 20, 26 and 31-33, and consequently the same reference numerals are used in FIGS. 39-45 to denote structures corresponding to similar structures in the load adjustment bases 196, 530 and adjustable bearing elements 108. In addition, the foregoing description of the load adjustment bases 196, 530 and adjustable bearing elements 108 is equally applicable to the load adjustment base 600 and the adjustable bearing element 602 except as noted below. Moreover, it will be appreciated upon reading and understanding the specification that aspects of the load adjustment bases 196, 530, 600 may be substituted for one another or used in conjunction with one another where applicable, and aspects of the adjustable bearing elements 108, 602 may be substituted for one another or used in conjunction with one another where applicable.

Figure 40:
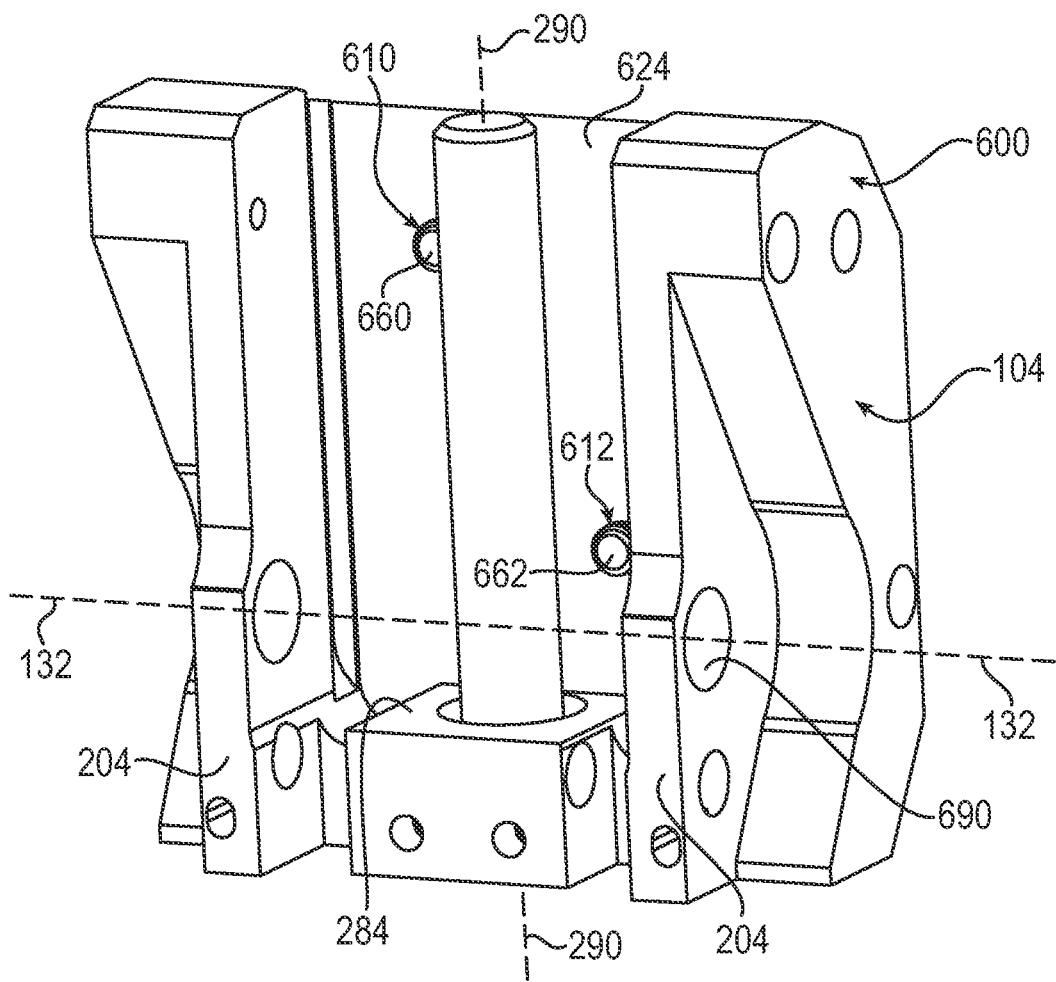
FIG. 40 is a front perspective view of the load adjustment base shown in FIG. 39.
Figure 41:
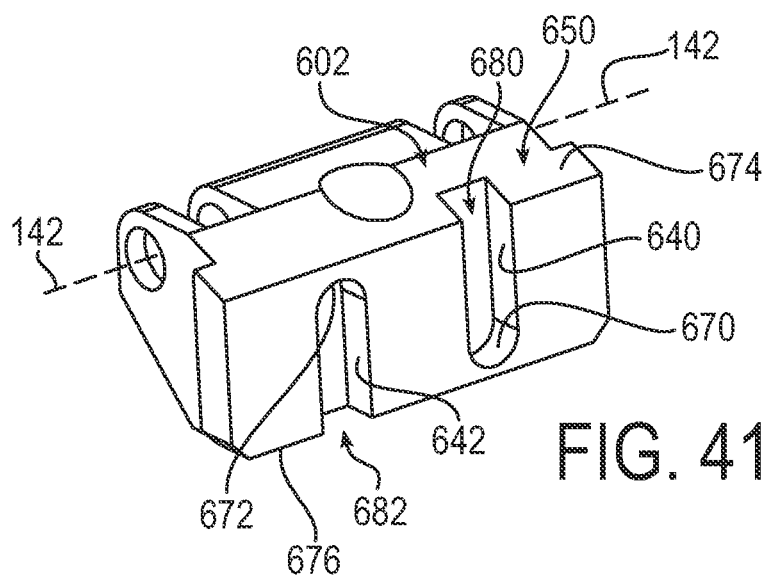
FIG. 41 is a rear perspective view of the adjustable bearing element shown in FIG. 39.
Figure 42:
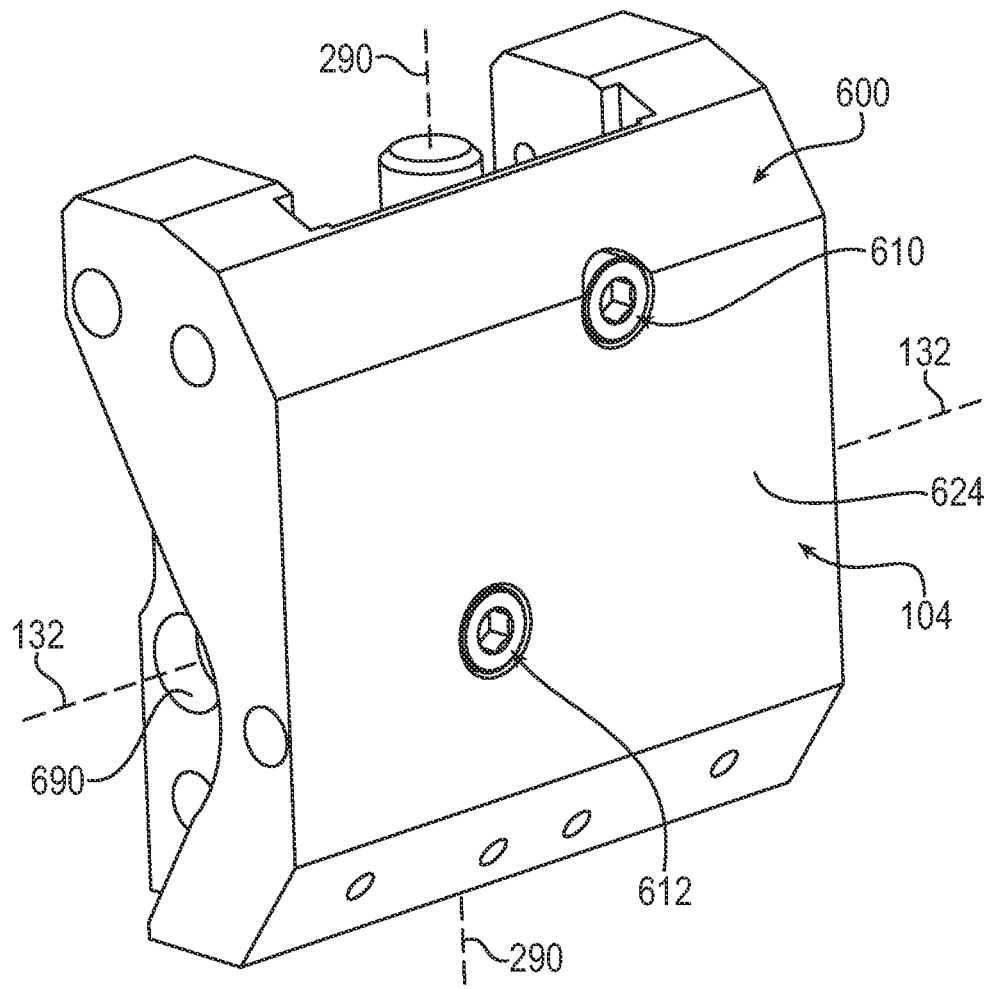
FIG. 42 is a rear perspective view of the load adjustment base shown in FIG. 39.
Figure 43:
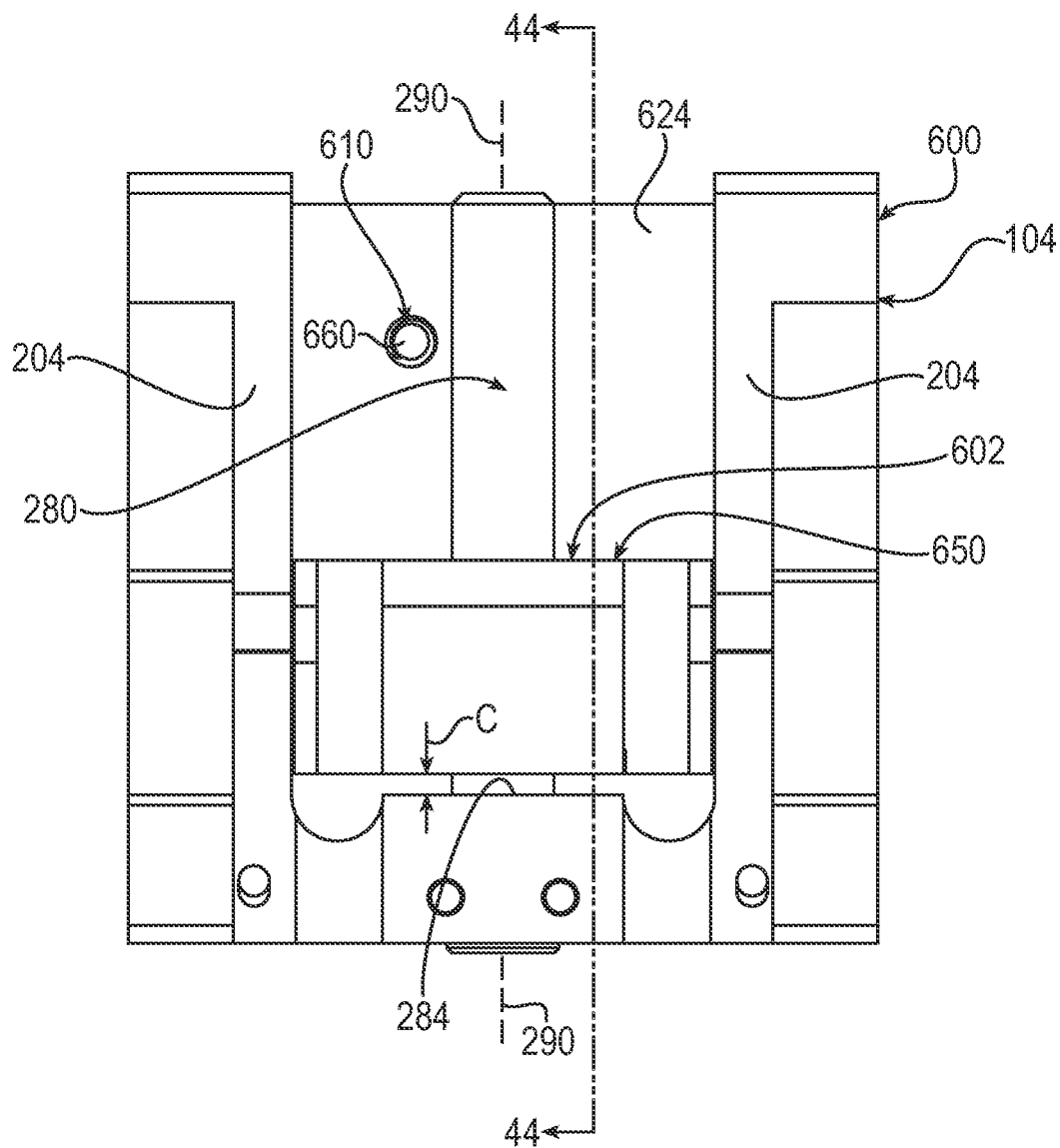
FIG. 43 is a front view of the load adjustment base and adjustable bearing element of FIG. 39.
Figure 44:
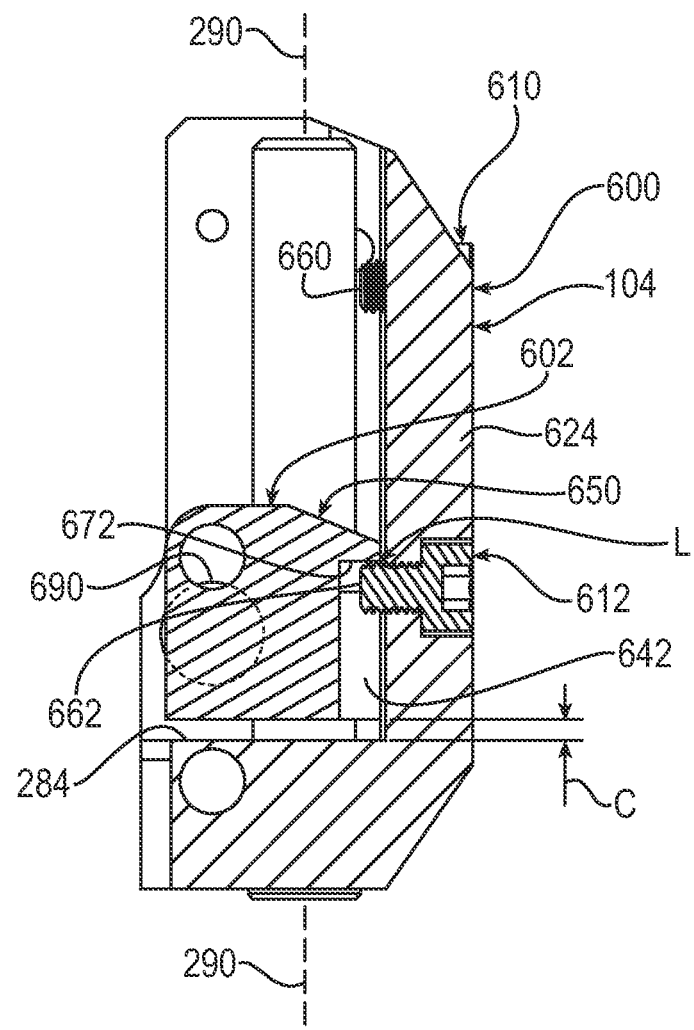
FIG. 44 is a cross section view of the load adjustment base and adjustable bearing element of FIG. 39 as viewed from the plane 44-44 in FIG. 43.
Figure 45:
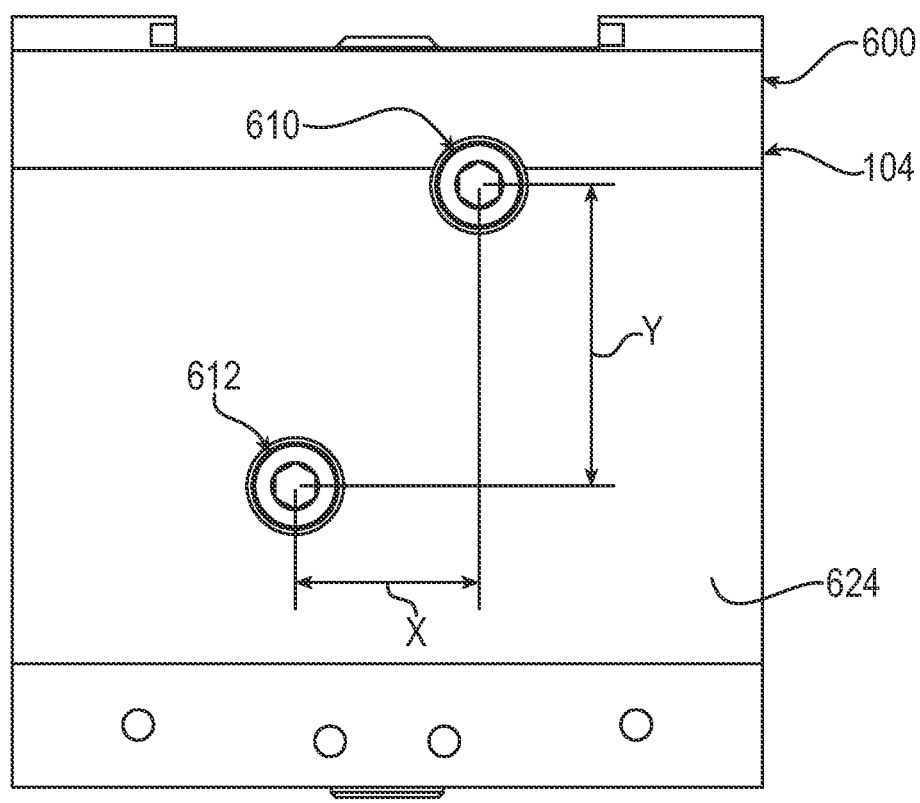
FIG. 45 is a rear view of the load adjustment base shown in FIG. 39.
Figure 46:
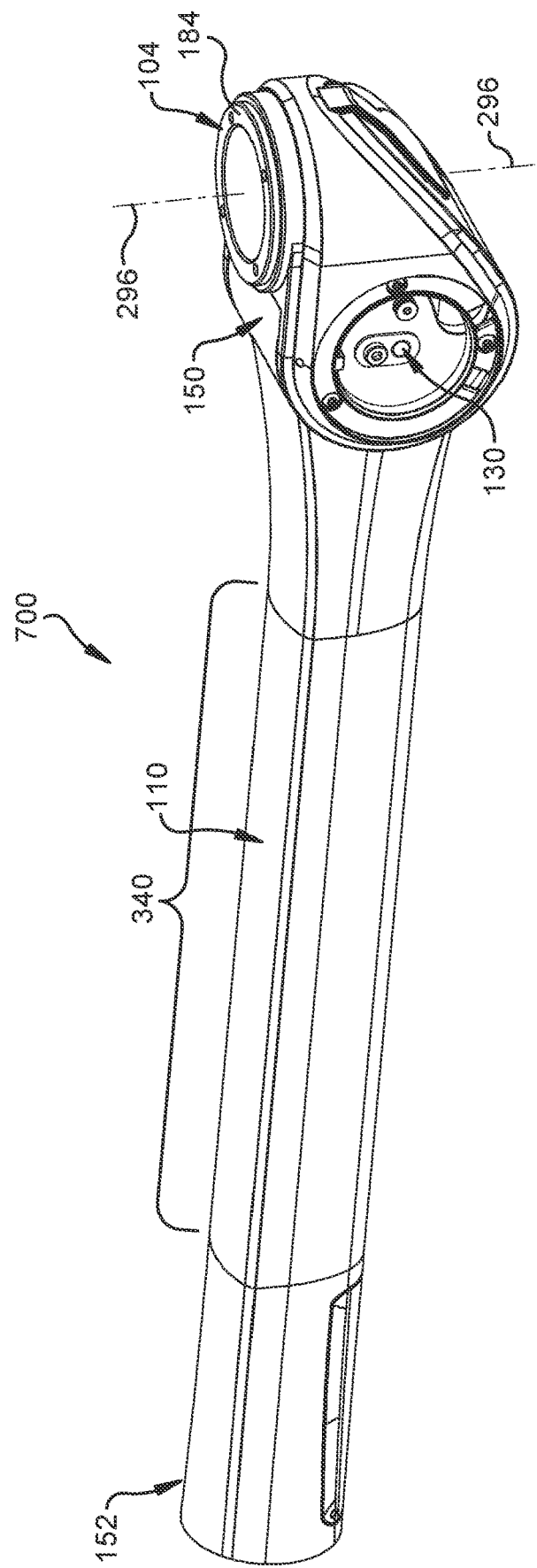
FIG. 46 is a side perspective view of a load balancing arm in accordance with an embodiment of the invention.

Turning to FIGS. 39-45, the load adjustment base 600 and the adjustable bearing element 602 are configured to enable a specific range of adjustment of the adjustable pivot axis 142 of the adjustable bearing element 108 relative to the main pivot axis 132 of the proximal hub 104. As shown in FIGS. 40, 42 and 44, a pair of socket head cap screws 610, 612 are provided in respective threaded openings in a rear wall 624 of the load adjustment base 600. As shown in FIGS. 40 and 45, the centers of the screws 610, 612 are laterally spaced apart a distance X in a direction parallel to the main pivot axis 132, and vertically spaced apart a distance Y in a direction perpendicular to the main pivot axis 132. As shown in FIGS. 41 and 44, a pair of vertically extending slots 640, 642 are provided in a load adjustment nut 650 of the adjustable bearing element 602. The lateral spacing between the vertically extending slots 640, 642 is equal to the lateral spacing Y between the centers of the screws 610, 612. In the illustrative embodiment, the screws 610, 612 and slots 640, 642 are on laterally opposite sides of the central axis 290 of the load adjustment screw 280.

The tips 660, 662 of the respective socket head cap screws 610, 612 protrude forward from the rear wall 624 and are sized to fit within the respective slots 640, 642. One slot 640 has a lower abutment wall 670 and opens upward at a top surface 674 of the load adjustment nut 650 to define a vertical entranceway 680 for the screw 610. The other slot 642 has an upper abutment wall 672 and opens downward at a bottom surface 676 of the load adjustment nut 650 to define a vertical entranceway 682 for the screw 612. The lower and upper abutment walls 670, 672 of the load adjustment nut 650 define the respective upper and lower limits on the range of adjustment of the load adjustment nut 650, and thus, in reference to FIGS. 9, 12, 26, 31 and 32, the upper and lower limits on the range of adjustment of the pin 324 to which the proximal ends 160 of the links 124, 126 are pivotably mounted. This contrasts with the upper limit of the range of adjustment 330 being defined by a top wall of the load adjustment base 196, 530 or an end-of-thread of the load adjustment screw 280, and the lower limit being defined by the bottom wall 284 of the load adjustment base 196, 530.

Thus, as the load adjustment nut 650 moves up and down in the vertical direction as the load adjustment screw 280 is rotated respectively clockwise and counterclockwise, the adjustable pivot axis 142 moves vertically up and down relative to the main pivot axis 132 bound by the respective upper and lower limits on the adjustment range provided by the abutment walls 670, 672 of the load adjustment nut 650. FIGS. 43 and 44 show an example of the lower limit. As will appreciated with reference to FIG. 44, as the load adjustment nut 650 is urged downward, the upper abutment wall 672 of slot 642 eventually abuts the tip 662 of the socket head cap screw 612 thereby preventing further downward movement of the load adjustment nut 650. As will be appreciated, in a similar manner, as the load adjustment nut 650 is urged upward, the lower abutment wall 670 of the slot 640 eventually abuts the tip 660 of the screw 610 to prevent further upward movement of the load adjustment nut 650.

The FIGS. 39-45 embodiment enables a specific range of adjustment of the adjustable pivot axis 142 relative to the main pivot axis 132. For example, by adjusting the lengths of the slots 640, 642 and/or the positions of the upper and lower abutment walls 670, 672, the range of adjustment can be changed without having to change the structure of the load adjustment base 600. In the illustrative embodiment, for example, the lower abutment location, L, is vertically above the topmost portions of the diameters of the openings 690 that accommodate the laterally spaced pins 240 that form the main bearing element 130 (see FIGS. 12 and 31) that defines the main pivot axis 132. When the upper abutment wall 672 has abutted the socket head cap screw 612, the load adjustment nut 650 has reached its lowermost position or "bottomed out" but a clearance gap, C, remains between the bottom surface 694 of the load adjustment nut 650 and the bottom wall 684 of the load adjustment base 600.

It will be appreciated that the quantity of socket head cap screws 610, 612 and corresponding quantity of slots 640, 642 need not be limited to two as shown. For example, a second pair of socket head cap screws and a second pair of slots further laterally spaced apart than the first pair of socket head cap screws 610, 612 and the first pair of slots 640, 642, for a total of four socket head cap screws and four slots, can be provided, where the second pair of socket head cap screws and second pair of slots define a different upper and lower limit on the range of adjustment than that of the first pair of socket head cap screws 610, 612 and first pair of slots 640, 642. It will also be appreciated that the rear wall 624 of the load adjustment base 600 may include a plurality of vertically staggered threaded openings to allow the vertical height of the screws 610, 612 to be changed, thus allowing the corresponding range of adjustment of the adjustable pivot axis 142 relative to the main pivot axis 132 to be changed. It will also be appreciated that either the upper adjustment limit mechanism 610, 640, 670 or the lower adjustment limit mechanism 612, 642, 672 may be omitted and a different limit mechanism substituted therefor; for example, substituting a top wall of the load adjustment base 196, 530 or an end-of-thread of the load adjustment screw 280 for the upper adjustment limit mechanism 610, 640, 670, and/or substituting the bottom wall 284 of the load adjustment base 196, 530 for the lower adjustment limit mechanism 612, 642, 672. Other combinations are also contemplated. It will further be appreciated that protruding elements other than socket head cap screws 610, 612 may be used to fit within the slots 640, 642 to act as limits to the respective abutment walls 670, 672 of the adjustable bearing element 602. For example, rather than socket head cap screws 610, 612 being inserted in respective threaded openings in the rear wall 624 of the load adjustment base 600, clips may be inserted through respective through holes in the rear wall 624, wherein the tips of the clips act as the limits to the respective abutment walls 670, 672.

FIGS. 46-54 show a load balancing arm 700 according to another embodiment of the invention. The load balancing arm 700 is in many respects similar to the above-referenced load balancing arms 100, 500 and consequently the same reference numerals are used to denote structures corresponding to similar structures in the load balancing arms 100, 500. In addition, the foregoing description of the load balancing arms 100, 500 is equally applicable to the load balancing arm 700 except as noted below. Moreover, it will be appreciated upon reading and understanding the specification that aspects of the load balancing arms 100, 500, 700 may be substituted for one another or used in conjunction with one another where applicable.

Figure 47:
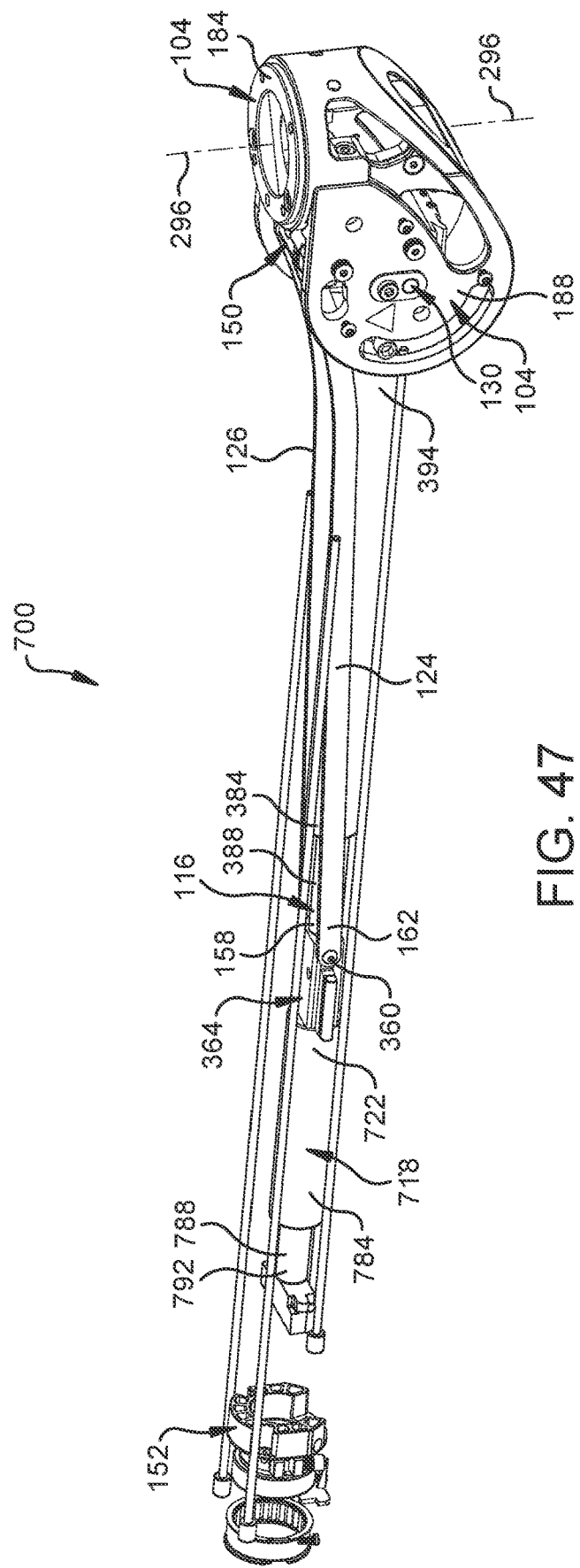
FIG. 47 is a view similar to FIG. 46 with a support arm structure removed to show internal components of the load balancing arm.

Turning then to FIGS. 46-54, there is shown a load balancing arm 700 of the medical device support system 10 in accordance with an embodiment of the invention. The load balancing arm 700 includes a proximal hub 104, an adjustable bearing element 108, a support arm 110, first and second springs 116, 718 and one or more links, two such links 124, 126 in the illustrative embodiment, as shown in FIG. 47. The proximal hub 104 may include a support structure 24 such as the drop tube 24 (see FIG. 1). The proximal hub 104 includes a main bearing element 130 that defines a main pivot axis 132 (see FIGS. 9 and 12-14). The adjustable bearing element 108 defines an adjustable pivot axis 142 that is adjustable relative to the main pivot axis 132. It is contemplated that the pivot axis 142 need not be adjustable relative to the main pivot axis 132 and, accordingly, the adjustable bearing element 108 and the adjustable pivot axis 142 may be referred to herein respectively as a link bearing element 108 and link pivot axis 142. The support arm 110 has a proximal end 150 and a distal end 152. The distal end 152 is configured to support a medical device load 36 (see FIG. 1) and the proximal end 150 is pivotably mounted to the main bearing element 130 for pivotable movement about the main pivot axis 132. Pivotable movement about the main pivot axis 132 raises and lowers the height of the medical device load 36 at the distal end 152.

The first and second springs 116, 718 extend within a cavity 154 (see FIG. 7) of the support arm 110. The first spring 116 is mounted to exert a biasing force between the main pivot axis 132 and a distal end 158 of the first spring 116, and the second spring 718 is mounted to exert a biasing force between a proximal end 722 of the second spring 718 and a wall 728 at the distal end 152 of the support arm 110. The links 124, 126 each have a proximal end 160 and a distal end 162. The proximal end 160 is pivotably mounted to the link bearing element 108 for pivotable movement about the link pivot axis 142 (or, where an adjustable bearing element 108 is provided, pivotably mounted to the adjustable bearing element 108 for pivotable movement about the adjustable pivot axis 142). The distal ends 162 of the links 124, 126 are pivotably mounted to the distal end 158 of the first spring 116 and the proximal end 722 of the second spring 718 such that the biasing forces exerted by the first and second springs 116, 718 are transmitted through the links 124, 126 to the link bearing element 108 thereby to generate a moment about the main pivot axis 132 of the proximal hub 104 that counters a moment generated by the medical device load 36 at the distal end 152 of the support arm 110, thereby balancing the medical device load 36.

Thus, in the load balancing arm 700 according to the present embodiment, there are two springs 116, 718, connected functionally in series, that together provide the load balancing arm 700 with an improved force transmission and a greater load bearing capacity, and thus a greater range of control than if the load balancing arm 700 had only a single spring; and these improvements are realized with minimal or no corresponding increase in the size of the load balancing arm 700. In this regard, it is noted that the FIG. 46 dual spring load balancing arm 700 has the same cross sectional area as that of the FIG. 2 single spring load balancing arm 100. Moreover, the links 124, 126 connect at their proximal ends 160 to the bearing element 108 and at their distal ends 162 to the distal end 158 of the first spring 116. The attachment at the distal end 158 of the first spring 116 allows for a relatively longer link than if connected to the proximal end of the first spring 116, which has been found to allow for a better force transmission and less spring travel resulting in a more balanced load balancing arm 700 throughout the pivotable range of travel of the arm 700.

The proximal end 150 of the support arm 110 of the load balancing arm 700 is identical in structure and function to that of the afore described load balancing arm 100 and thus for brevity further description thereof is omitted.

Turning now to FIGS. 46 and 52-54, the support arm 110 includes an intermediate portion 340 between the proximal end 150 and distal end 152 of the support arm 110. The intermediate portion 340 has a relatively narrower height span than the circular portion 178 of the proximal end 150 of the support arm 110. The links 124, 126 (only link 124 is in view in FIGS. 52-54) have at least one bend that corresponds to the difference in height span between the intermediate portion 340 and the circular portion 178 (see FIG. 9) of the proximal end 150 of the support arm 110. In the illustrative embodiment, the links 124, 126 have one bend and consequently have a J-shape in side view. Other shapes such as S-shape (two bends) are also contemplated. The bend in the links 124, 126 aids in the load balancing arm 700 having a smaller size and lower overall cross section profile than if the links 124, 126 were straight. The smaller size and lower overall cross section profile make the load balancing arm 700 less obstructive in the operating room and improve the laminar airflow around the surface of the load balancing arm 700.

Referring to FIGS. 47-54, like the afore described load balancing arm 100, the load balancing arm 700 includes a carriage slide 364 that is slidable relative to the support arm 110. The distal ends 162 of the links 124, 126 are pivotably mounted to the distal end 158 of the first spring 116 via the carriage slide 364. The pivotable connection may be facilitated by, for example, a pin 360 mounted within the carriage slide 364. The sliding connection between the carriage slide 364 and the support arm 110 for the load balancing arm 700 is identical to that of the carriage slide 364 and support arm 110 for the load balancing arm 100; as such, reference is made again to FIG. 7. As shown in FIG. 7, the carriage slide 364 is slidable within at least one groove 368 in the support arm 110, wherein in the illustrative embodiment there are two such grooves 368 at laterally opposite sides of the support arm 110. The grooves 368 are oriented along an axis that extends radially from and perpendicular to the main pivot axis 132 (see FIGS. 9 and 12-14). The grooves 368 are formed by parallel ribs 370 in the inward facing walls of the support arm 110. The ribs 370, along with a box shape member in the lower portion of the support arm 110, also serve as stiffening members.

The first and second springs 116, 718 of the load balancing arm 700 may be any type of counterbalancing member, and in the illustrative embodiment are, respectively, a compression gas spring 116 and a tension gas spring 718. Like the grooves 368, the first and second springs 116, 718 are oriented along an axis that extends radially from and perpendicular to the main pivot axis 132. In the illustrated embodiment, the first spring 116 is configured to expand and contract along a first axis and the second spring 718 is configured to expand and contract along a second axis, and the first and second axes coincide with one another. Of course, in other embodiments, the first and second springs 116, 718 may expand and contract along respective axes that do not coincide with one another, for example, where other components within the support arm 110 may impede the expansion and contraction of one or both of the first and second springs 116, 71, in which case the first and second axes may be slightly offset from one another or at non-zero angles relative to one another.

The first spring 116 of the load balancing arm 700 is similar in structure and function as the spring 116 of the load balancing arm 100 and, accordingly, reference is made to FIGS. 11, 12 and 15-17 and the corresponding description of the spring 116 of the load balancing arm 100. The first spring 116 has a cylinder 384 and a rod 388. The cylinder 384 has a proximal end wall 390 at a proximal end 394 of the first spring 116 that is coupled to a vertical beam 392 of the support arm 110. As shown in FIG. 11, the vertical beam 392 extends from a top wall 406 to a bottom wall 408 of the support arm 110 and is sufficiently narrow that the links 124, 126 straddle the vertical beam 392 on opposite lateral sides thereof throughout the pivotable range of the load balancing arm 700. The proximal end wall 390 of the cylinder 384 may be coupled to the vertical beam 392 in any suitable manner, for example as by a protrusion 418, shown in FIG. 12, that fits within an opening 420 in the vertical beam 392, shown in FIG. 11. The rod 388 is pivotably mounted to the distal ends 162 of the links 124, 126 via the pin 360 of the afore described carriage slide 364. In operation, the links 124, 126 straddle the first spring 116 on laterally opposite sides of the first spring 116 throughout the pivotable range of the load balancing arm 700.

Details of the second spring 718 are shown in FIGS. 47-51. The second spring 718 has a cylinder 784 and a rod 788. The cylinder 784 is connected to the carriage slide 364 and the rod 788 is connected to the wall 728 of the support arm 110 so that the second spring 718 exerts a biasing force that biases the carriage slide 364 and thus the distal ends 162 of the links 124, 126 toward the distal end 152 of the support arm 110. The cylinder 784 of the second spring 718 has a proximal end wall 790 at the proximal end 722 of the second spring 718 that is connected to the carriage slide 364 such that the proximal end wall 790 and the carriage slide 364 do not separate due to the biasing force. In this way, the proximal end 722 of the second spring 718, the carriage slide 364, and the distal end 158 of the first spring 116 are configured to move together in unison as the carriage slide 364 moves relative to the support arm 110. In the illustrated embodiment, the cylinder 784 and the proximal end wall 790 of the second spring 718, the carriage slide 364, and the rod 388 of the first spring 116 are connected relative to each other and move together in unison as the carriage slide 364 moves relative to the support arm 110. As will be described in greater detail below, the rod 788 of the second spring 718, or more generally a distal end 792 of the second spring 718, is connected to the wall 728 of the support arm 110 such that the rod 788 and the wall 728 do not separate due to the afore described biasing force.

Figure 48:
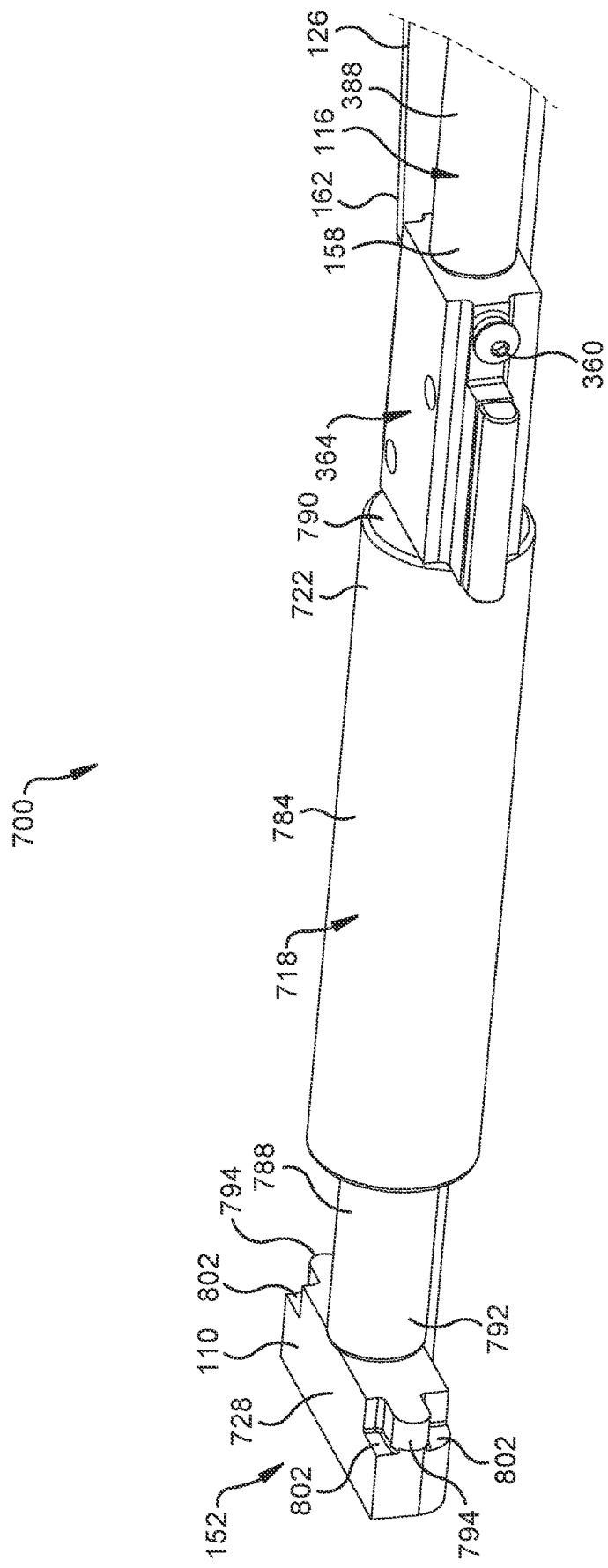
FIG. 48 is an enlarged view of a carriage slide and surrounding components of the FIG. 46 load balancing arm.

The proximal end wall 790 of the cylinder 784 may be connected to the carriage slide 364 to prevent separation therebetween in any suitable manner. Referring to FIG. 48, the proximal end wall 790 of the cylinder 784 is connected to the carriage slide 364 by spot welding although it will be appreciated that brazing, riveting, soldering and/or adhesive glue may additionally or alternately be used. In another form, the proximal end wall 790 may be connected to the carriage slide 364 by an axially extending threaded protrusion of the proximal end wall 790 threadedly engaging a corresponding axially extending threaded opening in the carriage slide 364, or by a protrusion at the proximal end wall 790 being fitted within an opening in the carriage slide 364 in an interference-fit manner. In yet another form, the proximal end wall 790 may be connected to the carriage slide 364 by means of a pivotable connection, for example, by means of a transverse pin mounted within the carriage slide 364 pivotably received in a transverse bore in the proximal end wall 790. In this way, the proximal end 722 of the second spring 718 is pivotably connected to the carriage slide 364 to prevent separation between the proximal end 722 of the second spring 718 and the carriage slide 364 and also to provide tolerance for misalignment among the first and second springs 116, 718 and the carriage slide 364 axially relative to each another.

In the illustrated embodiment, the cylinder 784 of the second spring 718 and the rod 388 of the first spring 116 are connected to axially opposite ends of the carriage slide 364 in the slide direction of the carriage slide 364. Thus, the proximal end 722 of the second spring 718 and the distal end 158 of the first spring 116 are connected to axially opposite ends of the carriage slide 364 in the slide direction of the carriage slide 364. This aids the support arm 110 of the load balancing arm 700 in accommodating the second spring 718 within the cavity 154 (see FIG. 7) of the support arm 110 without a corresponding increase in the cross sectional area (perpendicular to the slide direction) of the support arm 110. As with the rod 388 of the first spring 116, the cylinder 784 of the second spring 718 is pivotably mounted to the distal ends 162 of the links 124, 126 via the pin 360 of the carriage slide 364.

The wall 728 of the support arm 110 may take any suitable form to provide support for the second spring 718 at the distal end 152 of the support arm 110. Referring to FIGS. 48-51, the wall 728 is an internal wall that is supported by and projects inward from a perimeter wall 774 of the support arm 110 that surrounds the first and second springs 116, 718. Laterally opposite convex portions 794 of the wall 728 are slidably fit within laterally opposite internal flanges 796 of the support arm 110. The internal flanges 796 prevent the convex portions 794 and thus the wall 728 from twisting during operation or during assembly of the load balancing arm 700. In the illustrated embodiment, the internal flanges 796 are an axial extension of the ribs 370 that form the grooves 368 (see FIG. 7) within which the carriage slide 364 slides during operation. Thus, the internal flanges 796 of the support arm 110 are oriented along an axis that extends radially from and perpendicular to the main pivot axis 132. In the illustrated embodiment, the internal flanges 796 of the support arm 110 are formed from the same extruded portion of the support arm 110 as the ribs 370 and grooves 368 that slidingly support the carriage slide 364.

The wall 728 also includes axially facing bearing surfaces 802 that abut opposite facing axially facing bearing surfaces 804 of the internal flanges 796. Referring to FIGS. 9, 12, 47-51, the axially facing bearing surfaces 802 of the wall 728 face axially inward toward the main pivot axis 132, and the axially facing bearing surfaces 804 of the internal flanges 796 face axially outward away from the main pivot axis 132. The bearing surfaces 802 of the wall 728 abut the bearing surfaces 804 of the internal flanges 796 to prevent the wall 728, and thus the rod 788 and the distal end 792 of the second spring 718, from moving toward the main pivot axis 132 of the proximal hub 104 or the proximal end 150 of the support arm 110, due to the biasing force exerted by the second spring 718. Thus, the second spring 718 biases the carriage slide 364 toward the wall 728 of the support arm 110 and, in so doing, biases the carriage slide 364 and thus the distal ends 162 of the links 124, 126 toward the distal end 152 of the support arm 110 and correspondingly away from the proximal end 150 of the support arm 110. In another form, the wall 728 may be cast integrally with the support arm 110 as a monolithic structure, or the wall 728 may be fixed to, for example by fasteners, an internal projection of the support arm 110.

The rod 788 of the second spring 718, or the distal end 792 of the second spring 718, may be connected to the wall 728 to prevent separation therebetween in any suitable manner. Referring to FIG. 48, the rod 788 of the second spring 718, in the illustrated embodiment also the distal end 792 of the second spring 718, is connected to the wall 728 by spot welding although it will be appreciated that brazing, riveting, soldering and/or adhesive glue may additionally or alternately be used. In another form, the rod 788 of the second spring 718 may be connected to the wall 728 by a threaded portion of the distal end of the rod 788 threadedly engaging a corresponding axially extending threaded opening in the wall 728, or by the distal end of the rod 788 being fitted within an opening in the wall 728 in an interference-fit manner. In yet another form, the rod 788 may be connected to the wall 728 by means of a pivotable connection, for example, by means of a transverse pin mounted within the wall 728 pivotably received in a transverse bore in the rod 788. In this way, the distal end 792 of the second spring 718 is pivotably connected to the wall 728 to prevent separation between the distal end 792 of the second spring 718 and the wall 728 and also to provide tolerance for misalignment among the first and second springs 116, 718, the carriage slide 364, and the wall 728 axially relative to each another.

Figure 49:
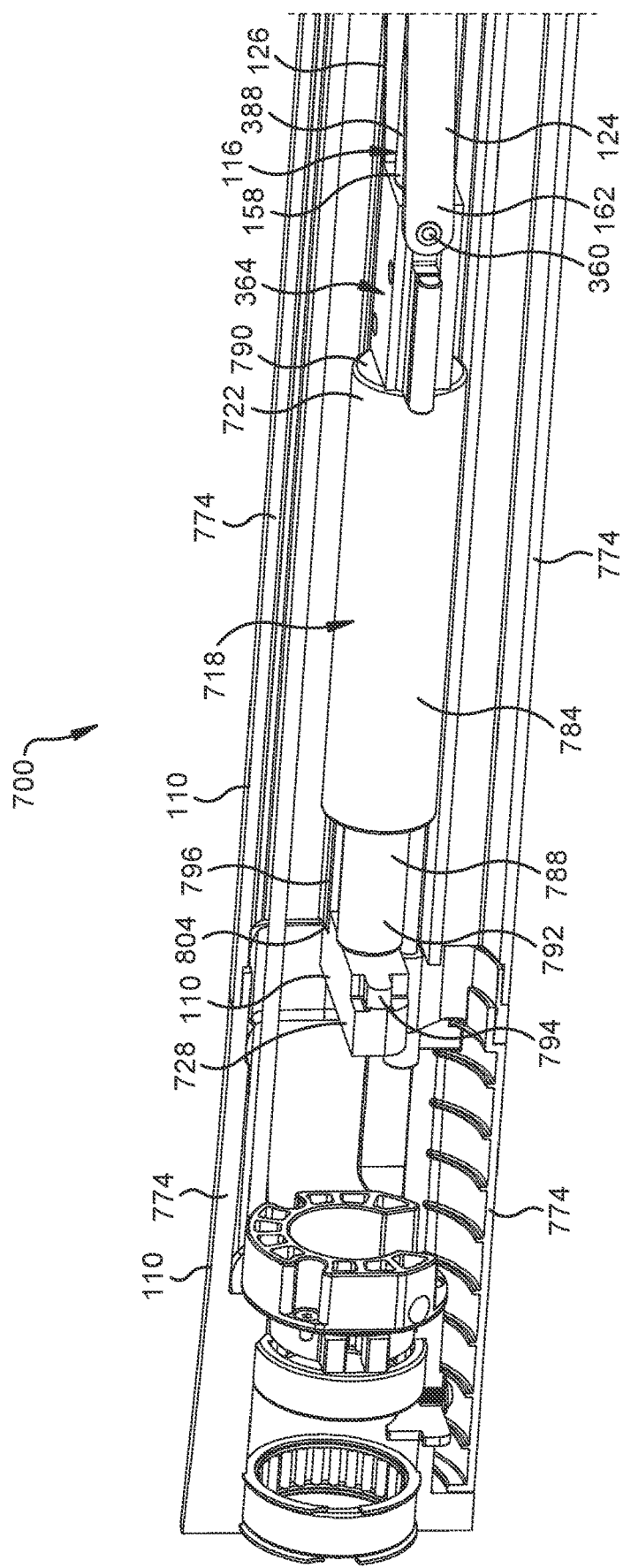
FIG. 49 is a perspective view of the distal end of the FIG. 46 load balancing arm in a substantially horizontal position, with a cover removed to show internal components of the load balancing arm.
Figure 50:
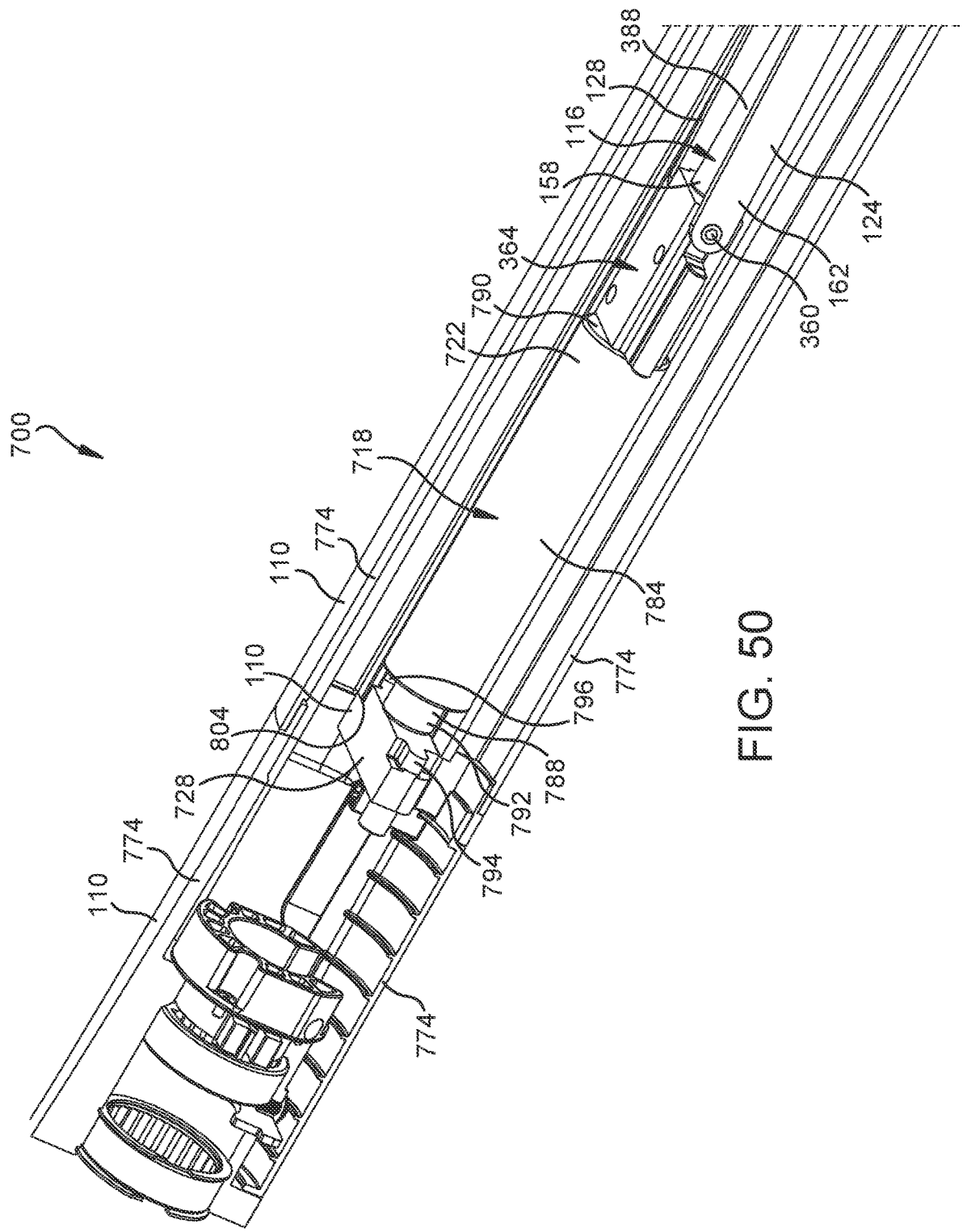
FIG. 50 is a perspective view of the distal end of the FIG. 46 load balancing arm in a position upward from horizontal, with a cover removed to show internal components of the load balancing arm.
Figure 51:
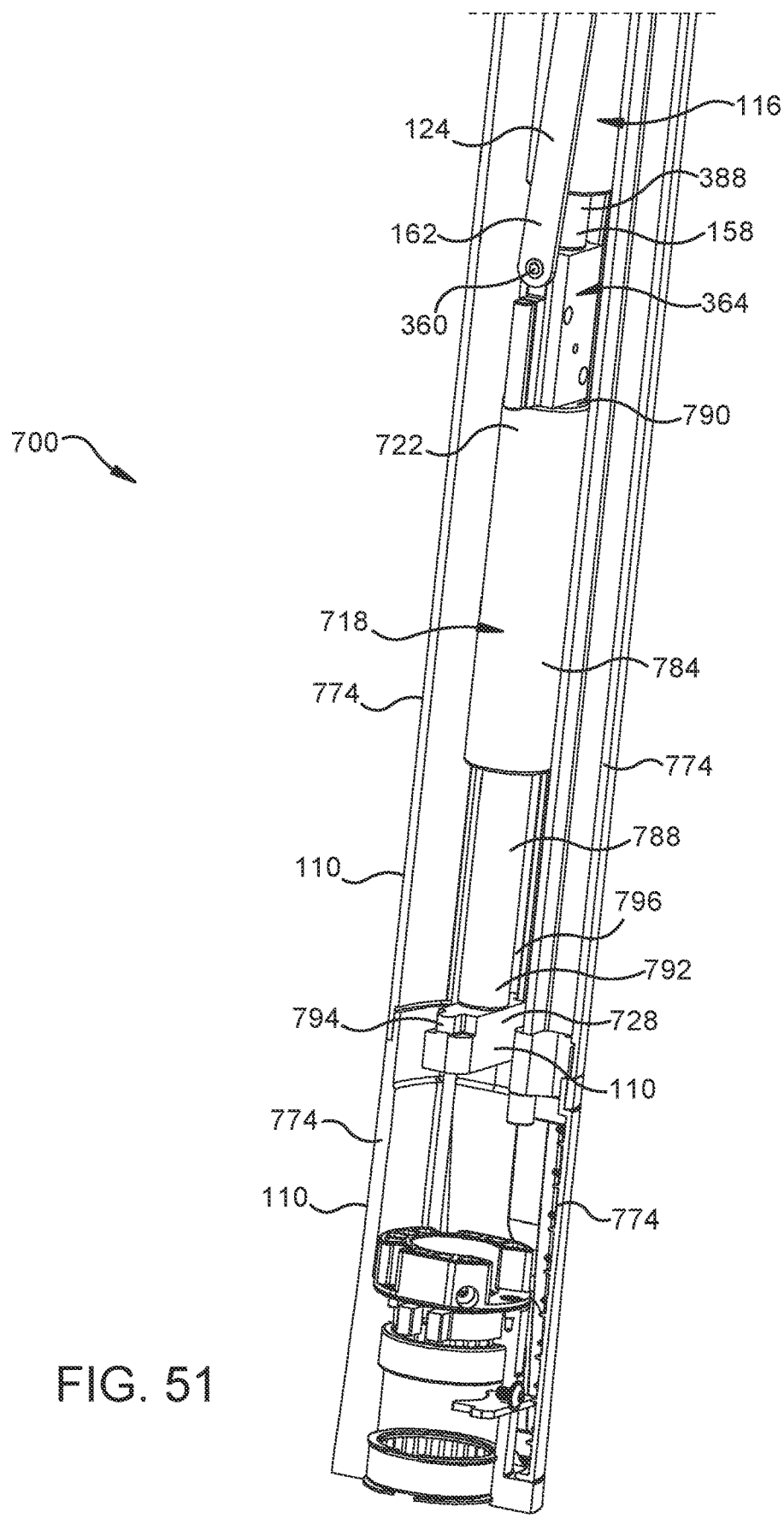
FIG. 51 is a perspective view of the distal end of the FIG. 46 load balancing arm in a position downward from horizontal, with a cover removed to show internal components of the load balancing arm.
Figure 52:
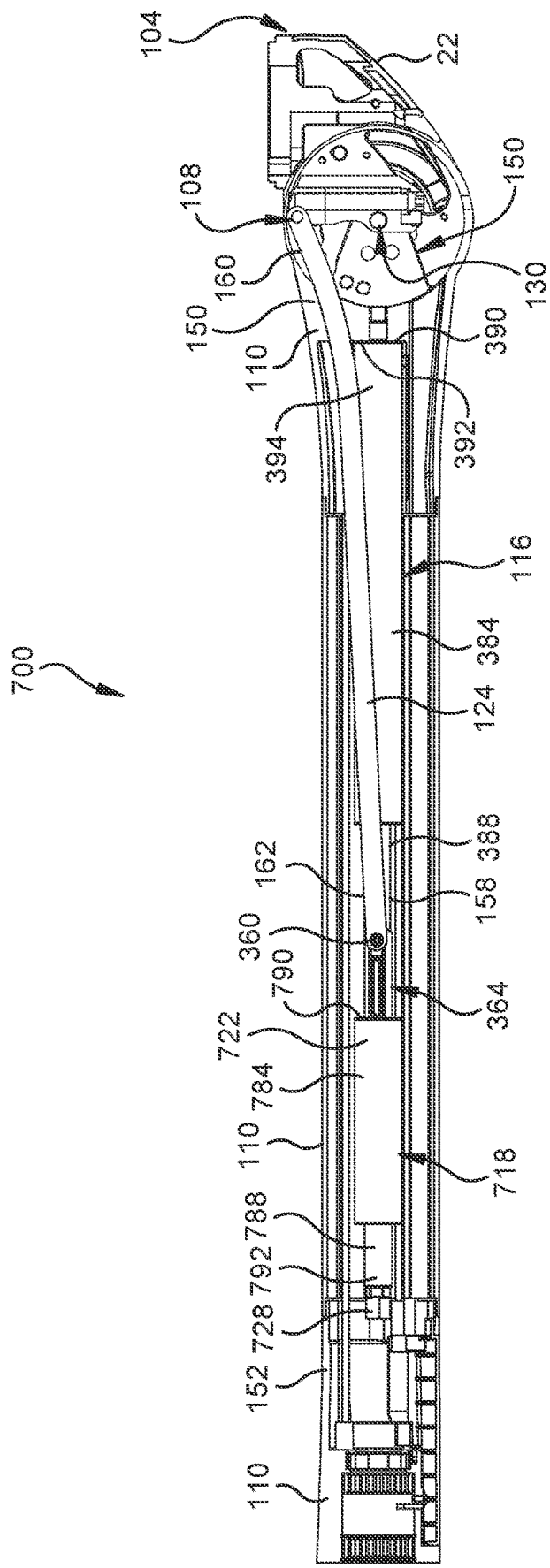
FIG. 52 is a side cross section view of the FIG. 46 load balancing arm in a substantially horizontal position, showing internal components of the load balancing arm.
Figure 53:
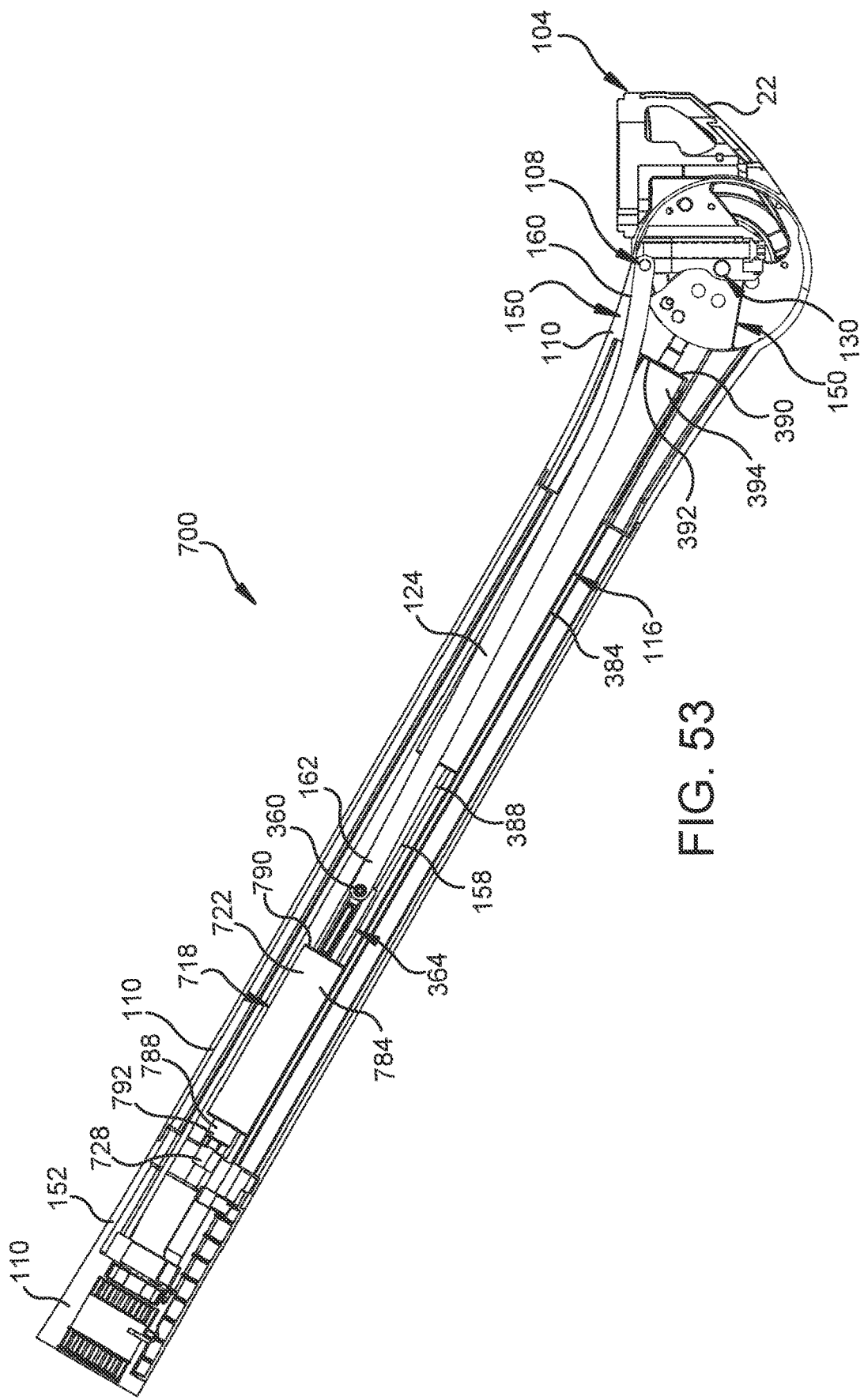
FIG. 53 is a side cross section view of the FIG. 46 load balancing arm in a position upward from horizontal, showing internal components of the load balancing arm.
Figure 54:
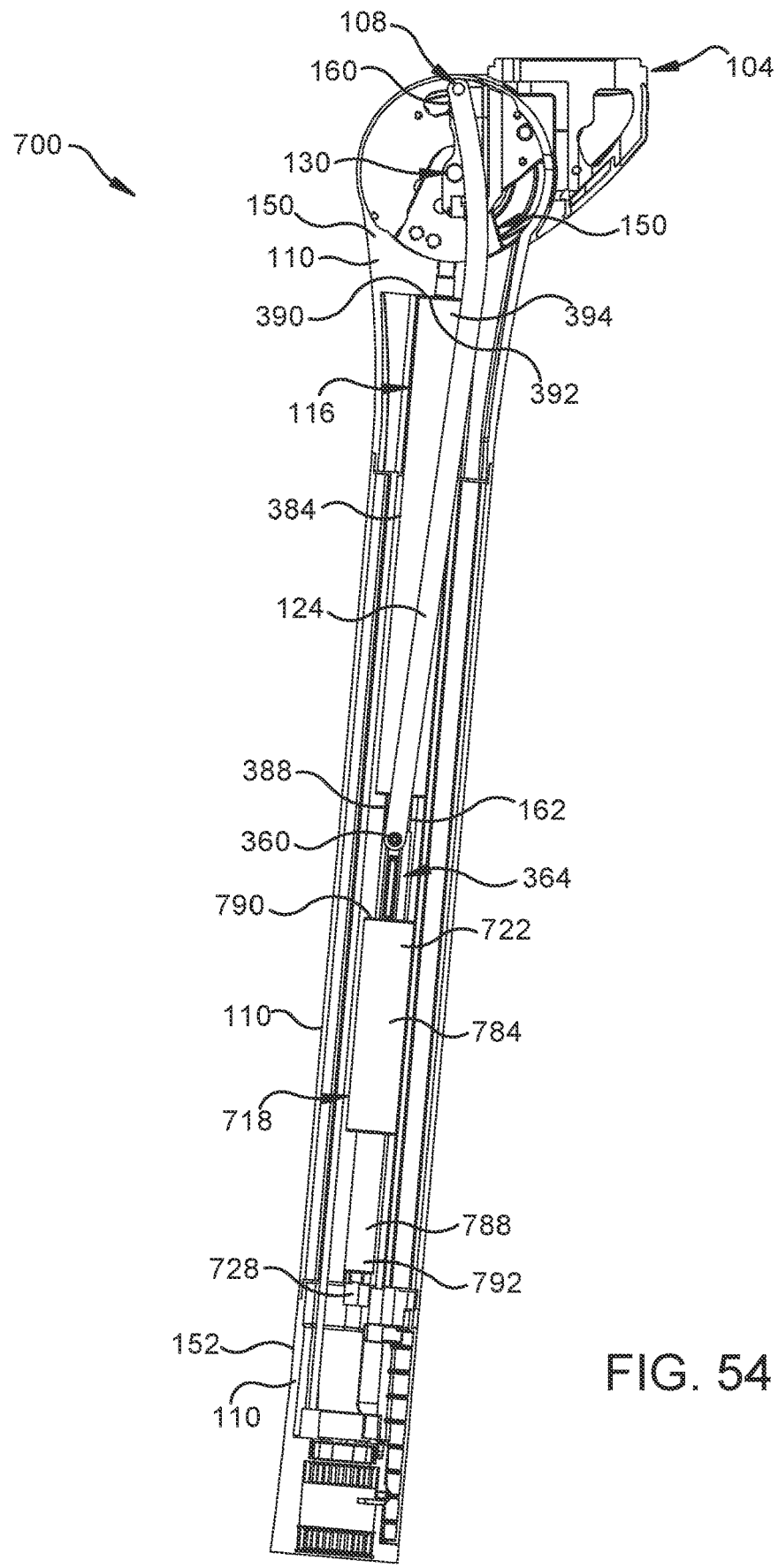
FIG. 54 is a side cross section view of the FIG. 46 load balancing arm in a position downward from horizontal, showing internal components of the load balancing arm.

Reference is now made to FIGS. 52-54, which show the load balancing arm 700 in three different vertical positions, and FIGS. 49-51, which show the distal ends 162 of the links 124, 126 relative to the distal end 152 of the support arm 110 in the three respective vertical positions, as well as the corresponding biasing effects of the first and second springs 116, 718 in the three respective vertical positions. The links 124, 126 are shown adjusted to their maximum height in FIGS. 49-54 (the height from axis 142 to axis 132 in FIG. 12), thereby maximizing the moment, or mechanical advantage, of the load balancing arm 700.

In FIGS. 49 and 52, the support arm 110 is in a substantially horizontal position. Here, the first spring 116 is shown exerting a biasing force between the main pivot axis 132 and the distal end 158 of the first spring 116, and the second spring 718 is shown exerting a biasing force between the proximal end 722 of the second spring 718 and the wall 728 at the distal end 152 of the support arm 110. In the present embodiment, as the first spring 116 is a tension spring, the first spring 116 biases the distal ends 162 of the links 124, 126 toward the distal end 152 of the support arm 110 and thus away from the proximal end 150 of the support arm 110 and away from the main pivot axis 132. Also, as the second spring 718 is a compression spring 718 in the present embodiment, the second spring 718 likewise biases the distal ends 162 of the links 124, 126 away from the proximal end 150 of the support arm 110 and away from the main pivot axis 132. Thus, both the first spring 116 and the second spring 718 contribute to the biasing force that biases the distal ends 162 of the links 124, 126 away from the proximal end 150 of the support arm 110 and away from the main pivot axis 132. As the distal ends 162 of the links 124, 126 are pivotably mounted to the distal end 158 of the first spring 116 and the proximal end 722 of the second spring 718, the biasing forces exerted by the first and second springs 116, 718 are transmitted through the links 124, 126 to the link bearing element 108 thereby to generate a moment about the main pivot axis 132 of the proximal hub 104 that counters a moment generated by the medical device load at the distal end 152 of the support arm 110.

In FIGS. 50 and 53, the support arm 110 is shown pivoted about the main pivot axis 132 about 30 degrees upward relative to horizontal. As compared to FIGS. 49 and 52, the first spring 116 in FIGS. 50 and 53 is shorter in length from its proximal end 394 to its distal end 158 and the second spring 718 is greater in length from its proximal end 722 to its distal end 792. Accordingly, in this position, the biasing force that the first spring 116 exerts to bias the distal ends 162 of the links 124, 126 toward the distal end 152 of the support arm 110 is less than that shown in FIGS. 49 and 52, and the biasing force that the second spring 718 exerts to bias the distal ends of the links 124, 126 toward the distal end 152 of the support arm 110 is less than that shown in FIGS. 49 and 52.

In FIGS. 51 and 54, the support arm 110 is shown pivoted about the main pivot axis 132 about 85 degrees downward from horizontal. As compared to FIGS. 49 and 52, the first spring 116 in FIGS. 51 and 54 is greater in length from its proximal end 394 to its distal end 158 and the second spring 718 is shorter in length from its proximal end 722 to its distal end 792. Accordingly, in this position, the biasing force that the first spring 116 exerts to bias the distal ends 162 of the links 124, 126 toward the distal end 152 of the support arm 110 is greater than that shown in FIGS. 49 and 52, and the biasing force that the second spring 718 exerts to bias the distal ends of the links 124, 126 toward the distal end 152 of the support arm 110 is greater than that shown in FIGS. 49 and 52.

As will be appreciated, then, the support arm 110 has an angle of rotation about the main pivot axis 132 of about 30 degrees upward from horizontal to about 85 degrees downward from horizontal.

In the FIGS. 47-54 embodiment, the first spring 116 includes a compression spring having the cylinder 384 and the rod 388 wherein the cylinder 384 includes the proximal end 394 of the first spring 116 and the rod 388 includes the distal end 158 of the first spring 116. This need not be the case and other embodiments are contemplated. For example, the cylinder 384 and rod 388 may be switched so that the cylinder 384 includes the distal end 158 of the first spring 116 and the rod 388 includes the proximal end 394 of the first spring 116. Also, in the FIGS. 47-54 embodiment, the second spring 718 includes a tension spring having the cylinder 784 and the rod 788 wherein the cylinder 784 includes the proximal end 722 of the second spring 718 and the rod 788 includes the distal end 792 of the second spring 718. This too need not be the case and other embodiments are contemplated. For example, the cylinder 784 and rod 788 may be switched so that the cylinder 784 includes the distal end 792 of the second spring 718 and the rod 788 includes the proximal end 722 of the second spring 718.

FIGS. 55-66 show a load balancing arm 900 according to another embodiment of the invention. The load balancing arm 900 is in many respects similar to the above-referenced load balancing arms 100, 500, 700 and consequently the same reference numerals are used to denote structures corresponding to similar structures in the load balancing arms 100, 500, 700. In addition, the foregoing description of the load balancing arms 100, 500, 700 is equally applicable to the load balancing arm 900 except as noted below. Moreover, it will be appreciated upon reading and understanding the specification that aspects of the load balancing arms 100, 500, 700, 900 may be substituted for one another or used in conjunction with one another where applicable.

Figure 55:
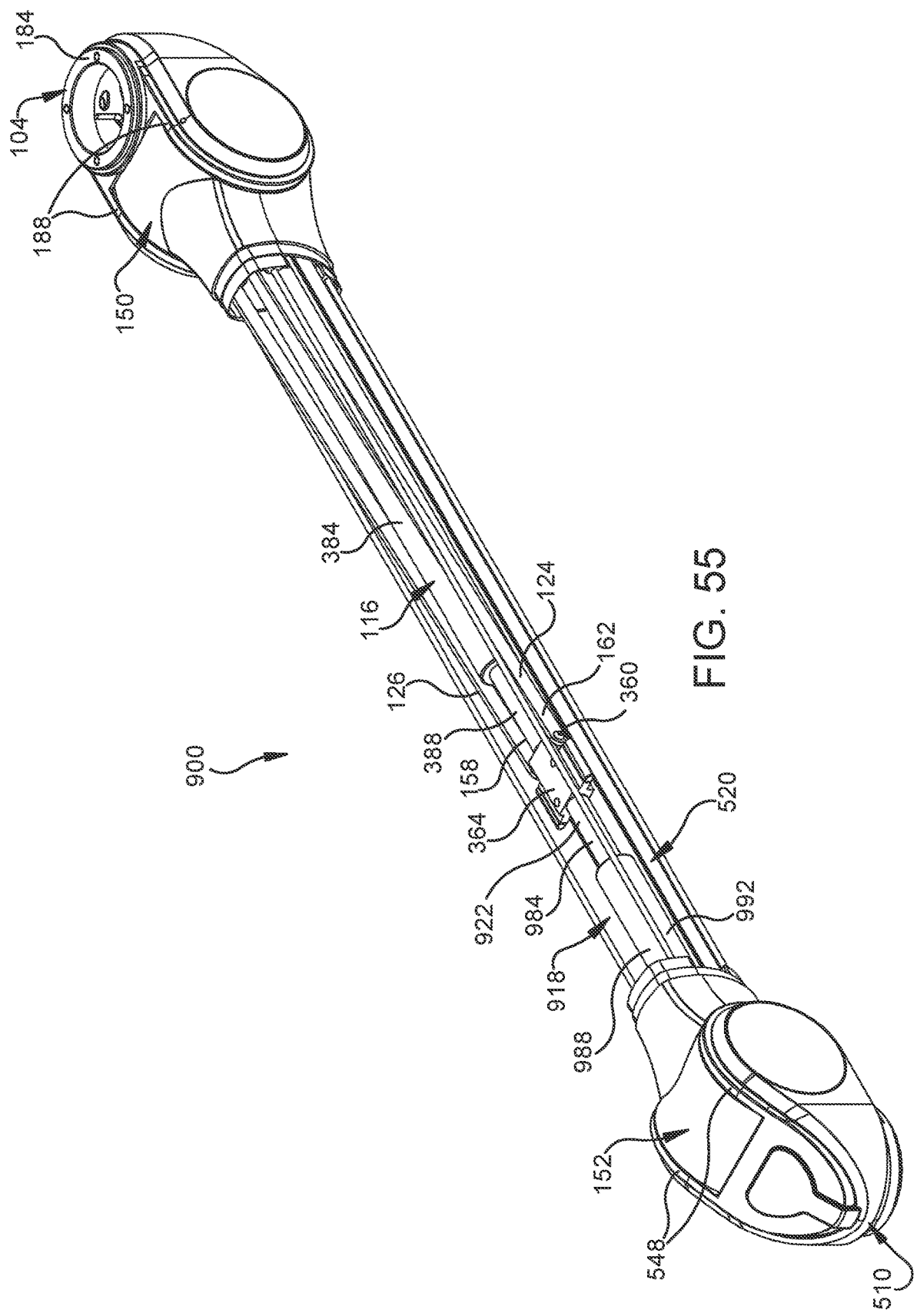
FIG. 55 is a top perspective view of a load balancing arm in accordance with another embodiment of the invention, with a support arm structure removed to show internal components of the load balancing arm.
Figure 56:
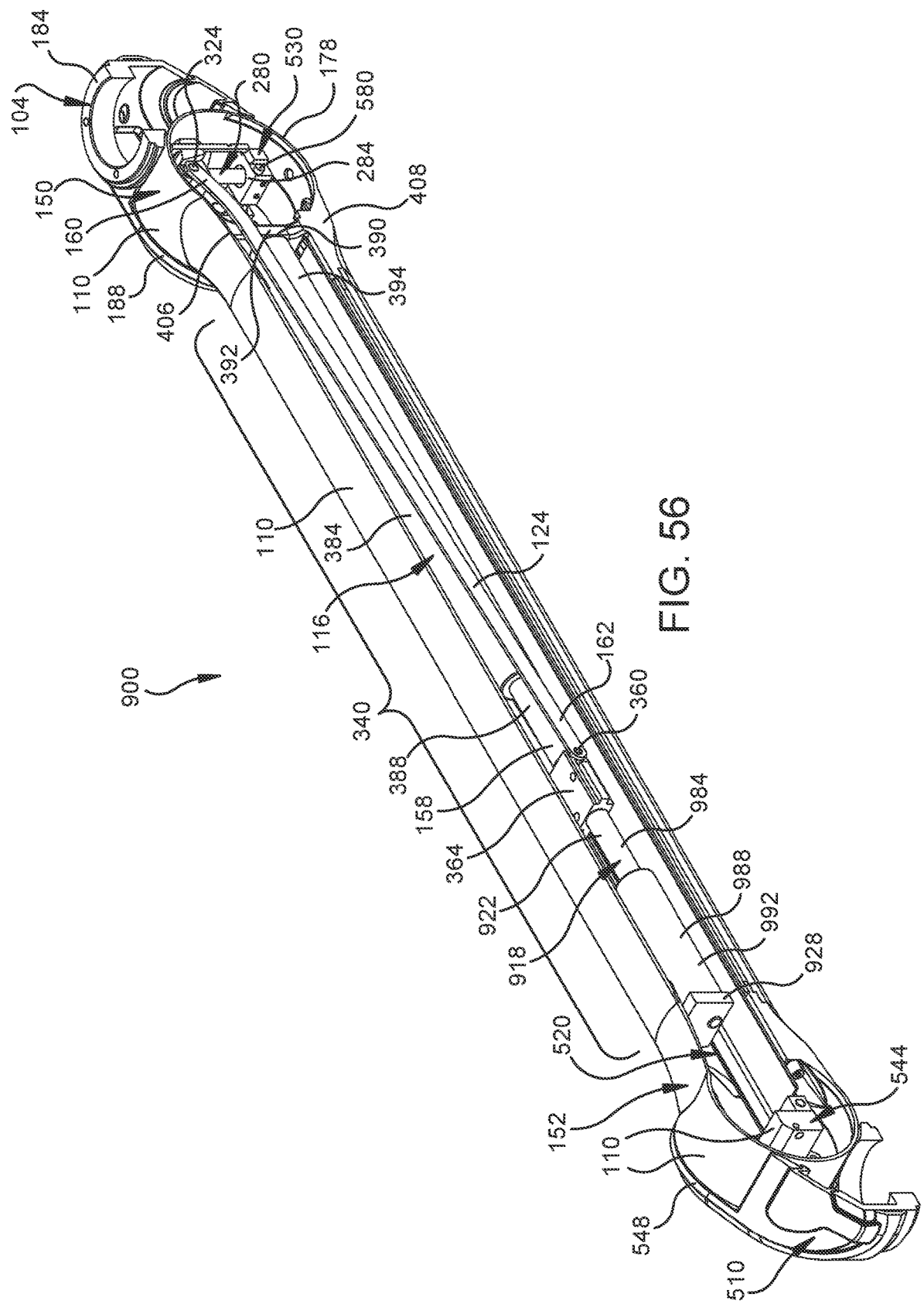
FIG. 56 is a partial top perspective view of the FIG. 55 load balancing arm, shown in partial cross section to show internal components of the load balancing arm.
Figure 57:
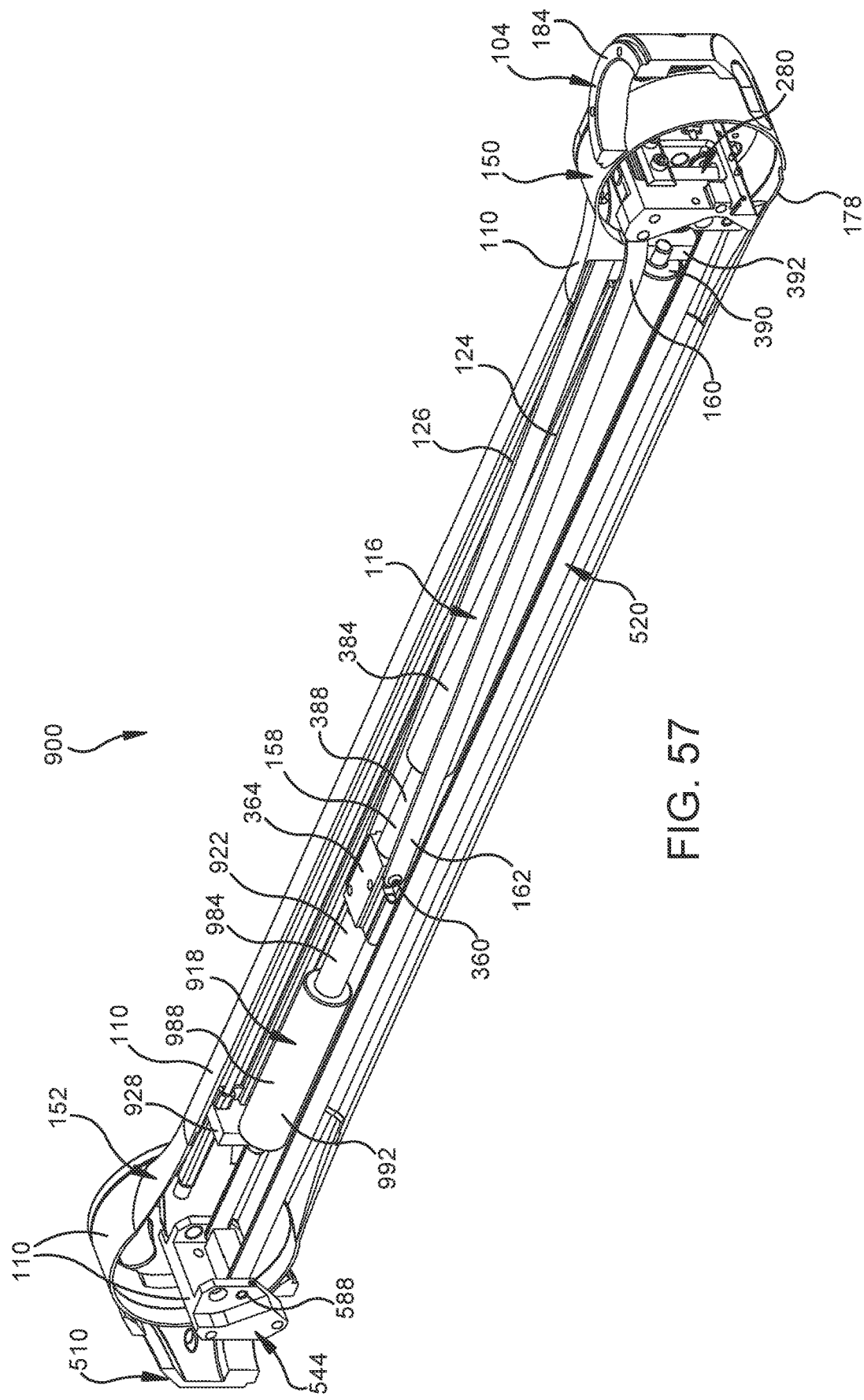
FIG. 57 is a partial top perspective view of the FIG. 55 load balancing arm, shown in partial cross section to show internal components of the load balancing arm.
Figure 60:
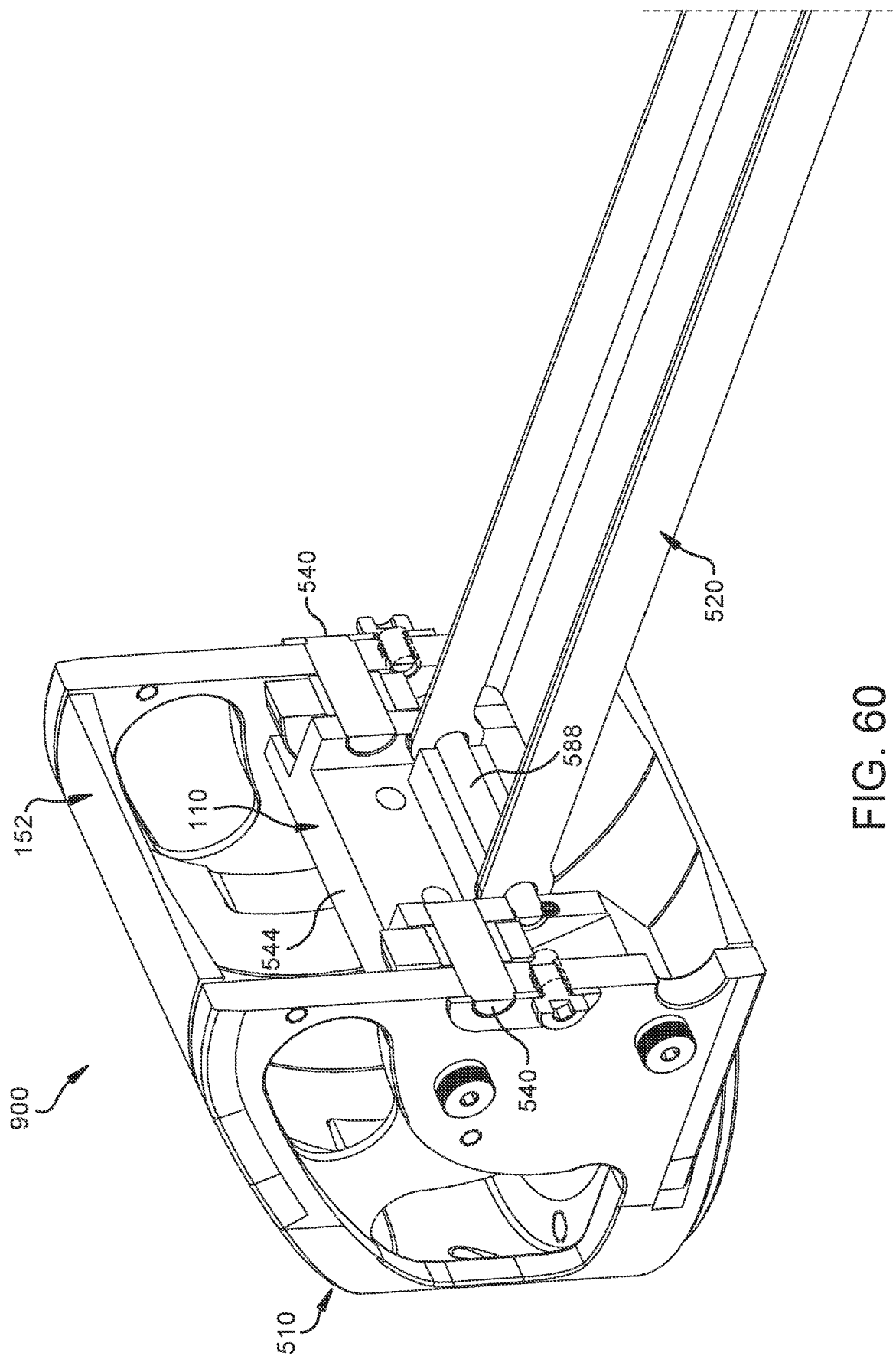
FIG. 60 is a partial cross section perspective view of a distal end of the FIG. 55 load balancing arm, showing internal components of the load balancing arm.

Turning then to FIGS. 55-66, there is shown a load balancing arm 900 of the medical device support system 10 in accordance with an embodiment of the invention. The load balancing arm 900 includes a proximal hub 104, an adjustable bearing element 108, a support arm 110, first and second springs 116, 918 and one or more links, two such links 124, 126 in the illustrative embodiment, as shown in FIG. 55. The proximal hub 104 may include a support structure 24 such as the drop tube 24 (see FIG. 1). The proximal hub 104 includes a main bearing element 130 that defines a main pivot axis 132 (see FIGS. 26 and 33). The adjustable bearing element 108 defines an adjustable pivot axis 142 that is adjustable relative to the main pivot axis 132. It is contemplated that the pivot axis 142 need not be adjustable relative to the main pivot axis 132 and, accordingly, the adjustable bearing element 108 and the adjustable pivot axis 142 may be referred to herein respectively as a link bearing element 108 and link pivot axis 142. The support arm 110 has a proximal end 150 and a distal end 152. The distal end 152 is pivotably mounted to the distal hub 510, which, in turn, is configured to support a medical device load 36 (see FIG. 1). The proximal end 150 is pivotably mounted to the main bearing element 130 for pivotable movement about the main pivot axis 132. The pivotable movement about the main pivot axis 132 raises and lowers the height of the medical device load 36 at the distal end 152.

The first and second springs 116, 918 extend within a cavity 154 (see FIG. 29) of the support arm 110. The first spring 116 is mounted to exert a biasing force between the main pivot axis 132 and a distal end 158 of the first spring 116, and the second spring 918 is mounted to exert a biasing force between a proximal end 922 of the second spring 918 and a wall 928 at the distal end 152 of the support arm 110. The links 124, 126 each have a proximal end 160 and a distal end 162. The proximal end 160 is pivotably mounted to the link bearing element 108 for pivotable movement about the link pivot axis 142 (or, where an adjustable bearing element 108 is provided, pivotably mounted to the adjustable bearing element 108 for pivotable movement about the adjustable pivot axis 142). The distal ends 162 of the links 124, 126 are pivotably mounted to the distal end 158 of the first spring 116 and the proximal end 922 of the second spring 918 such that the biasing forces exerted by the first and second springs 116, 918 are transmitted through the links 124, 126 to the link bearing element 108 thereby to generate a moment about the main pivot axis 132 of the proximal hub 104 that counters a moment generated by the medical device load 36 at the distal end 152 of the support arm 110, thereby balancing the medical device load 36.

Thus, in the load balancing arm 900 according to the present embodiment, there are two springs 116, 918, connected functionally in series, that together provide the load balancing arm 900 with an improved force transmission and a greater load bearing capacity, and thus a greater range of control than if the load balancing arm 900 had only a single spring; and these improvements are realized with minimal or no corresponding increase in the size of the load balancing arm 900. In this regard, it is noted that the FIG. 55 dual spring load balancing arm 900 has the same cross sectional area as that of the FIG. 21 single spring load balancing arm 500. Moreover, the links 124, 126 connect at their proximal ends 160 to the bearing element 108 and at their distal ends 162 to the distal end 158 of the first spring 116. The attachment at the distal end 158 of the first spring 116 allows for a relatively longer link than if connected to the proximal end of the first spring 116, which has been found to allow for a better force transmission and less spring travel resulting in a more balanced load balancing arm 900 throughout the pivotable range of travel of the arm 900.

The proximal end 150 of the support arm 110 of the load balancing arm 900 is identical in structure and function to that of the afore described load balancing arm 500 and thus for brevity further description thereof is omitted.

Figure 64:
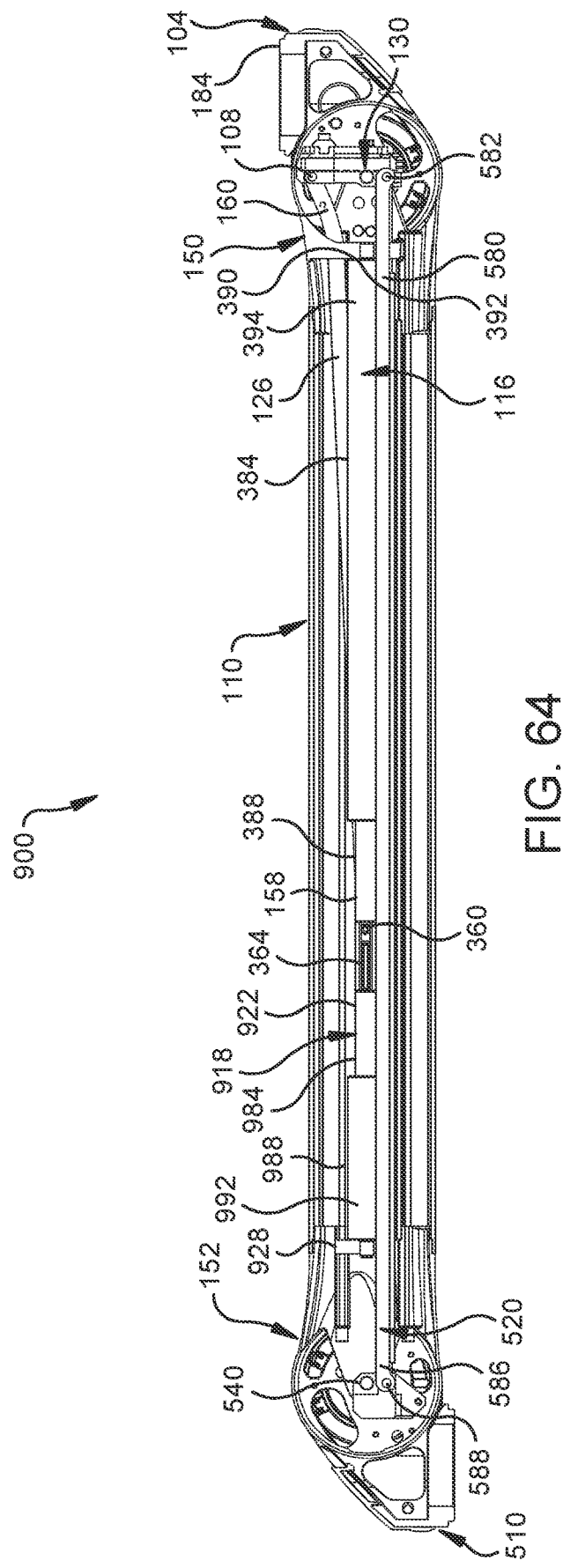
FIG. 64 is a side cross section view of the FIG. 55 load balancing arm in a substantially horizontal position, showing internal components of the load balancing arm.
Figure 65:
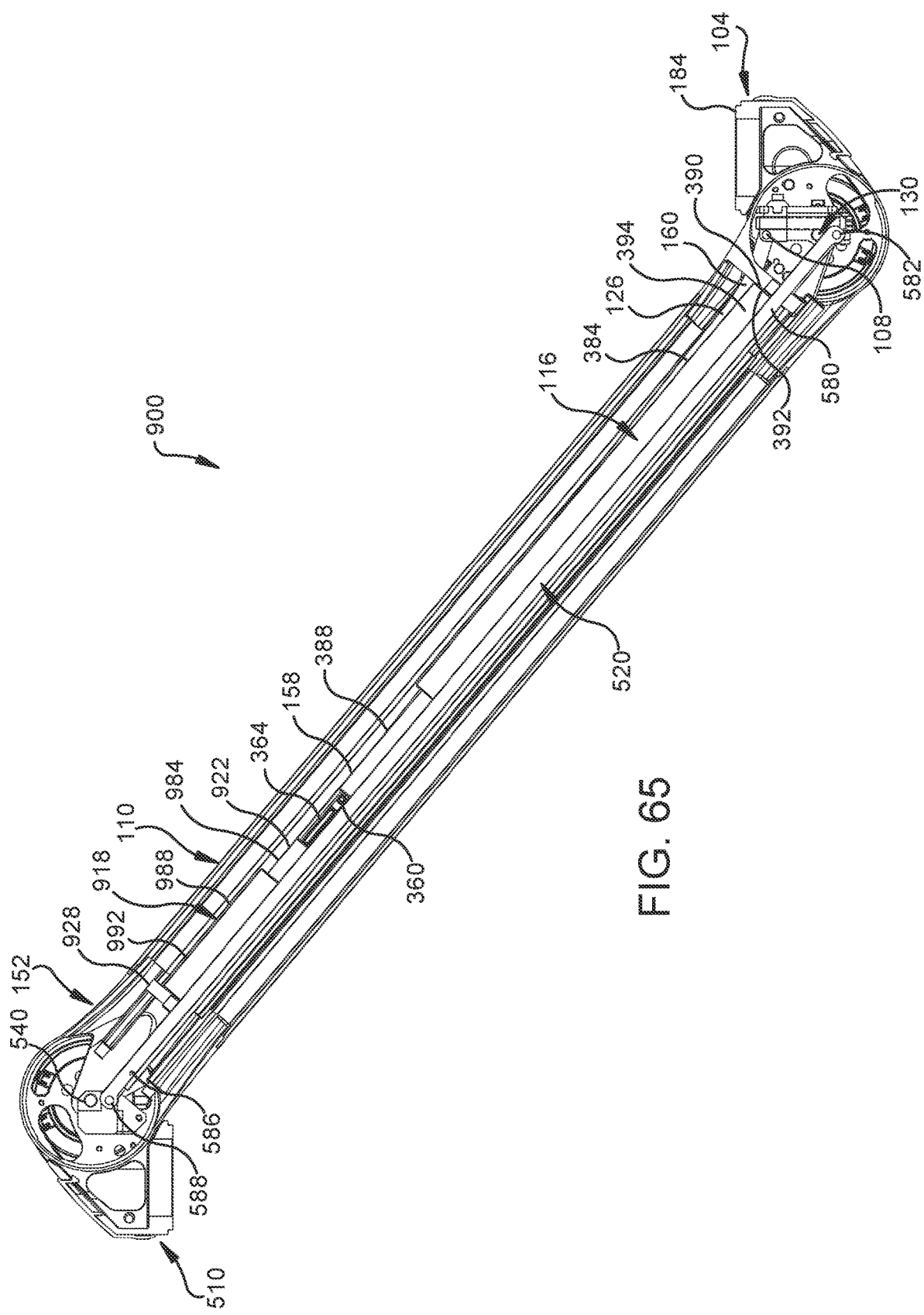
FIG. 65 is a side cross section view of the FIG. 55 load balancing arm in a position upward from horizontal, showing internal components of the load balancing arm.
Figure 66:
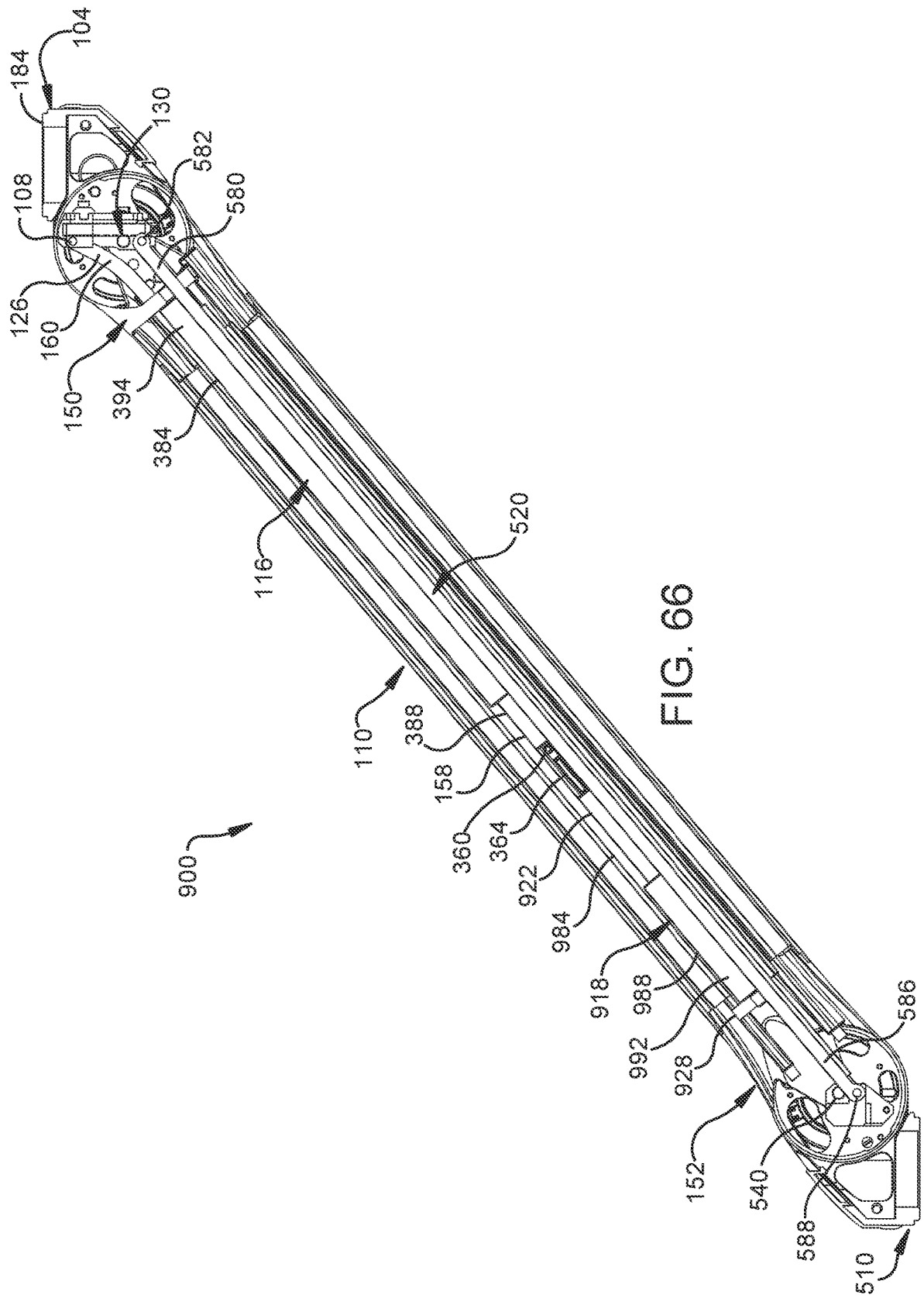
FIG. 66 is a side cross section view of the FIG. 55 load balancing arm in a position downward from horizontal, showing internal components of the load balancing arm.

Turning now to FIGS. 56 and 64-66, the support arm 110 includes an intermediate portion 340 between the proximal end 150 and distal end 152 of the support arm 110. The intermediate portion 340 has a relatively narrower height span than the circular portion 178 of the proximal end 150 of the support arm 110. The links 124, 126 (only link 126 is shown in FIGS. 64-66) have at least one bend that corresponds to the difference in height span between the intermediate portion 340 and the circular portion 178 (see FIG. 22) of the proximal end 150 of the support arm 110. In the illustrative embodiment, the links 124, 126 have one bend and consequently have a J-shape in side view. Other shapes such as S-shape (two bends) are also contemplated. The bend in the links 124, 126 aids in the load balancing arm 900 having a smaller size and lower overall cross section profile than if the links 124, 126 were straight. The smaller size and lower overall cross section profile make the load balancing arm 900 less obstructive in the operating room and improve the laminar airflow around the surface of the load balancing arm 900.

Referring to FIGS. 55-66, like the afore described load balancing arm 500, the load balancing arm 900 includes a carriage slide 364 that is slidable relative to the support arm 110. The distal ends 162 of the links 124, 126 are pivotably mounted to the distal end 158 of the first spring 116 via the carriage slide 364. The pivotable connection may be facilitated by, for example, a pin 360 mounted within the carriage slide 364. The sliding connection between the carriage slide 364 and the support arm 110 for the load balancing arm 900 is identical to that of the carriage slide 364 and support arm 110 for the load balancing arm 500; as such, reference is made again to FIG. 29. As shown in FIG. 29, the carriage slide 364 is slidable within at least one groove 368 in the support arm 110, wherein in the illustrative embodiment there are two such grooves 368 at laterally opposite sides of the support arm 110. The grooves 368 are oriented along an axis that extends radially from and perpendicular to the main pivot axis 132 (see FIGS. 26 and 33). The grooves 368 are formed by parallel ribs 370 in the inward facing walls of the support arm 110. The ribs 370, along with a horizontal cross beam the bottom portion of the support arm 110, also serve as stiffening members.

The first and second springs 116, 918 of the load balancing arm 900 may be any type of counterbalancing member, and in the illustrative embodiment are, respectively, a compression gas spring 116 and a tension gas spring 918. Like the grooves 368, the first and second springs 116, 918 are oriented along an axis that extends radially from and perpendicular to the main pivot axis 132. In the illustrated embodiment, the first spring 116 is configured to expand and contract along a first axis and the second spring 918 is configured to expand and contract along a second axis, and the first and second axes coincide with one another. Of course, in other embodiments, the first and second springs 116, 918 may expand and contract along respective axes that do not coincide with one another, for example, where other components within the support arm 110 may impede the expansion and contraction of one or both of the first and second springs 116, 918, in which case the first and second axes may be slightly offset from one another or at non-zero angles relative to one another.

The first spring 116 of the load balancing arm 900 is similar in structure and function as the spring 116 of the load balancing arm 500 and, accordingly, reference is made to FIGS. 22, 24, 27, and 32 and the corresponding description of the spring 116 of the load balancing arm 500. The first spring 116 has a cylinder 384 and a rod 388. The cylinder 384 has a proximal end wall 390 at a proximal end 394 of the first spring 116 that is coupled to a vertical beam 392 of the support arm 110. As shown in FIG. 22, the vertical beam 392 extends from a top wall 406 to a bottom wall 408 of the support arm 110 and is sufficiently narrow that the links 124, 126 straddle the vertical beam 392 on opposite lateral sides thereof throughout the pivotable range of the load balancing arm 900. The proximal end wall 390 of the cylinder 384 may be coupled to the vertical beam 392 in any suitable manner, for example as by a protrusion 418, shown in FIG. 32, that fits within an opening 420 in the vertical beam 392, shown in FIGS. 24 and 25. The rod 388 is pivotably mounted to the distal ends 162 of the links 124, 126 via the pin 360 of the afore described carriage slide 364. In operation, the links 124, 126 straddle the first spring 116 on laterally opposite sides of the first spring 116 throughout the pivotable range of the load balancing arm 900.

Details of the second spring 918 are shown in FIGS. 55-59 and 61-63. The second spring 918 has a rod 984 and a cylinder 988. The rod 984 is connected to the carriage slide 364 and the cylinder 988 is connected to the wall 928 of the support arm 110 so that the second spring 918 exerts a biasing force that biases the carriage slide 364 and thus the distal ends 162 of the links 124, 126 toward the distal end 152 of the support arm 110. The rod 984 of the second spring 918, in the illustrated embodiment also the proximal end 922 of the second spring 918, is connected to the carriage slide 364 such that the rod 984 and the carriage slide 364 do not separate due to the biasing force. In this way, the proximal end 922 of the second spring 918, the carriage slide 364, and the distal end 158 of the first spring 116 are configured to move together in unison as the carriage slide 364 moves relative to the support arm 110. In the illustrated embodiment, the rod 984 of the second spring 918, the carriage slide 364, and the rod 388 of the first spring 116 are connected relative to each other and move together in unison as the carriage slide 364 moves relative to the support arm 110. As will be described in greater detail below, the cylinder 988 of the second spring 918, or more generally a distal end 992 of the second spring 918, is connected to the wall 928 of the support arm 110 such that the cylinder 988 and the wall 928 do not separate due to the afore described biasing force.

Figure 61:
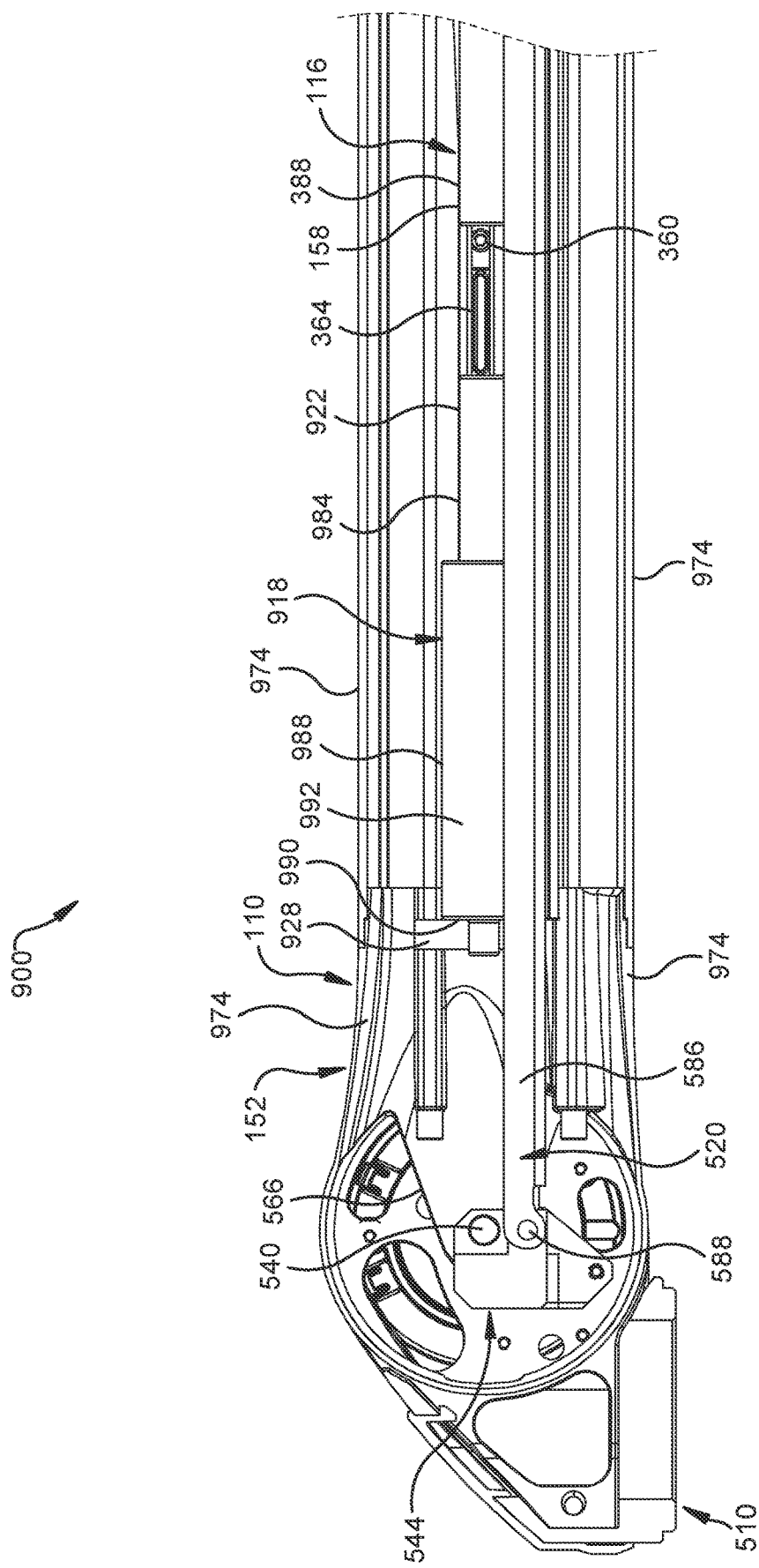
FIG. 61 is a side cross section view of a distal end of the FIG. 55 load balancing arm in a substantially horizontal position, showing internal components of the load balancing arm.
Figure 62:
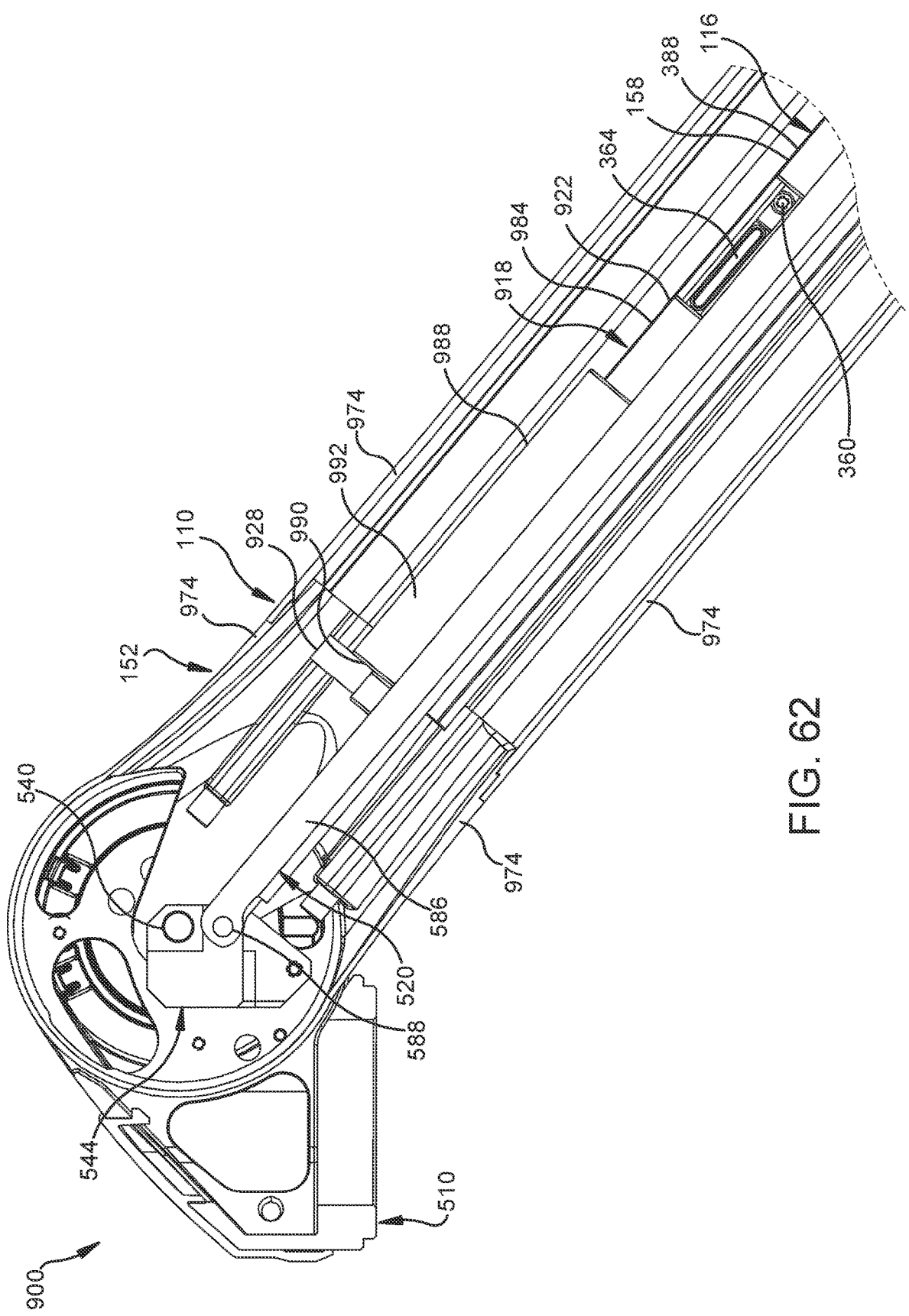
FIG. 62 is a side cross section view of the distal end of the FIG. 55 load balancing arm in a position upward from horizontal, showing internal components of the load balancing arm.
Figure 63:
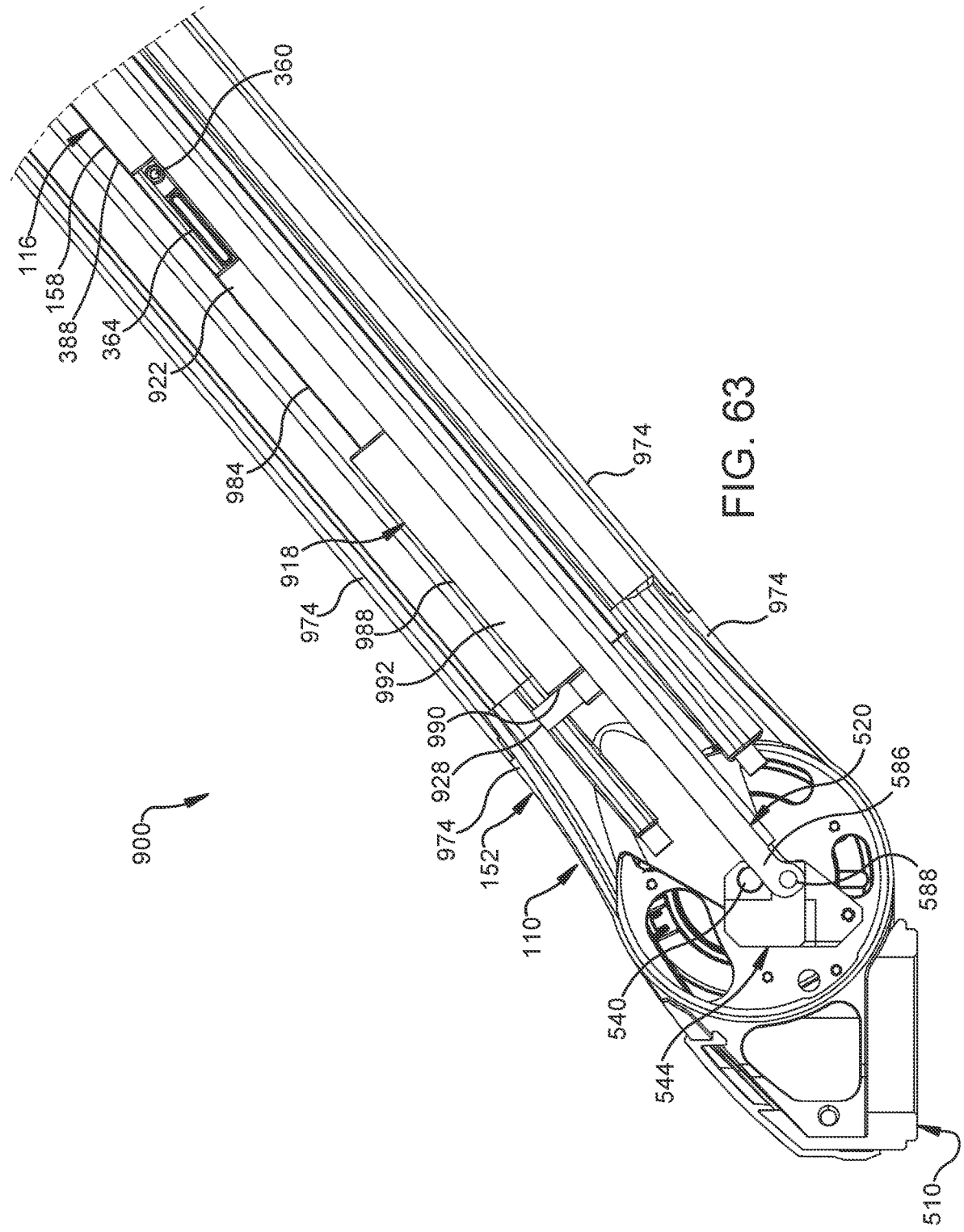
FIG. 63 is a side cross section view of the distal end of the FIG. 55 load balancing arm in a position downward from horizontal, showing internal components of the load balancing arm.

The rod 984 of the second spring 918, or the proximal end 922 of the second spring 918, may be connected to the carriage slide 364 to prevent separation therebetween in any suitable manner. Referring to FIGS. 61-63, the rod 984 of the second spring 918 is connected to the carriage slide 364 by spot welding although it will be appreciated that brazing, riveting, soldering and/or adhesive glue may additionally or alternately be used. In another form, the rod 984 may be connected to the carriage slide 364 by a threaded portion of the proximal end of the rod 984 threadedly engaging a corresponding axially extending threaded opening in the carriage slide 364, or by the proximal end of the rod 984 being fitted within an opening in the carriage slide 364 in an interference-fit manner. In yet another form, the rod 984 may be connected to the carriage slide 364 by means of a pivotable connection, for example, by means of a transverse pin mounted within the carriage slide 364 pivotably received in a transverse bore in the carriage slide 364. In this way, the proximal end 922 of the second spring 918 is pivotably connected to the carriage slide 364 to prevent separation between the proximal end 922 of the second spring 918 and the carriage slide 364 and also to provide tolerance for misalignment among the first and second springs 116, 918 and the carriage slide 364 axially relative to each another.

In the illustrated embodiment, the rod 984 of the second spring 918 and the rod 388 of the first spring 116 are connected to axially opposite ends of the carriage slide 364 in the slide direction of the carriage slide 364. Thus, the proximal end 922 of the second spring 918 and the distal end 158 of the first spring 116 are connected to axially opposite ends of the carriage slide 364 in the slide direction of the carriage slide 364. This aids the support arm 110 of the load balancing arm 900 in accommodating the second spring 918 within the cavity 154 (see FIG. 29) of the support arm 110 without a corresponding increase in the cross sectional area (perpendicular to the slide direction) of the support arm 110. As with the rod 388 of the first spring 116, the rod 984 of the second spring 918 is pivotably mounted to the distal ends 162 of the links 124, 126 via the pin 360 of the carriage slide 364.

The wall 928 of the support arm 110 may take any suitable form to provide support for the second spring 918 at the distal end 152 of the support arm 110. Referring to FIGS. 56-59 and 61-63, the wall 928 is an internal wall that is supported by and projects inward from a perimeter wall 974 of the support arm 110 that surrounds the first and second springs 116, 718. In the present embodiment, the wall 928 is cast integrally with the support arm 110 as a monolithic structure. The cylinder 988 of the second spring 918 has a distal end wall 990 at the distal end 992 of the second spring 918 that is connected to the wall 928. The connection between the wall 928 and the cylinder 988 of the second spring 918 prevents the cylinder 988 and the distal end 992 of the second spring 918 from moving toward the main pivot axis 132 of the proximal hub 104 or the proximal end 150 of the support arm 110, due to the biasing force exerted by the second spring 918. Thus, the second spring 918 biases the carriage slide 364 toward the wall 928 of the support arm 110 and, in so doing, biases the carriage slide 364 and thus the distal ends 162 of the links 124, 126 toward the distal end 152 of the support arm 110 and correspondingly away from the proximal end 150 of the support arm 110. In another form, the wall 928 may be a different structure from the remainder of the support arm 110 and be fixed to, for example by fasteners, an internal projection of the support arm 110. In another form, the wall 928 may be structured and function in a manner similar to the wall 728 of the support arm 110 of the load balancing arm 700.

The distal end wall 990 of the cylinder 988 may be connected to the wall 928 to prevent separation therebetween in any suitable manner. Referring to FIGS. 56-59 and 61-63, the distal end wall 990 of the cylinder 988 is connected to the wall 928 by spot welding although it will be appreciated that brazing, riveting, soldering and/or adhesive glue may additionally or alternately be used. In another form, the distal end wall 990 of the cylinder 988 may be connected to the wall 928 by an axially extending threaded protrusion of the distal end wall 990 threadedly engaging a corresponding axially extending threaded opening in the wall 928, or by a protrusion of the distal end wall 990 being fitted within an opening in the wall 928 in an interference-fit manner. In yet another form, the distal end wall 990 may be connected to the wall 928 by means of a pivotable connection, for example, by means of a transverse pin mounted within the wall 928 pivotably received in a transverse bore in the distal end wall 990. In this way, the distal end 992 of the second spring 918 is pivotably connected to the wall 928 to prevent separation between the distal end 992 of the second spring 918 and the wall 928 and also to provide tolerance for misalignment among the first and second springs 116, 918, the carriage slide 364, and the wall 928 axially relative to each another.

Reference is now made to FIGS. 64-66, which show the load balancing arm 900 in three different vertical positions, and FIGS. 61-63, which show the distal ends 162 of the links 124, 126 relative to the distal end 152 of the support arm 110 in the three respective vertical positions, as well as the corresponding biasing effects of the first and second springs 116, 918 in the three respective vertical positions. The links 124, 126 are shown adjusted to their maximum height in FIGS. 61-66 (the height from axis 142 to axis 132 in FIGS. 26 and 33), thereby maximizing the moment, or mechanical advantage, of the load balancing arm 900.

In FIGS. 61 and 64, the support arm 110 is in a substantially horizontal position. Here, the first spring 116 is shown exerting a biasing force between the main pivot axis 132 and the distal end 158 of the first spring 116, and the second spring 918 is shown exerting a biasing force between the proximal end 922 of the second spring 918 and the wall 928 at the distal end 152 of the support arm 110. In the present embodiment, as the first spring 116 is a tension spring, the first spring 116 biases the distal ends 162 of the links 124, 126 toward the distal end 152 of the support arm 110 and thus away from the proximal end 150 of the support arm 110 and away from the main pivot axis 132. Also, as the second spring 918 is a compression spring 918 in the present embodiment, the second spring 918 likewise biases the distal ends 162 of the links 124, 126 away from the proximal end 150 of the support arm 110 and away from the main pivot axis 132. Thus, both the first spring 116 and the second spring 918 contribute to the biasing force that biases the distal ends 162 of the links 124, 126 away from the proximal end 150 of the support arm 110 and away from the main pivot axis 132. As the distal ends 162 of the links 124, 126 are pivotably mounted to the distal end 158 of the first spring 116 and the proximal end 922 of the second spring 918, the biasing forces exerted by the first and second springs 116, 918 are transmitted through the links 124, 126 to the link bearing element 108 thereby to generate a moment about the main pivot axis 132 of the proximal hub 104 that counters a moment generated by the medical device load at the distal end 152 of the support arm 110.

In FIGS. 62 and 65, the support arm 110 is shown pivoted about the main pivot axis 132 about 30 degrees upward relative to horizontal. As compared to FIGS. 61 and 64, the first spring 116 in FIGS. 62 and 65 is shorter in length from its proximal end 394 to its distal end 158 and the second spring 918 is greater in length from its proximal end 922 to its distal end 992. Accordingly, in this position, the biasing force that the first spring 116 exerts to bias the distal ends 162 of the links 124, 126 toward the distal end 152 of the support arm 110 is less than that shown in FIGS. 61 and 64, and the biasing force that the second spring 918 exerts to bias the distal ends of the links 124, 126 toward the distal end 152 of the support arm 110 is less than that shown in FIGS. 61 and 64.

In FIGS. 63 and 66, the support arm 110 is shown pivoted about the main pivot axis 132 about 85 degrees downward from horizontal. As compared to FIGS. 61 and 64, the first spring 116 in FIGS. 63 and 66 is greater in length from its proximal end 394 to its distal end 158 and the second spring 918 is shorter in length from its proximal end 922 to its distal end 992. Accordingly, in this position, the biasing force that the first spring 116 exerts to bias the distal ends 162 of the links 124, 126 toward the distal end 152 of the support arm 110 is greater than that shown in FIGS. 61 and 64, and the biasing force that the second spring 918 exerts to bias the distal ends of the links 124, 126 toward the distal end 152 of the support arm 110 is greater than that shown in FIGS. 61 and 64.

As will be appreciated, then, the support arm 110 has an angle of rotation about the main pivot axis 132 of about 30 degrees upward from horizontal to about 85 degrees downward from horizontal.

In the FIGS. 55-66 embodiment, the first spring 116 includes a compression spring having the cylinder 384 and the rod 388 wherein the cylinder 384 includes the proximal end 394 of the first spring 116 and the rod 388 includes the distal end 158 of the first spring 116. This need not be the case and other embodiments are contemplated. For example, the cylinder 384 and rod 388 may be switched so that the cylinder 384 includes the distal end 158 of the first spring 116 and the rod 388 includes the proximal end 394 of the first spring 116. Also, in the FIGS. 55-66 embodiment, the second spring 918 includes a tension spring having the rod 984 and the cylinder 988 wherein the rod 984 includes the proximal end 922 of the second spring 918 and the cylinder 988 includes the distal end 992 of the second spring 918. This too need not be the case and other embodiments are contemplated. For example, the rod 984 and cylinder 988 may be switched so that the rod 984 includes the distal end 992 of the second spring 918 and the cylinder 988 includes the proximal end 922 of the second spring 918.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A load balancing arm for a medical device support system, comprising:
a proximal hub including a main bearing element defining a main pivot axis;
a link bearing element defining a link pivot axis;
a support arm having a proximal end and a distal end, wherein the distal end is configured to support a medical device load and the proximal end is pivotably mounted to the main bearing element for pivotable movement about the main pivot axis;
a first spring extending within a cavity of the support arm and mounted to exert a biasing force between the main pivot axis and a distal end of the first spring;
a second spring extending within the cavity of the support arm and mounted to exert a biasing force between a proximal end of the second spring and a wall at the distal end of the support arm; and,
at least one link having a proximal end pivotably mounted to the link bearing element for pivotable movement about the link pivot axis, and a distal end pivotably mounted to the distal end of the first spring and the proximal end of the second spring such that the biasing forces exerted by the first and second springs are transmitted through the link to the link bearing element thereby to generate a moment about the main pivot axis of the proximal hub that counters a moment generated by the medical device load at the distal end of the support arm.

2. The load balancing arm of claim 1, wherein the first spring and the second spring are connected functionally in series.

3. The load balancing arm of claim 1, wherein the first and second springs are oriented along an axis that extends radially from and perpendicular to the main pivot axis.

4. The load balancing arm of claim 1, wherein the first spring is configured to expand and contract along a first axis and the second spring is configured to expand and contract along a second axis, wherein the first and second axes coincide with one another.

5. The load balancing arm of claim 1, wherein the biasing force of the first spring is configured to bias the distal end of the at least one link toward the main pivot axis at the proximal end of the support arm and the biasing force of the second spring is configured to bias the distal end of the at least one link toward the wall at the distal end of the support arm.

6. The load balancing arm of claim 1, wherein the link pivot axis is axially spaced from the main pivot axis.

7. The load balancing arm of claim 1, wherein the link bearing element is an adjustable bearing element, wherein the link pivot axis is adjustable axially relative to the main pivot axis.

8. The load balancing arm of claim 1, wherein the first spring is a compression spring, and the second spring is a tension spring.

9. The load balancing arm of claim 1, further comprising a carriage slide that is slidable relative to the support arm, wherein the distal end of the link is pivotably mounted to the distal end of the first spring and the proximal end of the second spring via the carriage slide.

10. The load balancing arm of claim 9, wherein the proximal end of the second spring and the distal end of the first spring are connected to axially opposite ends of the carriage slide.

11. The load balancing arm of claim 9, wherein the proximal end of the second spring, the carriage slide, and the distal end of the first spring are configured to move together in unison as the carriage slide moves relative to the support arm.

12. The load balancing arm of claim 9, wherein the carriage slide is slidable within at least one groove in the support arm.

13. The load balancing arm of claim 12, wherein the groove is oriented along an axis that extends radially from and perpendicular to the main pivot axis.

14. The load balancing arm of claim 1, wherein the wall is an internal wall that is supported by and projects inward from a perimeter wall of the support arm that surrounds the first and second springs.

15. The load balancing arm of claim 1, wherein the first and second springs are gas springs having a cylinder and a rod, and the rod of the first spring and the cylinder of the second spring are pivotably mounted to the distal end of the at least one link.

16. The load balancing arm of claim 1, wherein the at least one link comprises a pair of links that straddle the first spring on laterally opposite sides of the first spring.

17. The load balancing arm of claim 1, wherein the support arm includes an intermediate portion between the proximal end and distal end of the support arm, and the intermediate portion has a relatively narrower height span than the proximal end of the support arm, and wherein the at least one link has at least one bend that corresponds to the difference in height span between the intermediate portion and the proximal end of the support arm.

18. The load balancing arm of claim 1, wherein the support arm has an angle of rotation about the main pivot axis of about 30 degrees upward from horizontal to about 85 degrees downward from horizontal.

19. The load balancing arm of claim 1, further comprising a parallel link that is pivotably connected at its proximal end to a pin supported by the proximal hub and at its distal end to a pin supported by a distal hub pivotably connected to the distal end of the support arm.

20. The load balancing arm of claim 19, wherein the parallel link includes a pair of laterally spaced side walls that straddle a vertically lower portion of the first and second springs on laterally opposite sides of the first and second springs.

21. The load balancing arm of claim 20, wherein the parallel link includes a pair of laterally spaced side walls that straddle the at least one link on laterally opposite sides of the at least one link over at least a portion of a pivotable range of the load adjustment arm.

22. A medical device support system, comprising:
a central shaft;
an extension arm mounted to the central shaft for rotational movement about the shaft; and
a load balancing arm including:
a proximal hub including a main bearing element defining a main pivot axis;
a counterbalancing bearing element defining a counterbalancing pivot axis;
a support arm having a proximal end and a distal end, wherein the distal end is configured to support a medical device load and the proximal end is pivotably mounted to the main bearing element for pivotable movement about the main pivot axis;
a first spring extending within a cavity of the support arm and mounted to exert a biasing force between the main pivot axis and a distal end of the first spring;
a second spring extending within the cavity of the support arm and mounted to exert a biasing force between a proximal end of the second spring and a wall at the distal end of the support arm; and,
at least one link having a proximal end pivotably mounted to the counterbalancing bearing element for pivotable movement about the counterbalancing pivot axis, and a distal end pivotably mounted to the distal end of the first spring and the proximal end of the second spring such that the biasing forces exerted by the first and second springs are transmitted through the link to the counterbalancing bearing element thereby to generate a moment about the main pivot axis of the proximal hub that counters a moment generated by the medical device load at the distal end of the support arm.

23. The medical device support system of claim 22, wherein the counterbalancing bearing element is an adjustable bearing element, and the counterbalancing pivot axis is adjustable relative to the main pivot axis.

* * * * *